US012797371B2

(12) United States Patent
Camberlein et al.

(10) Patent No.: US 12,797,371 B2
(45) Date of Patent: Nov. 17, 2026

(54) **INHIBITORS OF *PSEUDOMONAS AERUGINOSA* VIRULENCE FACTOR Lasβ**

(71) Applicants: Helmholtz-Zentrum Fur Infektionsforschung GmbH, Braunschweig (DE); Universite De Lille, Lille (FR)

(72) Inventors: Virgyl Camberlein, Braunschweig (DE); Anna Hirsch, Braunschweig (DE); Jörg Haupenthal, Braunschweig (DE); Andreas Kany, Braunschweig (DE); Jelena Konstantinovic, Braunschweig (DE); Katharina Rox, Braunschweig (DE); Yu Mi Park, Braunschweig (DE); Rolf Müller, Braunschweig (DE); Rebecca Deprez-Poulain, Lille (FR); Benoit Deprez, Lille (FR); Alaa Alhayek, Braunschweig (DE); Andreas Klein, Braunschweig (DE); Roya Shafiei, Braunschweig (DE)

(73) Assignees: HELMHOLTZ-ZENTRUM FUR INFEKTIONSFORSCHUNG GMBH, Braunschweig (DE); Universite De Lille, Lille (FR)

( * ) Notice: Subject to any disclaimer, the term of this patent is extended or adjusted under 35 U.S.C. 154(b) by 166 days.

(21) Appl. No.: 18/842,997

(22) PCT Filed: Mar. 1, 2023

(86) PCT No.: PCT/EP2023/055152
§ 371 (c)(1),
(2) Date: Aug. 30, 2024

(87) PCT Pub. No.: WO2023/166039
PCT Pub. Date: Sep. 7, 2023

(65) Prior Publication Data

US 2025/0170104 A1 May 29, 2025

(30) Foreign Application Priority Data

Mar. 1, 2022 (EP) .................................... 22290011

(51) Int. Cl.

| | |
|---|---|
| ***C07D 249/04*** | (2006.01) |
| ***A61K 31/4192*** | (2006.01) |
| ***A61P 31/04*** | (2006.01) |
| ***C07D 249/06*** | (2006.01) |
| ***C07D 417/04*** | (2006.01) |

(52) U.S. Cl.
CPC .......... *A61K 31/4192* (2013.01); *A61P 31/04* (2018.01); *C07D 249/04* (2013.01)

(58) Field of Classification Search
CPC ... C07D 249/04; C07D 249/06; C07D 417/04
See application file for complete search history.

(56) References Cited

FOREIGN PATENT DOCUMENTS

| | | | |
|---|---|---|---|
| JP | 2005321538 A | * | 11/2005 |
| WO | WO 2022/043322 A1 | | 3/2022 |

OTHER PUBLICATIONS

M.R. Hansen et al., "Triazole-containing N-acyl homoserine lactones targeting the quorum sensing system in Pseudomonas aeruginosa", Bioorganic & Medicinal Chemistry, 23 (2015), pp. 1638-1650.
A.M. Kany et al., "Tackling Pseudomonas aeruginosa Virulence by a Hydroxamic Acid-Based LasB Inhibitor", ACS Chemical Biology, (2018), 13, pp. 2449-2455.
S. Yahiaoui et al., "N-Aryl mercaptoacetamides as potential multi-target inhibitors of metallo-B-lactamases (MBLs) and the virulence factor LasB from Pseudomonas aeruginosa", RSC Medicinal Chemistry, 2021, 12, pp. 1698-1708.
A. Alhayek et al., "Discovery and Characterization of Synthesized and FDA-Approved Inhibitors of Clostridial and Bacillary Collagenases", Journal of Medicinal Chemistry, 2022, 65, pp. 12933-12955.
International Search Report issued Mar. 22, 2023 in corresponding PCT/EP2023/055152.
S.S. Magill et al., "Multistate Point-Prevalence Survey of Health Care-Associated Infections", The New England Journal of Medicine, 2014, 370(13), pp. 1198-1200.
M.J. Richards et al., "Nosocomial Infections in Pediatric Intensive Care Units in the United States", Pediatrics, 1999, 103(4), pp. 1-7.
G. Valenza et al., "Prevalence and antimicrobial susceptibility of microorganisms isolated from sputa of patients with cystic fibrosis", Journal of Cystic Fibrosis, 2008, vol. 7, pp. 123-127.
R. Sordé et al., "Management of refractory Pseudomonas aeruginosa infection in cystic fibrosis", Infection and Drug Resistance, 2011, vol. 4, pp. 31-41.
N. Mesaros et al., "Pseudomonas aeruginosa: resistance and therapeutic options at the turn of the new millennium", European Society of Clinical Microbiology and Infectious Diseases, 2007, vol. 13, pp. 560-570.
G. Taubes, "The Bacteria Fight Back", Science, 2008, vol. 321, pp. 356-360.
R.E.W. Hancock et al., "Antibiotic resistance in Pseudomonas aeruginosa: mechanisms and impact on treatment", Drug Resistance Update, 2000, vol. 3, pp. 247-250.
T. Strateva et al., "Pseudomonas aeruginosa—a phenomenon of bacterial resistance", Journal of Medical Microbiology, 2009, vol. 58, pp. 1133-1148.

(Continued)

*Primary Examiner* — Matthew P Coughlin
(74) *Attorney, Agent, or Firm* — Fox Rothschild LLP

(57) ABSTRACT

The present invention relates to compounds of formula (I) and the use thereof as inhibitors of *P. aeruginosa* virulence factor LasB.

(I)

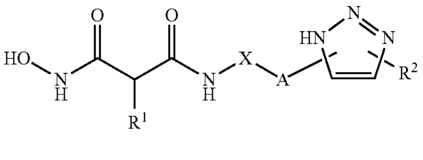

These compounds are useful in the treatment of bacterial infections, especially caused by *P. aeruginosa.*

19 Claims, 6 Drawing Sheets

(56) References Cited

OTHER PUBLICATIONS

F. Yoshimura et al. "Permeability of Pseudomonas aeruginosa Outer Membrane to Hydrophilic Solutes", Journal of Bacteriology, 1982, 152(2), pp. 636-642.
K.M. Pos, "Drug transport mechanism of the AcrB efflux pump", Biochimica et Biophysica Acta, 2009, vol. 1794, pp. 782-793.
M.A.S. Moreira et al., "Multidrug Efflux Systems in Gram-Negative Bacteria", Brazilian Journal of Microbiology, 2004, vol. 35, pp. 19-28.
R.E.W. Hancock et al., "Roles of Porin and B-Lactamase in B-Lactam Resistance of Pseudomonas aeruginosa", Reviews of Infectious Diseases, 1988, 10(4), pp. 770-775.
X-Z Li et al., "Role of Efflux Pump(s) in Intrinsic Resistance of Pseudomonas aeruginosa: Resistance to Tetracycline, Chloramphenicol, and Norfloxacin", Antimicrobial Agents and Chemotherapy, 1994, 38(8), pp. 1732-1741.
J.M. Thomson et al., "The threat of antibiotic resistance in Gram-negative pathogenic bacteria: B-lactams in peril!", Current Opinion in Microbiology, 2005, vol. 8, pp. 518-524.
L.B. Gasink et al., "Fluoroquinolone-Resistant Pseudomonas aeruginosa: Assessment of Risk Factors and Clinical Impact", The American Journal of Medicine, 2006, vol. 119, pp. 19-25.
K. Poole, "Aminoglycoside Resistance in Pseudomonas aeruginosa", Antimicrobial Agents and Chemotherapy, 2005, vol. 49, pp. 479-487.
M.D. Obritsch et al., "Nosocomial Infections Due to Multidrug-Resistant Pseudomonas aeruginosa: Epidemiology and Treatment Options", Pharmacotherapy, 2005, vol. 25, 1353-1364.
1995 ASCP Susceptibility Testing Group, "United States Geographic Bacteria Susceptibility Patterns", American Journal of Clinical Pathology, 1996, 106, pp. 275-281.
S.W. Dickey et al., "Different drugs for bad bugs: antivirulence strategies in the age of antibiotic resistance", Nature Reviews, 2017, vol. 16, pp. 457-471.
D.A. Rasko et al., "Anti-virulence strategies to combat bacteria-mediated disease", Nature Reviews, 2010, vol. 9, pp. 117-128.
T. Strateva et al., "Contribution of an arsenal of virulence factors to pathogenesis of Pseudomonas aeruginosa infections", Ann. Microbiol., 2011, vol. 61, pp. 717-732.
B. Heras et al., "Targeting virulence not viability in the search for future antibacterials", British Journal of Clinical Pharmacology, 2015, vol. 79, pp. 208-215.
A.E. Clatworthy et al., "Targeting virulence: a new paradigm for antimicrobial therapy", Nature Chemical Biology, 2007, 3(9), pp. 541-548.
S. Wagner et al., "Novel Strategies for the treatment of Pseudomonas aeruginosa infections", Journal of Medicinal Chemistry, 2016, vol. 59, pp. 5929-5969.
P.V. Liu, "Extracellular Toxins of Pseudomonas aeruginosa", The Journal of Infectious Diseases, 1974, vol. 130, pp. S94-S99.
K. Morihara et al., "Pseudomonas aeruginosa Elastase—Isolationi, Crystallization, and Preliminary Chacteritzation", The Journal of Biological Chemistry, 1965, 240(8), pp. 3295-3304.
L.W. Heck et al., "Specific Cleavage of Human Type III and IV Collagens by Pseudomonas aeruginosa Elastage", Infection and Immunity, 1986, 51(1), pp. 115-118.
L.W. Heck et al., "Degradation of IgA Proteins By Pseudomonas aeruginosa Elastase", The Journal of Immunology, 1990, 144(6),pp. 2253-2257.
I.A. Holder et al., "Experimental studies of the pathogenesis of infections owing to Pseudomonas aeruginosa: elastase, and IgG protease", Can. J. Microbiol., 1984, vol. 30, pp. 1118-1124.
D.R. Galloway, "Pseudomonas aeruginosa elastase and elastolysis revisited: recent developments", Molecular Microbiology, 1991, 5(10), pp. 2315-2321.
N, Parmely et al., "Proteolytic Inactivation of Cytokines by Pseudomonas aeruginosa", Infection and Immunity, 1990, 58(9), pp. 3009-3014.
W.I. Mariencheck et al., "Pseudomonas aeruginosa Elastase Degrades Surfactant Proteins A and D", American Journal of Respiratory Cell Molecular Biology, 2003, 28, pp. 528-537.
A. Schmidtchen et al., "Proteinases of common pathogenic bacteria degrade and inactivate the antibacterial peptide LL-37", Molecular Microbiology, 2002, 46(1), pp. 157-168.
K. Oda et al., "Purification and Properties of a Proteinaceous Metallo-Proteinase Inhibitor from *Streptomyces nigrescens* TK-23", Biochimica et Biophysica Acta, 1979, vol. 571, pp. 147-156.
N. Nishino et al., "Pseudomonas aeruginosa Elastase", The Journal of Biological Chemistry, 1979, 255(8), pp. 3482-3486.
E. Kessler et al., "In Vitro Inhibition of Pseudomonas aeruginosa Elastase by Metal-Chelating Peptide Derivatives", Infection and Immunity, 1982, 38(2), pp. 716-723.
G.R.A. Cathcart et al., "Novel Inhibitors of the Pseudomonas aeruginosa Virulence Factor LasB: a Potential Therapeutic Approach for the Attenuation of Virulence Mechanisms in Pseudomonal Infection", Antimicrobial Agents and Chemotherapy, 2011, 55(6), pp. 2670-2678.
F.R. Burns et al., "Inhibition of Pseudomonas aeruginosa Elastase and Pseudomonas Keratitis Using a Thiol-Based Peptide", Antimicrobial Agents and Chemotherapy, 1990, 34(11), pp. 2065-2069.
J. Zhu et al., Disarming Pseudomonas aeruginosa Virulence Factor LasB by Leveraging a Caenorhabditis elegans Infection Model, Chemistry & Biology, 2015, vol. 22, pp. 483-491.
O.A. Adekoya et al., "Inhibition of pseudolysin and thermolysin by hydroxamate-based MMP inhibitors", European Journal of Medicinal Chemistry, 2015, vol. 89, pp. 340-348.
J.L. Fullagar et al., "Antagonism of a zinc metalloprotease using a unique metal-chelating scaffold: tropolones as inhibitors of P. aeruginosa elastase", Chem. Commun., 2013, vol. 49, pp. 3197-3199.
A.M. Kany et al., "Binding Mode Characterization and Early in Vivo Evaluation of Fragment-Like Thiols as Inhibitors of the Virulence Factor LasB from Pseudomonas aeruginosa", ACS Infectious Diseases, 2018, vol. 4, pp. 988-997.
J. Konstantinovic et al., "N-Aryl-3-mercaptosuccinimides as Antivirulence Agents Targeting Pseudomonas aeruginosa Elastase and Clostridium Collagenases", Journal of Medicinal Chemistry, 2020. vol. 63, pp. 8359-8368.

* cited by examiner

INHIBITORS OF *PSEUDOMONAS AERUGINOSA* VIRULENCE FACTOR Lasβ

CROSS-REFERENCE TO RELATED APPLICATIONS

This application is a U.S. national phase application, pursuant to 35 U.S.C. § 371, of PCT Application No. PCT/EP2023/055152, filed Mar. 1, 2023, which claims priority from European Patent Application No. 22290011.0, filed on Mar. 1, 2022. The entire contents of these applications are incorporated herein by reference in their entirety.

The present invention relates to novel inhibitors of the *Pseudomonas aeruginosa* virulence factor LasB. These compounds are useful in the treatment of bacterial infections, especially caused by *P. aeruginosa.*

*P. aeruginosa* is a Gram-negative bacterium, which is ranked by the WHO as one of the most critical pathogens today (World Health Organization. Global Priority List of Antibiotic-Resistant Bacteria to Guide Research, Discovery, and Development of New Antibiotics. WHO 2017). This opportunistic bacterium causes around 10% of hospital-acquired infections and has a high occurrence among immunocompromised and cystic-fibrosis patients (Magill, S. S.; Edwards, J. R.; Bamberg, W.; Beldavs, Z. G.; Dumyati, G.; Kainer, M. A.; Lynfield, R.; Maloney, M.; McAllister-Hollod, L.; Nadle, J.; et al. *N. Engl. J. Med.* 2014, 370, 1198-1208; Richards, M. J.; Edwards, J. R.; Culver, D. H.; Gaynes, R. P. *Pediatrics* 1999, 103, e39; Valenza, G.; Tappe, D.; Turnwald, D.; Frosch, M.; König, C.; Hebestreit, H.; Abele-Horn, M. *J. Cyst. Fibros.* 2008, 7, 123-127; Sordé, R.; Pahissa, A.; Rello, *J. Infect. Drug Resist.* 2011, 4, 31-41). The development of potent antibiotics is urgently needed due to the lack of efficient therapeutics on the market (Mesaros, N.; Nordmann, P.; Plesiat, P.; Roussel-Delvallez, M.; Eldere, J. Van; Glupczynski, Y.; Laethem, Y. Van; Jacobs, F.; Lebecque, P.; Malfroot, A.; et al. *Clin. Microbiol. Infect.* 2007, 13, 560-578; Taubes, G. *Science* 2008, 321, 356-361). This task is complicated by the high intrinsic resistance of the pathogen (Hancock, R. E. W.; Speert, D. P. *Drug Resist. Updat.* 2000, 3, 247-255; Strateva, T.; Yordanov, D. *J. Med. Microbiol.* 2009, 58, 1133-1148).

*P. aeruginosa* has a particularly low permeability of the outer membrane, preventing the entrance of antibiotics into the cell (Nikaido, H.; Yoshimura, F. *J. Bacteriol.* 1982, 152, 636-642). Additionally, its efflux pumps efficiently transport undesired antimicrobials out of the cell and its inducible chromosomal β-lactamases are able to inactivate the corresponding β-lactam antibiotics (Pos, K. M. *Biochim. Biophys. Acta-Proteins Proteomics* 2009, 1794, 782-793; Moreira, M. A. S.; Souza, E. C. de; Moraes, C. A. de. Brazilian *J. Microbiol.* 2004, 35, 19-28; Hancock, R. E. W.; Woodruff, W. A. *Clin. Infect. Dis.* 1988, 10, 770-775; Li, X. Z.; Livermore, D. M.; Nikaido, H. *Antimicrob. Agents Chemother.* 1994, 38, 1732-1741). An additional difficulty is the rising mutational resistance rate of *P. aeruginosa* strains (Thomson, J. M.; Bonomo, R. A. *Curr. Opin. Microbiol.* 2005, 8, 518-524). For example, fluoroquinolone and aminoglycoside resistance have reached up to 30% (Gasink, L. B.; Fishman, N. O.; Weiner, M. G.; Nachamkin, I.; Bilker, W. B.; Lautenbach, E. *Am. J. Med.* 2006, 119, 19-25; Poole, K. *Antimicrob. Agents Chemother.* 2005, 49, 479-487). Furthermore, resistances against almost all drugs used for the treatment of infections with *P. aeruginosa* (for example cephalosporins and carbapenems) are described (Obritsch, M. D.; Fish, D. N.; MacLaren, R.; Jung, R. *Pharmacotherapy* 2005, 25, 1353-1364; ASCP Susceptibility Testing Group. United States Geographic Bacteria Susceptibility Patterns. *Am. J. Clin. Pathol.* 1996, 106, 275-281). These facts emphasize the urgent need for new therapeutic options.

Besides the traditional strategy to target bacterial viability, recently, special attention has been paid to targeting bacterial virulence as an alternative approach for fighting microbial infections (Dickey, S. W.; Cheung, G. Y. C.; Otto, M. *Nat. Rev. Drug Discov.* 2017, 16, 457-471; Rasko, D. A.; Sperandio, V. *Nat. Rev. Drug Discov.* 2010, 9, 117-128). Virulence factors are common among pathogenic bacteria and act by damaging their host or evading its immune response (Strateva, T.; Mitov, I. *Ann. Microbiol.* 2011, 61, 717-732). Inhibitors of virulence factors reduce bacterial virulence and in this way enable clearance of the pathogen by either the host's immune system or with the help of antibiotics (Heras, B.; Scanlon, M. J.; Martin, J. L. *Br. J. Clin. Pharmacol.* 2015, 79, 208-215; Clatworthy, A. E.; Pierson, E.; Hung, D. T. *Nat. Chem. Biol.* 2007, 3, 541-548). Although only a few compounds have reached clinical approval yet, many in vitro and in vivo studies support the efficacy of this strategy (Wagner, S.; Sommer, R.; Hinsberger, S.; Lu, C.; Hartmann, R. W.; Empting, M.; Titz, A. *J. Med. Chem.* 2016, 59, 5929-5969). The main advantage of this new approach is the reduced selection pressure on the bacteria and thus the lower risk for resistance development. In addition, these antivirulence agents do not harm the commensal bacteria.

A well-known antivirulence target of *P. aeruginosa* is the elastase LasB. This extracellular zinc-containing protease plays a role in the pathogenic invasion of tissues and is thought to be predominantly relevant during acute infections (Liu, P. V. *J. Infect. Dis.* 1974, 130, S94-S99). It has the ability to break down elastin, which is an important component of lung tissue and blood vessels (Morihara, K.; Tsuzuki, H.; Oka, T.; Inoue, H.; Ebata, M. *J. Biol. Chem.* 1965, 240, 3295-3304). Additionally, LasB can degrade fibrin, collagen and surfactant proteins in the lung and is also involved in the reduction of the host's immunity by inactivation of human immunoglobulins A and G, cytokines gamma-interferon and tumor necrosis factor α as well as the degradation of the antibacterial peptide LL-37 (Heck, L. W.; Morihara, K.; McRae, W. B.; Miller, E. *J. Infect. Immun.* 1986, 51, 115-118; Heck, L. W.; Alarcon, P. G.; Kulhavy, R. M.; Morihara, K.; Mestecky, M. W.; Russell, J. F. *J. Immunol.* 1990, 144, 2253-2257; Holder, I. A.; Wheeler, R. *Can. J. Microbiol.* 1984, 30, 1118-1124; Galloway, D. R. *Mol. Microbiol.* 1991, 5, 2315-2321; Parmely, M.; Gale, A.; Clabaugh, M.; Horvat, R.; Zhou, W. *Infect. Immun.* 1990, 58, 3009-3014; Mariencheck, W. I.; Alcorn, J. F.; Palmer, S. M.; Wright, J. R. *Am. J. Respir. Cell Mol. Biol.* 2003, 28, 528-537; Schmidtchen, A. et al. *Mol. Microbiol.* 2002, 46, 157-168).

Since LasB is an attractive antivirulence target, several LasB inhibitors have been described in the literature up to now: natural products such as *Streptomyces* metalloprotease inhibitor TK-23 (SMPI) from *Streptomyces nigrescens* and phosphoramidon (Oda, K.; Koyama, T.; Murao, S. *Biochim. Biophys. Acta* 1979, 571, 147-156; Nishino, N.; Powers, J. C. *J. Biol. Chem.* 1979, 255, 3482-19), small peptides containing metal-chelating motifs such as thiol or hydroxamate groups (Kessler, E.; Israel, M.; Landshman, N.; Chechick, A.; Blumberg, S. *Infect. Immun.* 1982, 38, 716-723; Cathcart, G. R. A.; Quinn, D.; Greer, B.; Harriott, P.; Lynas, J. F.; Gilmore, B. F.; Walker, B. *Antimicrob. Agents Chemother.* 2011, 55, 2670-2678; Burns, F. R.; Paterson, C. A.; Gray, R. D.; Wells, J. T. *Antimicrob. Agents Chemother.* 1990, 34, 2065-2069) and small synthetic molecules with hydroxamate, thiol or mercaptoacetamide groups (Zhu, J.; Cai, X.; Harris, T. L.; Gooyit, M.; Wood, M.; Lardy, M.; Janda, K. D. *Chem. Biol.* 2015, 22, 483-491; Adekoya, O. A.; Sjøli, S.; Wuxiuer, Y.; Bilto, I.; Marques, S. M.; Santos, M. A.; Nuti, E.; Cercignani, G.; Rossello, A.; Winberg, J. O.; et al. *Eur. J. Med. Chem.* 2015, 89, 340-348) as well as compounds based on tropolone (Fullagar, J. L.; Garner, A. L.; Struss, A. K.; Day, J. A.; Martin, D. P.; Yu, J.; Cai, X.; Janda, K. D.; Cohen, S. M. *Chem. Commun.* 2013, 49, 3197-3199).

Recently, a group of N-aryl mercaptoacetamides as potent LasB inhibitors has been described (Kany, A. M.; Sikandar, A.; Haupenthal, J.; Yahiaoui, S.; Maurer, C. K.; Proschak, E.; Kohnke, J.; Hartmann, R. W. *ACS Infect. Dis.* 2018, 4, 988-997). The crystal structure of the most promising compound described therein revealed the presence of two molecules in the binding pocket. In order to occupy the active site with a single molecule, a series of N-benzylamide/N-alkylamide derivatives were synthesized. However, this approach failed to improve the inhibitory potency of the initial ligand. Further LasB inhibitors are disclosed in WO 2022/043322 A1; Kany A. M., Sikandar A., Yahiaoui S., Haupenthal J., Walter I., Empting M., Kohnke J., Hartmann R. W. "Tackling *Pseudomonas aeruginosa* Virulence by a Hydroxamic Acid-Based LasB Inhibitor". *ACS Chem Biol.* 2018, 13, 2449-2455; Yahiaoui S., Voos K., Haupenthal J., Wichelhaus T. A., Frank D., Weizel L., Rotter M., Brunst S., Kramer J. S., Proschak E., Ducho C., Hirsch A. K. H. "N-Aryl mercaptoacetamides as potential multi-target inhibitors of metallo-β-lactamases (MBLs) and the virulence factor LasB from *Pseudomonas aeruginosa*". *RSC Med Chem.* 2021, 12, 1698-1708, doi:10.1039/D1MD00187F; and Konstantinovic J., Yahiaoui S., Alhayek A., Haupenthal J., Schönauer E., Andreas A., Kany A. M., Müller R., Koehnke J., Berger F. K., Bischoff M., Hartmann R. W., Brandstetter H., Hirsch A. K. H. "N-Aryl-3-mercaptosuccinimides as Antivirulence Agents Targeting *Pseudomonas aeruginosa* Elastase and *Clostridium* Collagenases". *J Med Chem.* 2020. 63, 8359-8368. doi: 10.1021/acs.jmedchem.0c00584.

It has been the object of the present invention to provide novel inhibitors of the *P. aeruginosa* virulence factor LasB.

The present invention provides compounds of formula (I)

(I)

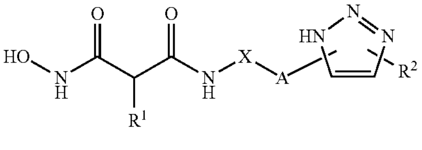

wherein

A is a bond, $CH_2$ or C=O;

X is an optionally substituted cycloalkylene group, an optionally substituted heterocycloalkylene group, an optionally substituted arylene group or an optionally substituted heteroarylene group;

$R^1$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which may optionally be substituted; and $R^2$ is hydrogen or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which may optionally be substituted;

or a pharmaceutically acceptable salt thereof.

Preferably, A is $CH_2$.

The present invention moreover provides compounds of formula (Ia)

(Ia)

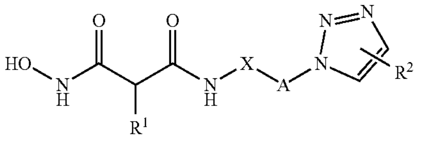

wherein A, X, $R^1$ and $R^2$ are as defined above or below, or a pharmaceutically acceptable salt thereof.

The present invention further provides compounds of formula (II)

(II)

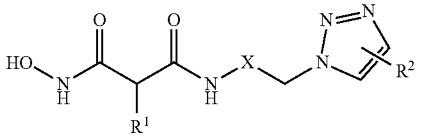

wherein X, $R^1$ and $R^2$ are as defined above or below, or a pharmaceutically acceptable salt thereof.

Preferably, X is an optionally substituted arylene group or an optionally substituted heteroarylene group;

Further preferably, X is an optionally substituted phenylene group or an optionally substituted heteroarylene group having 5 or 6 ring atoms that are selected from C, N, O and S.

Especially preferably, X is a 1,3 phenylene group.

Further especially preferably, X is a 1,4 phenylene group.

Further preferably, $R^1$ is a $C_{1-6}$ alkyl group; a heteroalkyl group containing from 1 to 6 carbon atoms and 1, 2, 3 or 4 heteroatoms selected from O, S and N; a $C_{3-7}$ cycloalklyl group; a $C_{4-10}$ alkylcycloalkyl group; or a $C_{7-12}$ aralkyl group; all of which may optionally be substituted.

Moreover preferably, $R^1$ is a $C_{1-6}$ alkyl group; a heteroalkyl group containing from 1 to 6 carbon atoms and 1, 2, 3 or 4 heteroatoms selected from O, S and N; a $C_{3-7}$ cycloalklyl group; or a group of formula $—CH_2—R^{11}$, wherein $R^{11}$ is a $C_{3-7}$ cycloalkyl group or an optionally substituted phenyl group.

Further preferably, $R^1$ is a $C_{1-6}$ alkyl group; or a group of formula $—CH_2—R^{11}$, wherein $R^{11}$ is a phenyl group or a cyclopropyl group.

Further preferably, $R^1$ is a $C_{1-4}$ alkyl group; or a group of formula $—CH_2—R^{11}$, wherein $R^{11}$ is a phenyl group or a cyclopropyl group.

Especially preferably, $R^1$ is an iso-butyl group (i.e., a group of formula $—CH_2CH(CH_3)_2$).

Moreover preferably, $R^1$ is an iso-propyl group (i.e., a group of formula $—CH(CH_3)_2$).

Further preferably, $R^2$ is a group of formula $—CH_2—NH—SO_2—R^3$ or $—CH_2—N(CH_3)—SO_2—R^3$, wherein $R^3$ is an optionally substituted phenyl group, an optionally substituted benzyl group, an optionally substituted $C_{3-10}$ cycloalkyl group, an optionally substituted $—CH_2—C_{3-10}$ cycloalkyl group, a $C_{1-6}$ alkyl group or a $C_{1-6}$ heteroalkyl group.

Moreover preferably, $R^2$ is a group of formula $—CH_2—Y—R^4$, wherein Y is selected from a bond, O, NH, S and NHCO; and $R^4$ is hydrogen, a $C_{1-6}$ heteroalkyl group or an optionally substituted phenyl group (preferably, $R^4$ is an optionally substituted phenyl group).

Further preferably, $R^2$ is an optionally substituted phenyl group.

Preferably, the optional substituents (preferably, 1 or 2 substituent(s)) at group $R^2$, $R^3$ or $R^4$ are independently selected from halogen atoms (e.g., F, Cl, Br, I), OH, $NH_2$, COOH, =O, phenyl, $C_{1-6}$ alkyl groups and $C_{1-6}$ heteroalkyl groups.

Moreover preferably, $R^2$ is selected from the following groups:

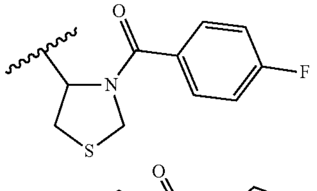

and

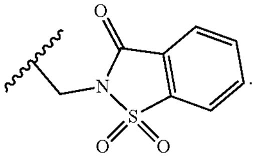

The most preferred compounds of the present invention are the compounds disclosed in the examples, or a salt thereof.

It is further preferred to combine the preferred embodiments of the present invention in any desired manner (e.g., any embodiment for $R^1$ may be combined with any embodiment of $R^2$).

The term "optionally substituted" refers to a group which is unsubstituted or substituted by one or more (especially by one, two or three; preferably by one or two) substituents.

If a group (e.g., group $R^1$ and/or group $R^2$) comprises more than one substituent, these substituents are independently selected, i.e., they may be the same or different.

If a group (e.g., group $R^1$ and/or group $R^2$) is substituted by a cyclic group, such as e.g., a cycloalkyl group or a heterocycloalkyl group, this cyclic group may be bonded to this group (e.g., group $R^1$ and/or group $R^2$) via a single or double bond or this cyclic group may be annulated or fused to said group (e.g., group $R^1$ and/or group $R^2$). Isatin is an example for a substituted phenyl group.

Examples for substituents are fluorine, chlorine, bromine and iodine and OH, =O, SH, $NH_2$, $—SO_3H$, $—SO_2NH_2$, —COOH, —COOMe, —COMe (Ac), $—NHSO_2Me$, $—SO_2NMe_2$, $—CH_2NH_2$, —NHAc, $—SO_2Me$, $—CONH_2$, —CN, $—NHCONH_2$, $—NHC(NH)NH_2$, $—NOHCH_3$, $—N_3$ and $—NO_2$ groups. Further examples of substituents are $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_1$-$C_{17}$ heterocycloalkyl, $C_4$-$C_{20}$ alkylcycloalkyl, $C_1$-$C_{19}$ heteroalkylcycloalkyl, $C_6$-$C_{18}$ aryl, $C_1$-$C_{17}$ heteroaryl, $C_7$-$C_{20}$ aralkyl and $C_1$-$C_{19}$ heteroaralkyl groups; especially $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_1$-$C_9$ heterocycloalkyl, $C_4$-$C_{12}$ alkylcycloalkyl, $C_1$-$C_{11}$ heteroalkylcycloalkyl, $C_6$-$C_{10}$ aryl, $C_1$-$C_9$ heteroaryl, $C_7$-$C_{12}$ aralkyl and $C_1$-$C_{11}$ heteroaralkyl groups, further preferably $C_1$-$C_6$ alkyl and $C_1$-$C_6$ heteroalkyl groups.

Preferred substituents are halogen atoms (e.g., F, Cl, Br, I) and groups of formula —OH, =O, —O—$C_{1-6}$ alkyl (e.g., —OMe, —OEt, —O-nPr, —O-iPr, —O-nBu, —O-iBu and —O-tBu), $—NH_2$, $—NHC_{1-6}$ alkyl, $—N(C_{1-6}$ alkyl$)_2$, —COOH, —COO—$C_{1-6}$ alkyl (e.g., —COOMe), —CO—$C_{1-6}$ alkyl (e.g., —COMe), $—COCF_3$, $—NHSO_2Me$, $—SO_2NMe_2$, $—OCH_2CH_2OCH_3$, $—SO_3H$, $—SO_2NH_2$, $—CONH_2$, $—CH_2NH_2$, —CN, —$C_{1-6}$alkyl (e.g., -Me, -Et, -nPr, -iPr, -nBu, -iBu, -tBu and $—CF_3$), —$C_{1-6}$ heteroalkyl, —SH, —S—CO—$C_{1-6}$ alkyl, —S—$C_{1-6}$ alkyl, —NHAc, $—NO_2$, —C≡CH, $—NHCONH_2$, $—SO_2Me$, $—SO_2CF_3$, phenyl, —CO-4-fluorophenyl, —$C_{3-6}$ cycloalkyl (e.g. cyclopropyl, cyclobutyl) and heterocycloalkyl containing 3 to 6 ring atoms selected from C, N, S and O.

Moreover preferred substituents are halogen atoms (e.g., F, Cl, Br, I), OH, $NH_2$, COOH, =O, phenyl, $C_{1-6}$ alkyl groups and $C_{1-6}$ heteroalkyl groups.

Further preferred substituents are halogen atoms (e.g., F, Cl, Br, I) and groups of formula —OH, =O, —O—$C_{1-6}$ alkyl (e.g., —OMe, —OEt, —O-nPr, —O-iPr, —O-nBu, —O-iBu and —O-tBu), $—NH_2$, $—NHC_{1-6}$ alkyl, $—N(C_{1-6}$ alkyl$)_2$, —COOH, —COO—$C_{1-6}$ alkyl (e.g., —COOMe), —CO—$C_{1-6}$ alkyl (e.g., —COMe), $—OCH_2CH_2OCH_3$, $—NHSO_2Me$, $—SO_2NMe_2$, $—SO_3H$, $—SO_2NH_2$, $—CONH_2$, $—CH_2NH_2$, —CN, —$C_{1-6}$ alkyl (e.g., -Me, -Et, -nPr, -iPr, -nBu, -iBu, -tBu and $—CF_3$), —SH, —S—CO—$C_{1-6}$ alkyl, —S—$C_{1-6}$ alkyl, —NHCOOtBu, —NHAc, phenyl, $—NO_2$, —C≡CH, $—NHCONH_2$, $—SO_2Me$ and cyclopropyl.

The substituent(s) is/are especially preferably independently selected from halogen (especially F and Cl), =O, —$C_{1-6}$ alkyl (e.g., -Me), $—CF_3$, —O—$C_{1-6}$ alkyl (e.g., —OMe), —OH, $—NH_2$, NHAc, —COOH, $—CONH_2$, —COO—$C_{1-6}$ alkyl (e.g., —COOMe), —O—$C_{1-6}$ alkyl (e.g., —COMe) and $—NO_2$.

The suffix "-ene" like e.g., in "phenylene" refers to the corresponding divalent group.

The expression alkyl refers to a saturated, straight-chain or branched hydrocarbon group that contains from 1 to 20 carbon atoms, preferably from 1 to 15 carbon atoms, especially from 1 to 10 (e.g., 1, 2, 3 or 4) carbon atoms, for example a methyl (Me, $CH_3$), ethyl (Et), n-propyl (nPr), iso-propyl (iPr), n-butyl (nBu), iso-butyl (iBu), sec-butyl (sBu), tert-butyl (tBu), n-pentyl, iso-pentyl, n-hexyl, 2,2-dimethylbutyl or n-octyl group.

Especially preferred alkyl groups are $C_{1-6}$ alkyl groups; moreover preferred alkyl groups are $C_{1-4}$ alkyl groups.

The expression $C_{1-6}$ alkyl refers to a saturated, straight-chain or branched hydrocarbon group that contains from 1 to 6 carbon atoms. The expression $C_{1-4}$ alkyl refers to a saturated, straight-chain or branched hydrocarbon group that contains from 1 to 4 carbon atoms. Examples are a methyl, ethyl, n-propyl, iso-propyl, n-butyl, iso-butyl, sec-butyl or tert-butyl group.

The expressions alkenyl and alkynyl refer to at least partially unsaturated, straight-chain or branched hydrocarbon groups that contain from 2 to 20 carbon atoms, preferably from 2 to 15 carbon atoms, especially from 2 to 10 (e.g., 2, 3 or 4) carbon atoms, for example an ethenyl (vinyl), propenyl (allyl), isopropenyl, butenyl, ethynyl (acetylenyl), propynyl (e.g., propargyl), butynyl, isoprenyl or hex-2-enyl group. Preferably, alkenyl groups have one or two (especially preferably one) double bond(s), and alkynyl groups have one or two (especially preferably one) triple bond(s).

Furthermore, the terms alkyl, alkenyl and alkynyl refer to groups in which one or more hydrogen atoms have been replaced by a halogen atom (preferably F or Cl) such as, for example, a 2,2,2-trichloroethyl or a trifluoromethyl group.

The expression heteroalkyl refers to an alkyl, alkenyl or alkynyl group in which one or more (preferably 1 to 8; especially preferably 1, 2, 3 or 4) carbon atoms have been replaced by an oxygen, nitrogen, phosphorus, boron, selenium, silicon or sulfur atom (preferably by an oxygen, sulfur or nitrogen atom) or by a SO or a $SO_2$ group. The expression heteroalkyl furthermore refers to a carboxylic acid or to a group derived from a carboxylic acid, such as, for example, acyl, acylalkyl, alkoxycarbonyl, acyloxy, acyloxyalkyl, carboxyalkylamide or alkoxycarbonyloxy. Furthermore, the term heteroalkyl refers to groups in which one or more hydrogen atoms have been replaced by a halogen atom (preferably F or Cl).

Preferably, a heteroalkyl group contains from 1 to 12 carbon atoms and from 1 to 8 heteroatoms selected from oxygen, nitrogen and sulfur (especially oxygen and nitrogen). Especially preferably, a heteroalkyl group contains from 1 to 6 (e.g., 1, 2, 3 or 4) carbon atoms and 1, 2, 3 or 4 (especially 1, 2 or 3) heteroatoms selected from oxygen, nitrogen and sulfur (especially oxygen and nitrogen). The term $C_1$-$C_{10}$ heteroalkyl refers to a heteroalkyl group containing from 1 to 10 carbon atoms and 1, 2, 3, 4, 5 or 6 heteroatoms selected from 0, S and/or N (especially 0 and/or N). The term $C_1$-$C_6$ heteroalkyl refers to a heteroalkyl group containing from 1 to 6 carbon atoms and 1, 2, 3 or 4 heteroatoms selected from 0, S and/or N (especially 0 and/or N). The term $C_1$-$C_4$ heteroalkyl refers to a heteroalkyl group containing from 1 to 4 carbon atoms and 1, 2 or 3 heteroatoms selected from 0, S and/or N (especially 0 and/or N).

Further preferably, the expression heteroalkyl refers to an alkyl group as defined above (straight-chain or branched) in which one or more (preferably 1 to 6; especially preferably 1, 2, 3 or 4) carbon atoms have been replaced by an oxygen, sulfur or nitrogen atom or a CO group or a SO group or a $SO_2$ group; this group preferably contains from 1 to 6 (e.g. 1, 2, 3 or 4) carbon atoms and 1, 2, 3 or 4 (especially 1, 2 or 3) heteroatoms selected from oxygen, nitrogen and sulfur (especially oxygen and nitrogen); this group may preferably be substituted by one or more (preferably 1 to 6; especially preferably 1, 2, 3 or 4) fluorine, chlorine, bromine or iodine atoms or OH, =O, SH, =S, $NH_2$, =NH, $N_3$, CN or $NO_2$ groups.

Examples of heteroalkyl groups are groups of formulae: $R^a$—O—$Y^a$—, $R^a$—S—$Y^a$—, $R^a$—SO—$Y^a$—, $R^a$—$SO_2$—$Y^a$—, $R^a$—N($R^b$)—$SO_2$—$Y^a$—, $R^a$—$SO_2$—N($R^b$)—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—$R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ being a hydrogen atom, a $C_1$-$C_6$ alkyl, a $C_2$-$C_6$ alkenyl or a $C_2$-$C_6$ alkynyl group; $R^b$ being a hydrogen atom, a $C_1$-$C_6$ alkyl, a $C_2$-$C_6$ alkenyl or a $C_2$-$C_6$ alkynyl group; $R^c$ being a hydrogen atom, a $C_1$-$C_6$ alkyl, a $C_2$-$C_6$ alkenyl or a $C_2$-$C_6$ alkynyl group; $R^d$ being a hydrogen atom, a $C_1$-$C_6$ alkyl, a $C_2$-$C_6$ alkenyl or a $C_2$-$C_6$ alkynyl group and $Y^a$ being a bond, a $C_1$-$C_6$ alkylene, a $C_2$-$C_6$ alkenylene or a $C_2$-$C_6$ alkynylene group, wherein each heteroalkyl group contains at least one carbon atom and one or more hydrogen atoms may be replaced by fluorine or chlorine atoms.

Specific examples of heteroalkyl groups are methoxy, trifluoromethoxy, ethoxy, n-propyloxy, iso-propyloxy, n-butoxy, tert-butyloxy, methoxymethyl, ethoxymethyl, —$CH_2CH_2OH$, —$CH_2OH$, —$SO_2Me$, —NHAc, methoxyethyl, 1-methoxyethyl, 1-ethoxyethyl, 2-methoxyethyl or 2-ethoxyethyl, methylamino, ethylamino, propylamino, isopropylamino, dimethylamino, diethylamino, isopropylethylamino, methylamino methyl, ethylamino methyl, diisopropylamino ethyl, methylthio, ethylthio, isopropylthio, enol ether, dimethylamino methyl, dimethylamino ethyl, acetyl, propionyl, butyryloxy, acetyloxy, methoxycarbonyl, ethoxycarbonyl, propionyloxy, acetylamino or propionylamino, carboxymethyl, carboxyethyl or carboxypropyl, N-ethyl-N-methylcarbamoyl or N-methylcarbamoyl. Further examples of heteroalkyl groups are nitrile (—CN), isonitrile, cyanate, thiocyanate, isocyanate, isothiocyanate and alkylnitrile groups.

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, =O, SH, =S, $NH_2$, =NH, $N_3$ or $NO_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, propellane (e.g., [1.1.1]propellane) tetraline, cyclopentylcyclohexyl, fluorocyclohexyl or cyclohex-2-enyl group. Preferably, the expression cycloalkyl refers to a saturated cyclic group that contains one or more rings (preferably 1 or 2), and contains from 3 to 14 ring carbon atoms, preferably from 3 to 10 (especially 3, 4, 5, 6 or 7) ring carbon atoms.

The expression heterocycloalkyl refers to a cycloalkyl group as defined above in which one or more (preferably 1, 2 or 3) ring carbon atoms have been replaced by an oxygen, nitrogen, silicon, selenium, phosphorus or sulfur atom (preferably by an oxygen, sulfur or nitrogen atom) or a SO group or a $SO_2$ group. A heterocycloalkyl group has preferably 1 or 2 ring(s) and 3 to 10 (especially 3, 4, 5, 6 or 7) ring atoms (preferably selected from C, O, N and S). The expression heterocycloalkyl refers furthermore to groups that are substituted by fluorine, chlorine, bromine or iodine atoms or by OH, =O, SH, =S, $NH_2$, =NH, $N_3$ or $NO_2$ groups. Examples are a piperidyl, prolinyl, imidazolidinyl, piperazinyl, morpholinyl (e.g., —N($CH_2CH_2$)$_2$O), urotropinyl, pyrrolidinyl, tetrahydrothiophenyl, tetrahydropyranyl, tetrahydrofuryl or 2-pyrazolinyl group and also lactames, lactones, cyclic imides and cyclic anhydrides.

The expression alkylcycloalkyl refers to groups that contain both cycloalkyl and alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two rings and from 3 to 10 (especially 3, 4, 5, 6 or 7) ring carbon atoms, and one or two alkyl, alkenyl or alkynyl groups (especially alkyl groups) having 1 or 2 to 6 carbon atoms.

The expression heteroalkylcycloalkyl refers to alkylcycloalkyl groups as defined above in which one or more (preferably 1, 2 or 3) carbon atoms have been replaced by an oxygen, nitrogen, silicon, selenium, phosphorus or sulfur atom (preferably by an oxygen, sulfur or nitrogen atom) or a SO group or a $SO_2$ group. A heteroalkylcycloalkyl group preferably contains 1 or 2 rings having from 3 to 10 (especially 3, 4, 5, 6 or 7) ring atoms, and one or two alkyl, alkenyl, alkynyl or heteroalkyl groups (especially alkyl or heteroalkyl groups) having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being saturated or mono-, di- or tri-unsaturated.

The expression aryl refers to an aromatic group that contains one or more rings and from 6 to 14 ring carbon atoms, preferably from 6 to 10 (especially 6) ring carbon atoms. The expression aryl refers furthermore to groups that are substituted by fluorine, chlorine, bromine or iodine atoms or by OH, SH, $NH_2$, $N_3$ or $NO_2$ groups.

Examples are the phenyl (Ph), naphthyl, biphenyl, 2-fluorophenyl, anilinyl, 3-nitrophenyl or 4-hydroxyphenyl group.

The expression heteroaryl refers to an aromatic group that contains one or more rings and from 5 to 14 ring atoms, preferably from 5 to 10 (especially 5 or 6 or 9 or 10) ring atoms, comprising one or more (preferably 1, 2, 3 or 4) oxygen, nitrogen, phosphorus or sulfur ring atoms (preferably 0, S or N). The expression heteroaryl refers furthermore to groups that are substituted by fluorine, chlorine, bromine or iodine atoms or by OH, SH, $N_3$, $NH_2$ or $NO_2$ groups. Examples are pyridyl (e.g. 4-pyridyl), imidazolyl (e.g. 2-imidazolyl), phenylpyrrolyl (e.g., 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, 4-hydroxypyridyl (4-pyridonyl), 3,4-hydroxypyridyl (3,4-pyridonyl), oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g., 3-pyrazolyl) and isoquinolinyl groups.

The expression aralkyl refers to groups containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are phenylcyclopentyl, cyclohexylphenyl as well as groups derived from toluene, xylene, mesitylene, styrene, benzyl chloride, o-fluorotoluene, 1H-indene, tetraline, dihydronaphthalene, indanone, cumene, fluorene and indane. An aralkyl group preferably contains one or two aromatic ring systems (especially 1 or 2 rings), each containing from 6 to 10 carbon atoms and one or two alkyl, alkenyl and/or alkynyl groups containing from 1 or 2 to 6 carbon atoms and/or a cycloalkyl group containing 3, 4, 5, 6 or 7 ring carbon atoms.

The expression heteroaralkyl refers to groups containing both aryl and/or heteroaryl groups and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (especially 1 or 2 rings), each containing from 5 or 6 to 9 or 10 ring atoms (preferably selected from C, N, O and S) and one or two alkyl, alkenyl and/or alkynyl groups containing 1 or 2 to 6 carbon atoms and/or one or two heteroalkyl groups containing 1 to 6 carbon atoms and 1, 2 or 3 heteroatoms selected from O, S and N and/or one or two cycloalkyl groups each containing 3, 4, 5, 6 or 7 ring carbon atoms and/or one or two heterocycloalkyl groups, each containing 3, 4, 5, 6 or 7 ring atoms comprising 1, 2, 3 or 4 oxygen, sulfur or nitrogen atoms.

Examples are arylheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroaryl-heterocycloalkyl, heteroarylheterocycloalkenyl, heteroarylalkylcycloalkyl, heteroaryl-alkylheterocycloalkenyl, heteroarylheteroalkylcycloalkyl, heteroarylheteroalkyl-cycloalkenyl and heteroarylheteroalkylheterocycloalkyl groups, the cyclic groups being saturated or mono-, di- or tri-unsaturated. Specific examples are a tetrahydroisoquinolinyl, benzoyl, phthalidyl, 2- or 3-ethylindolyl, 4-methylpyridino, 2-, 3- or 4-methoxyphenyl, 4-ethoxyphenyl, 2-, 3- or 4-carboxyphenylalkyl group.

As already stated above, the expressions cycloalkyl, heterocycloalkyl, alkylcycloalkyl, heteroalkylcycloalkyl, aryl, heteroaryl, aralkyl and heteroaralkyl also refer to groups that are substituted by fluorine, chlorine, bromine or iodine atoms or by OH, =O, SH, =S, $NH_2$, =NH, $N_3$ or $NO_2$ groups.

The term halogen refers to F, Cl, Br or I.

When an aryl, heteroaryl, cycloalkyl, alkylcycloalkyl, heteroalkylcycloalkyl, heterocycloalkyl, aralkyl or heteroaralkyl group contains more than one ring, these rings may be bonded to each other via a single or double bond or these rings may be annulated or fused or bridged.

Owing to their substitution, the compounds of the present invention may contain one or more centers of chirality. The present invention therefore includes both all pure enantiomers and all pure diastereomers and also mixtures thereof in any mixing ratio.

The present invention moreover also includes all cis/trans-isomers of the compounds of the present invention and also mixtures thereof. The present invention moreover includes all tautomeric forms of the compounds of the present invention.

The present invention further provides pharmaceutical compositions comprising one or more compounds described herein or a pharmaceutically acceptable salt, solvate or hydrate thereof, optionally in combination with one or more carrier substances and/or one or more adjuvants. The pharmaceutical composition of the present invention may contain a further antibacterial compound.

The compounds or pharmaceutical compositions of the present invention may be administered in combination with a further antibacterial compound.

The present invention furthermore provides compounds or pharmaceutical compositions as described herein for use in the treatment of bacterial infections, especially caused by *P. aeruginosa.*

The present invention further provides a compound as described herein or a pharmaceutical composition as defined herein for the preparation of a medicament for the treatment of bacterial infections, especially caused by *P. aeruginosa.*

Examples of pharmacologically acceptable salts of sufficiently basic compounds are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of the compounds described herein.

The compounds described herein may be solvated, especially hydrated. The solvation/hydration may occur during the process of production or as a consequence of the hygroscopic nature of the initially water-free compounds. The solvates and/or hydrates may e.g. be present in solid or liquid form.

The therapeutic use of the compounds described herein, their pharmacologically acceptable salts, solvates and hydrates, respectively, as well as formulations and pharmaceutical compositions also lie within the scope of the present invention.

In general, the compounds and pharmaceutical compositions described herein will be administered by using the established and acceptable modes known in the art.

For oral administration, such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g., liquid aerosol), transdermal, for example via an transdermal drug delivery system (TDDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules, one may use excipients as are e.g., vegetable, petroleum, animal or synthetic oils, wax, fat, and polyols. For the production of liquid solutions, emulsions or suspensions or syrups one may use as excipients e.g., water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin, especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations, one may use compressed gases suitable for this purpose, e.g., oxygen, nitrogen and carbon dioxide. The pharmaceutically useful agents may also contain additives for conservation, stabilization, e.g., UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 1 mg to about 10,000 mg, preferably from about 5 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

According to a moreover preferred embodiment, the present invention provides a method for inhibiting the *P. aeruginosa* virulence factor LasB in a subject which comprises administering to the subject an effective amount of a compound of formula (I), or a pharmaceutically acceptable salt thereof.

According to a moreover preferred embodiment, the present invention provides a method for treating a bacterial infection, which comprises administering to a subject in need of such treatment a therapeutically effective amount of a compound of formula (I), or a pharmaceutically acceptable salt thereof.

According to a further preferred embodiment, the present invention provides a method for treating a bacterial infection which comprises administering to a subject in need of such treatment a pharmaceutical composition comprising a compound of formula (I), or a pharmaceutically acceptable salt thereof.

As can be taken from the following examples, besides their high activity, the advantages of the compounds of the present invention are for example their excellent selectivity towards human off-targets, their chemical stability and extremely low toxicity.

EXAMPLES

I. Chemistry

1. General Information

Solvents for synthesis, analysis and purification were purchased as analytical-grade from commercial suppliers and used directly without further purification. Chemical reagents were purchased as reagent-grade and used without further purification.

NMR spectra were recorded on a Bruker UltraShield Plus 500 MHz device. LC-MS analysis were measured on a LC-MS system, consisting of a Thermo Scientific Dionex UltiMate 3000 pump, autosampler, column compartment, and detector (Thermo Fisher Scientific, Dreieich, Germany) and ESI quadrupole MS (MSQ Plus or ISQ EC, Thermo Fisher Scientific, Dreieich, Germany). High-resolution mass was determined by LCMS/MS using Thermo Scientific Q Exactive Focus Orbitrap LC-MS/MS system. Flash chromatography was performed using either a Teledyne ISCO CombiFlash Rf+ 150 or a Teledyne ISCO CombiFlash NEXTGEN 300+ equipped with RediSepRf silica columns. Preparative HPLC was performed on a Thermo Scientific Dionex Ultimate 3000 system.

2. General Synthesis Schemes

The compounds of the present invention can be prepared according to the following synthesis schemes:

Scheme 1

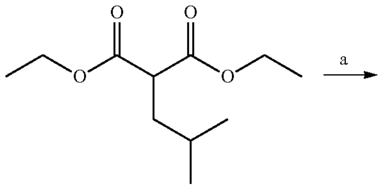

-continued

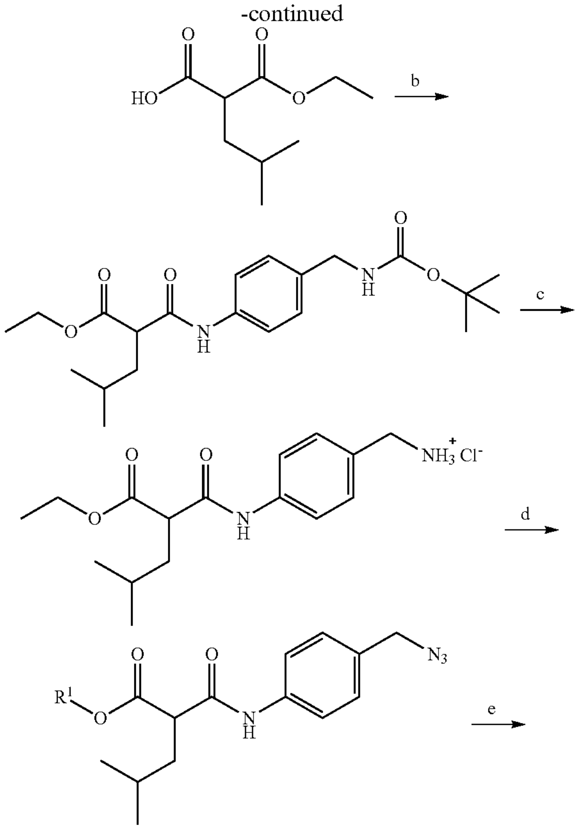

-continued

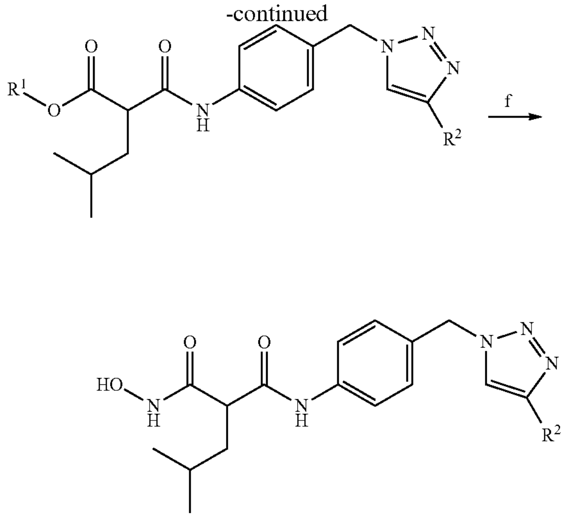

Reagents and conditions: a) NaOH, EtOH/$H_2O$ (4:1), rt., overnight, 80%; b) tert-butyl N-[(4-aminophenyl)methyl] carbamate, HBTU, $Et_3N$, DMF, rt., overnight, 47%; c) HCl 4M in dioxane, EtOH, 0° C. to rt., overnight, quantit. yield; d) azide-N-diazoimidazole-1-sulfonamide hydrogen sulfate, $K_2CO_3$, $ZnCl_2$, DIPEA, MeOH, 0° C. to rt., overnight, 58%; f) alkynes, $CuSO_4$ ($5H_2O$), sodium ascorbate, DMF/$H_2O$ (1.2:1), rt., overnight, 45-quant. yield; e) aq. hydroxylamine (50% in water w/w), KCN (cat.), MeOH, rt., overnight to 72 h, 10-85%.

Scheme 2

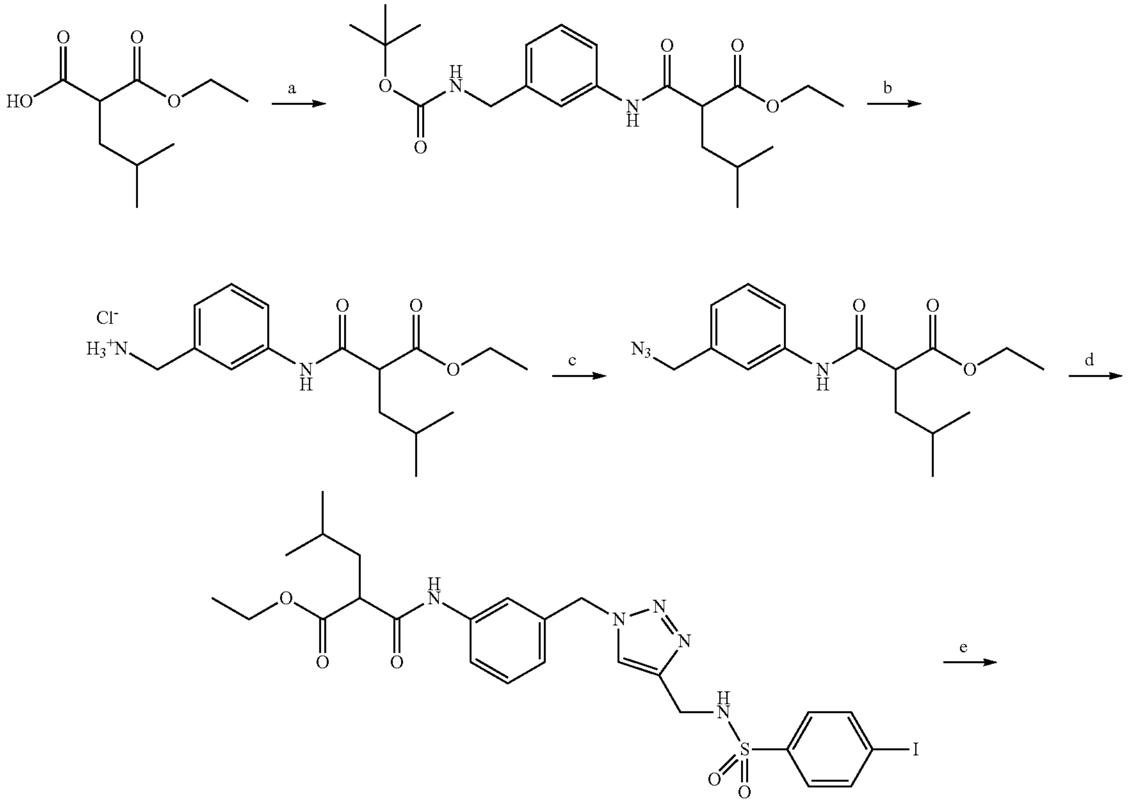

-continued

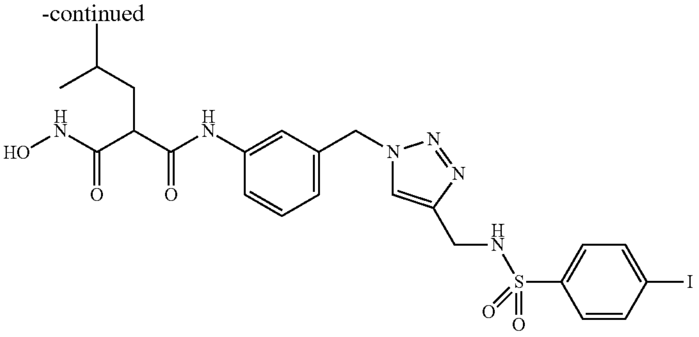

Reagents and conditions: a) tert-butyl N-[(3-aminophenyl)methyl]carbamate, HBTU, $Et_3N$, DMF, rt., overnight, 74%; b) HCl 4M in dioxane, EtOH, 0° C. to rt., overnight, quantit. yield; c) azide-N-diazoimidazole-1-sulfonamide hydrogen chloride, $K_2CO_3$, $ZnCl_2$, DIPEA, EtOH, 0° C. to rt., overnight, 31%; d) 93, $CuSO_4$ ($5H_2O$), sodium ascorbate, DMF/$H_2O$ (1.2:1), rt., overnight, 86%; e) aq. hydroxylamine (50% in water w/w), KCN (cat.), MeOH, 48 h, overnight, 7%.

Scheme 3

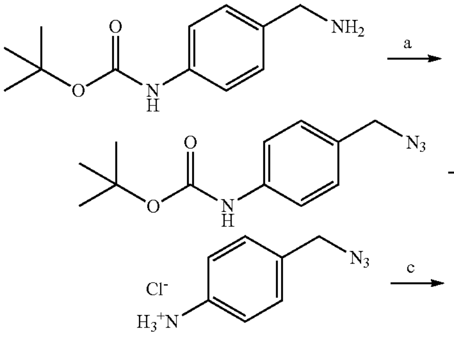

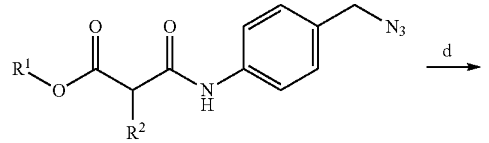

174: $R^1$ = methyl, $R^2$ = isopropyl (37%)
175: $R^1$ = ethyl, $R^2$ = methylcyclopropyl (43%)
211: $R^1$ = ethyl, $R^2$ = isopentyl (42%)

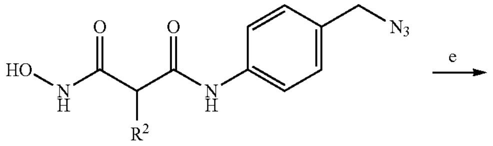

180: $R^1$ = methyl, $R^2$ = isopropyl (43%)
181: $R^1$ = ethyl, $R^2$ = methylcyclopropyl (44%)
214: $R^1$ = ethyl, $R^2$ = isopentyl (53%)

-continued

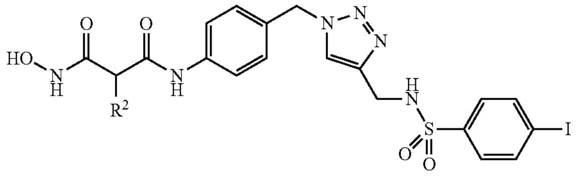

182: $R^2$ = isopropyl (55%)
183: $R^2$ = methylcyclopropyl (47%)
215: $R^2$ = isopentyl (30%)

Reagents and conditions: a) azide-N-diazoimidazole-1-sulfonamide hydrogen sulfate, $K_2CO_3$, $ZnCl_2$, DIPEA, MeOH, 0° C. to rt., overnight, quantit. yield; b) HCl 4 M in dioxane, $CH_2Cl_2$, MeOH, 0° C. to rt., overnight, quant. yield; c) carboxylic acids (174a-175a, 211a), HBTU, $Et_3N$, DMF, rt., overnight, 37-43%; d) aq. hydroxylamine (50% in water w/w), KCN (cat.), MeOH, rt., overnight, 43-53%; e) 93, $CuSO_4$ ($5H_2O$), sodium ascorbate, DMF/$H_2O$ (1.2:1), rt., overnight, 30-56%.

Scheme 4

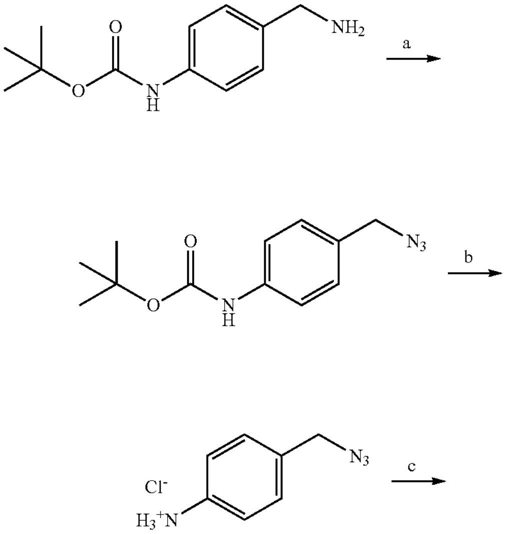

-continued

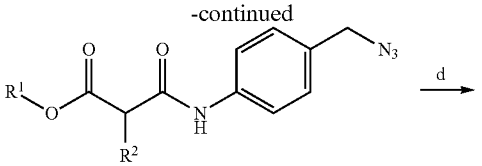

173: $R^1$ = ethyl, $R^2$ = benzyl (31%)
212: $R^1$ = methyl, $R^2$ = methyl (16%)

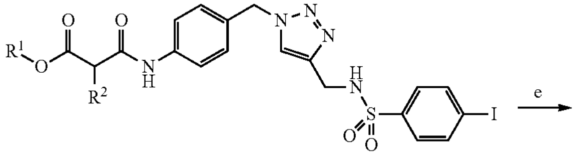

177: $R^1$ = ethyl, $R^2$ = benzyl (74%)
216: $R^1$ = methyl, $R^2$ = methyl (92%)

-continued

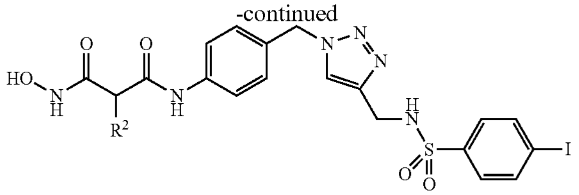

179: $R^2$ = benzyl (81%)
217: $R^2$ = methyl (52%)

Reagents and conditions: a) azide-N-diazoimidazole-1-sulfonamide hydrogen sulfate, $K_2CO_3$, $ZnCl_2$, DIPEA, MeOH, 0° C. to rt., overnight, quantit. yield; b) HCl 4 M in dioxane, $CH_2Cl_2$, MeOH, 0° C. to rt., overnight, quant. yield; c) carboxylic acids (174a-175a, 211a), HBTU, $Et_3N$, DMF, rt., overnight, 37-43%; d) 93, $CuSO_4$ ($5H_2O$), sodium ascorbate, DMF/$H_2O$ (1.2:1), rt., overnight, 74-92%; e) aq. hydroxylamine (50% in water w/w), KCN (cat.), MeOH, rt., 16-96 h, 52-81%. 93, $CuSO_4$ ($5H_2O$), sodium ascorbate, DMF/$H_2O$ (1.2:1), rt., overnight, 30-56%.

Scheme 5

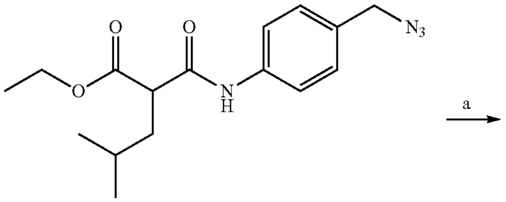

83

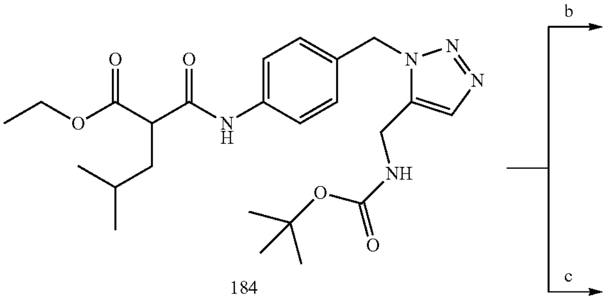

184

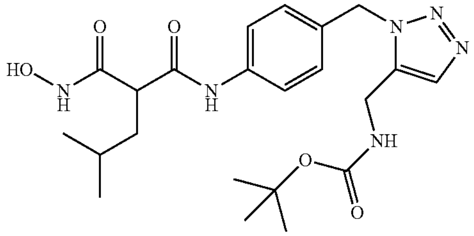

185

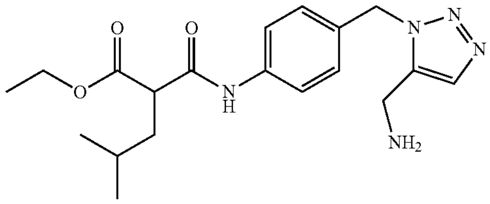

186

-continued

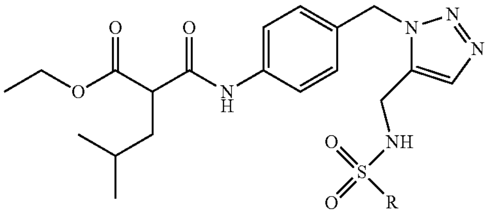

187: R = -4-iodobenzene (64%)
188: R = -4-fluorobenzene (70%)
189: R = -isobutyl (65%)

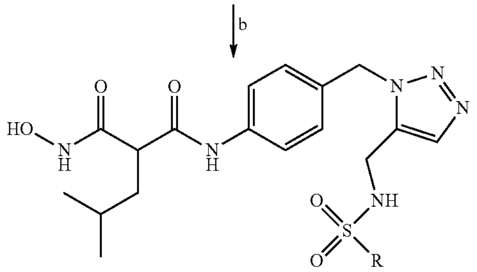

190: R = -4-iodobenzene (29%)
191: R = -4-fluorobenzene (37%)
192: R = -isobutyl (50%)

Reagents and conditions: a) N-Boc-propargylamine, Cp*RuCl (COD), dioxane, 80° C., overnight, 73%; b) aq. hydroxylamine (50% in water w/w), KCN (cat.), MeOH, rt., 48 h, 26-50%; c) HCl 4M in dioxane, $CH_2Cl_2$, EtOH, 0° C. to rt., overnight, quant. yield; d) R-S02-CI, DIPEA, DMF, 0° c. to rt., overnight, 64-70%.

Scheme 6

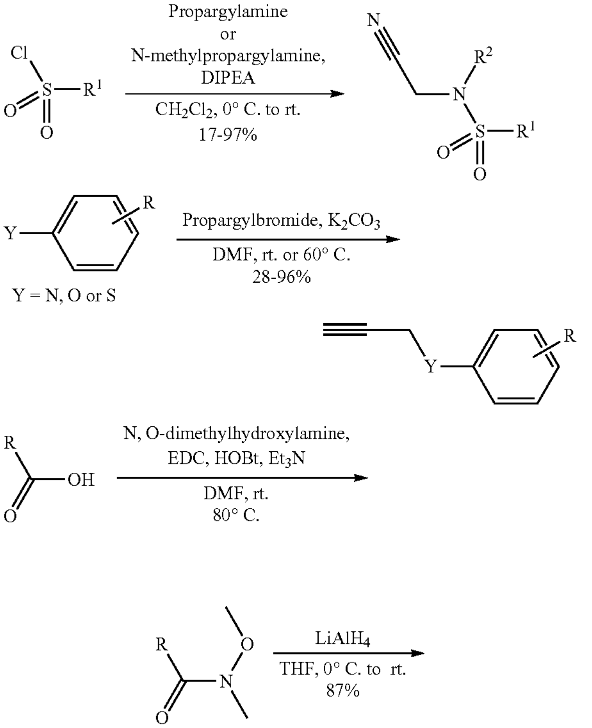

-continued

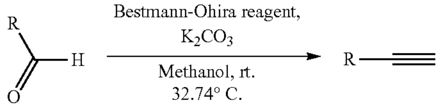

3. General Procedures

General Procedure A: Azide Formation

A suspension of amine (1 eq.), $ZnCl_2$ (0.06 eq.) and $K_2CO_3$ (2-4 eq.) in anhydrous methanol (0.18-0.25 M) under inert atmosphere was cooled down to 0° C. with an ice-bath. Besides, anhydrous N,N-diisopropylethylamine (1.1-2.1 eq.) was slowly added to a solution of 1H-imidazole-1-sulfonyl azide; hydrogen sulfate or hydrogen chloride (1.2 eq.) solubilized in anhydrous methanol (0.3 M) under inert atmosphere (solution A). The azide-containing solution A was immediately added dropwise to the first mixture at 0° C. Then, the cooling bath was removed, and the white mixture was stirred at room temperature overnight. The mixture was then cooled down to 0° C., diluted with water and carefully acidified to pH=2 with diluted aq. HCl (1 N). It was finally extracted with ethyl acetate. The combined organic layers were dried over $MgSO_4$, filtered and concentrated under reduced pressure or the residue was finally purified through flash chromatography to give the desired azide.

General Procedure B: Amide Formation

Carboxylic acid (1 eq.) and amine (1.1-1.6 eq.) were dissolved in N,N-dimethylformamide (0.28-0.45M) or $CH_2Cl_2$ (0.2 M). HBTU (1.1-1.7 eq.) or HOBt (0.1 eq.) and EDC-HCl (1.5 eq.), and trimethylamine or diisopropylethylamine (3-5 eq.) were then added, and the mixture was stirred overnight. The mixture was then washed with diluted aq. HCl (1 M), sat. aq. NaHCO$_3$ and sat. aq. NaCl. Combined organic layers were dried over $MgSO_4$, filtered and concentrated under reduced pressure or the residue was finally purified through flash chromatography to give the desired amide.

General Procedure C: Sulfonamide Formation

The amine (1-1.5 eq.) was dissolved in N,N-dimethylformamide or dichloromethane (0.04-0.10 M) and cooled down to 0° C. R1-sulfonyl chloride (1-1.2 eq.) was then carefully added followed by N,N-diisopropylethylamine (1.2-3 eq.). The mixture was allowed to reach room temperature and was stirred overnight. Then, the crude was diluted in aq. HCl (0.5 M) and extracted with ethyl acetate. Combined organic layers were dried over $MgSO_4$, filtered and concentrated under reduced pressure. The residue was finally purified through flash chromatography to afford the desired sulfonamide.

General Procedure D: Aminolysis

To an ester solution (1 eq.) in methanol (0.04-0.35M), was added aq. hydroxylamine (50% w/w in water, 0.04-0.35 M) and KCN (0.1-0.5 eq.). The mixture was stirred for 16 to 96 h. Then, the solvents were removed under reduced pressure, and the residue was purified through flash chromatography.

General Procedure E: Copper-Catalyzed Click Reaction

Azide (1 eq.) and alkyne (1.0-2.5 eq.) were dissolved in N,N-dimethylformamide (0.03-0.09 M) before an addition of copper sulfate pentahydrate (0.2-0.4 eq.) in water (0.05-0.09 M) and sodium ascorbate (0.5-1 eq.). The resulting mixture was stirred at room temperature overnight. The mixture was then diluted in water and extracted with ethyl acetate. The combined organic layers were dried over $MgSO_4$, filtered and concentrated under reduced pressure. The residue was finally purified through flash chromatography affording the desired 1,4-triazole.

General Procedure F: Monosaponification

Malonate diester (1 eq.) was dissolved in a mixture of methanol/water or ethanol/water (9:1-8:2, 0.32-0.58 M) and sodium hydroxide (1.2 eq.) or potassium hydroxide (1.0 eq.) was added. The reaction mixture was stirred at room temperature overnight.

Then, solvents were evaporated under reduced pressure, and the remaining aqueous mixture was diluted with sat. aq. $NaHCO_3$ and washed with $CH_2Cl_2$. The aqueous layer was then carefully acidified (pH-1) with aq. HCl and extracted with $CH_2Cl_2$. The combined organic layers were dried over $MgSO_4$, filtered and concentrated under reduced pressure affording the desired product.

General Procedure G: Boc Deprotection

The Boc-protected intermediate was dissolved in a mixture of ethanol and dichloromethane (1:1, 0.09-0.11 M), and the reaction was cooled down to 0° C. before addition of 4 N HCl in dioxane (0.18-0.22 M). The mixture was stirred at room temperature overnight. Then, solvents were evaporated to give the desired compound.

4. Synthesis of Compounds 1-(4-Chlorophenyl)-N-prop-2-ynyl-methanesulfonamide (147)

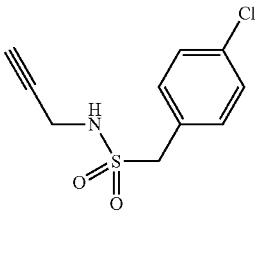

Compound 147 was synthesized according to the general procedure C, using propargylamine (94 μL, 1.47 mmol), (4-chlorophenyl)methanesulfonyl chloride (300 mg, 1.33 mmol) and N,N-diisopropylethylamine (464 μL, 2.67 mmol) in $CH_2Cl_2$ (5 mL) overnight. The crude product was purified by flash chromatography on silica gel (cHex to cHex/EtOAc: 7:3), affording compound 147 as a light yellow solid (187 mg, 45%). LC tr=3.88 min, MS (ESI−): m/z=242 and 244 $[M-H]^-$. $^1H$ NMR (500 MHz, DMSO-$d_6$) δ ppm: 7.68 (t, J=5.8 Hz, 1H), 7.46-7.45 (m, 2H), 7.42-7.40 (m, 2H), 4.40 (s, 2H), 3.79 (dd, J=5.8 and 2.4 Hz, 2H), 3.34 (t, J=2.4 Hz, 1H). $^{13}C$ NMR (126 MHz, DMSO-$d_6$) δ ppm: 133.0, 132.7 (2C), 129.2, 128.4 (2C), 80.5, 74.8, 57.0, 31.8.

4-Iodo-N-prop-2-ynyl-benzenesulfonamide (93)

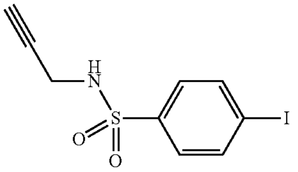

Compound 93 was synthesized according to the general procedure C, using propargylamine (70 μL, 1.09 mmol), 4-iodobenzenesulfonyl chloride (300 mg, 0.99 mmol) and N,N-diisopropylethylamine (345 μL, 1.98 mmol) in $CH_2Cl_2$ (5 mL) overnight. The crude product was purified by flash chromatography on silica gel (cHex to cHex/EtOAc: 7/3) affording compound 93 as a white solid (207 mg, 64%). LC tr=4.04 min, MS (ESI−): m/z=320 $[M-H]^-$. $^1H$ NMR (500 MHz, DMSO-$d_6$) δ ppm: 8.23 (br s, 1H), 7.98-7.97 (m, 2H), 7.56-7.55 (m, 2H), 3.71 (s, 2H), 3.06 (t, J=2.5 Hz, 1H). $^{13}C$ NMR (126 MHz, DMSO-$d_6$) δ ppm: 140.2, 138.0 (2C), 128.5 (2C), 100.6, 79.2, 74.9, 31.9.

4-Fluoro-N-prop-2-ynyl-benzenesulfonamide (141)

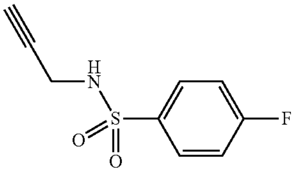

Compound 141 was synthesized according to the general procedure C, using propargylamine (217 μL, 3.39 mmol), 4-fluorobenzenesulfonyl chloride (600 mg, 3.08 mmol) and N,N-diisopropylethylamine (1070 μL, 6.17 mmol) in $CH_2Cl_2$ (10 mL) overnight. The crude product was purified by flash chromatography on silica gel (cHex to cHex/EtOAc: 7/3) affording compound 141 as a white solid (263 mg, 39%). LC tr=3.40 min, MS (ESI+): m/z=214 $[M+H]^+$. $^1H$ NMR (500 MHz, DMSO-$d_6$) δ ppm: 8.18 (br s, 1H), 7.88-7.85 (m, 2H), 7.44-7.41 (m, 2H), 3.71 (d, J=2.5 Hz, 2H), 3.03 (t, J=2.5 Hz, 1H). $^{13}C$ NMR (126 MHz, DMSO-$d_6$) δ ppm: 164.2 (d, J=250.3 Hz), 137.0 (d, J=2.8 Hz), 129.8 (d, J=9.2 Hz, 2C), 116.2 (d, J=22.8 Hz, 2C), 79.2, 74.8, 31.9.

4-Chloro-N-prop-2-ynyl-benzenesulfonamide (142)

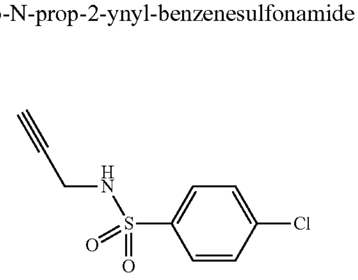

Compound 142 was synthesized according to the general procedure C, using propargylamine (100 μL, 1.56 mmol), 4-chlorobenzenesulfonyl chloride (300 mg, 1.42 mmol) and N,N-diisopropylethylamine (495 μL, 2.84 mmol) in $CH_2Cl_2$ (5 mL) overnight. The crude product was purified by flash chromatography on silica gel (cHex to cHex/EtOAc: 7/3) affording compound 142 as a white solid (283 mg, 85%). LC tr=3.81 min, MS (ESI+): m/z=230 $[M+H]^+$. $^1H$ NMR (500 MHz, DMSO-$d_6$) δ ppm: 8.25 (br s, 1H), 7.82-7.80 (m, 2H), 7.67-7.66 (m, 2H), 3.73 (d, J=2.5 Hz, 2H), 3.05 (t, J=2.5 Hz, 1H). $^{13}C$ NMR (126 MHz, DMSO-$d_6$) δ ppm: 139.5, 137.4, 129.2 (2C), 128.7 (2C), 79.1, 74.9, 31.9.

4-Methoxy-N-prop-2-ynyl-benzenesulfonamide (143)

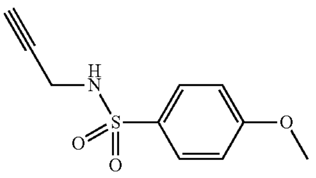

Compound 143 was synthesized according to the general procedure C, using propargylamine (205 μL, 3.19 mmol), 4-methoxybenzenesulfonyl chloride (600 mg, 2.90 mmol) and N,N-diisopropylethylamine (1010 μL, 5.81 mmol) in $CH_2Cl_2$ (10 mL) overnight. The crude product was purified by flash chromatography on silica gel (cHex to cHex/EtOAc: 5/5) affording compound 143 as a yellowish solid (528 mg, 76%). LC tr=3.35 min, MS (ESI+): m/z=226 $[M+H]^+$. $^1H$ NMR (500 MHz, DMSO-$d_6$) δ ppm: 7.95 (br s, 1H), 7.74-7.71 (m, 2H), 7.11-7.08 (m, 2H), 3.83 (s, 3H), 3.64 (d, J=2.5 Hz, 2H), 3.04 (t, J=2.5 Hz, 1H). $^{13}C$ NMR (126 MHz, DMSO-$d_6$) δ ppm: 162.0, 132.1, 128.9 (2C), 114.2 (2C), 79.5, 74.6, 55.6, 31.9.

4-Phenyl-N-prop-2-ynyl-benzenesulfonamide (95)

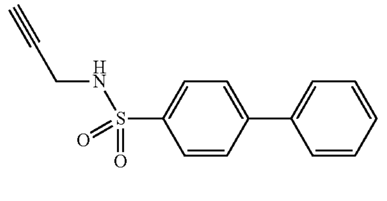 [SMILES: C#CCNS(=O)(=O)c1ccc(-c2ccccc2)cc1]

Compound 95 was synthesized according to the general procedure C, using propargylamine (83.6 μL, 1.31 mmol), 4-phenylbenzenesulfonyl chloride (300 mg, 1.19 mmol) and N,N-diisopropylethylamine (414 μL, 2.37 mmol) in $CH_2Cl_2$ (5 mL) overnight. Compound 95 was obtained as a white solid (298 mg, 91%) and used in the next step without further purifications. LC tr=4.39 min, MS (ESI+): m/z=272 $[M+H]^+$. $^1H$ NMR (500 MHz, DMSO-$d_6$) δ ppm: 8.20 (t, J=5.7 Hz, 1H), 7.89 (s, 4H), 7.74 (d, J=7.5 Hz, 2H), 7.51 (t, J=7.4 Hz, 2H), 7.44 (t, J=7.2 Hz, 1H), 3.73 (dd, J=6.3 and 2.6 Hz, 2H), 3.06 (t, J=2.6 Hz, 1H). $^{13}C$ NMR (126 MHz, DMSO-$d_6$) δ ppm: 144.0, 139.2, 138.6, 129.1 (2C), 128.5, 127.4 (2C), 127.3 (2C), 127.1 (2C), 79.4, 74.8, 32.0.

2-Chloro-N-prop-2-ynyl-benzenesulfonamide (144)

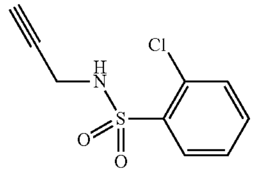

Compound 144 was synthesized according to the general procedure C, using propargylamine (167 μL, 2.21 mmol), 2-chlorobenzenesulfonyl chloride (500 mg, 2.37 mmol) and N,N-diisopropylethylamine (825 μL, 4.74 mmol) in $CH_2Cl_2$ (10 mL) overnight. The crude product was purified by flash chromatography on silica gel (cHex to cHex/EtOAc: 7/3) affording compound 144 as a white solid (478 mg, 87%). LC tr=3.49 min, MS (ESI+): m/z=230 $[M+H]^+$. $^1H$ NMR (500 MHz, DMSO-$d_6$) δ ppm: 8.33 (br s, 1H), 7.99-7.97 (m, 1H), 7.66-7.62 (m, 2H), 7.54-7.51 (m, 1H), 3.78 (d, J=2.5 Hz, 2H), 2.96 (t, J=2.5 Hz, 1H). $^{13}C$ NMR (126 MHz, DMSO-$d_6$) δ ppm: 138.1, 134.1, 131.6, 130.9, 130.5, 127.5, 79.1, 74.3, 31.8.

3-Chloro-N-prop-2-ynyl-benzenesulfonamide (145)

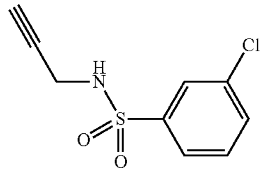

Compound 145 was synthesized according to the general procedure C, using propargylamine (167 μL, 2.21 mmol), 3-chlorobenzenesulfonyl chloride (500 mg, 2.37 mmol) and N,N-diisopropylethylamine (825 μL, 4.74 mmol) in $CH_2Cl_2$ (10 mL) overnight. The crude product was purified by flash chromatography on silica gel (cHex to cHex/EtOAc: 7/3) affording compound 145 as a white solid (300 mg, 54%). LC tr=3.81 min, MS (ESI−): m/z=228 $[M-H]^-$. $^1H$ NMR (500 MHz, DMSO-$d_6$) δ ppm: 8.30 (br s, 1H), 7.83-7.82 (m, 1H), 7.78-7.72 (m, 2H), 7.64-7.61 (m, 1H), 3.76 (d, J=2.4 Hz, 2H), 3.05 (t, J=2.4 Hz, 1H). $^{13}C$ NMR (126 MHz, DMSO-$d_6$) δ ppm: 142.5, 133.6, 132.5, 131.2, 126.4, 125.4, 79.1, 74.9, 31.9.

3,4-Dichloro-N-prop-2-ynyl-benzenesulfonamide (146)

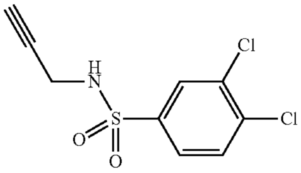

Compound 146 was synthesized according to the general procedure C, using propargylamine (172 µL, 2.69 mmol), 3,4-chlorobenzenesulfonyl chloride (600 mg, 2.44 mmol) and N,N-diisopropylethylamine (851 µL, 4.89 mmol) in $CH_2Cl_2$ (10 mL) overnight. The crude product was purified by flash chromatography on silica gel (cHex to cHex/EtOAc: 7/3) affording compound 146 as a white solid (436 mg, 66%). LC tr=4.22 min, MS (ESI−): m/z=262, 264 and 266 $[M-H]^-$. $^1H$ NMR (500 MHz, DMSO-$d_6$) δ ppm: 8.38 (br s, 1H), 8.00-7.99 (m, 1H), 7.89-7.88 (m, 1H), 7.77-7.76 (m, 1H), 3.78 (d, J=2.3 Hz, 2H), 3.09 (t, J=2.3 Hz, 1H). $^{13}C$ NMR (126 MHz, DMSO-$d_6$) δ ppm: 141.0, 135.6, 131.9, 131.5, 128.6, 127.0, 79.0, 75.1, 31.9.

N-Prop-2-ynylbenzenesulfonamide (148)

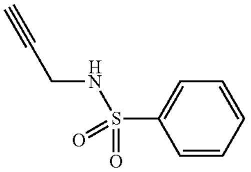

Compound 148 was synthesized according to the general procedure C, using propargylamine (239 µL, 3.74 mmol), benzenesulfonyl chloride (600 mg, 3.4 mmol) and N,N-diisopropylethylamine (1180 µL, 6.79 mmol) in $CH_2Cl_2$ (10 mL) overnight. The crude product was purified by flash chromatography on silica gel (cHex to cHex/EtOAc: 7/3) affording compound 148 as light yellow oil (527 mg, 78%). LC tr=3.17 min, MS (ESI+): m/z=196 $[M+H]^+$. $^1H$ NMR (500 MHz, DMSO-$d_6$) δ ppm: 8.16 (br s, 1H), 7.82-7.80 (m, 2H), 7.66-7.63 (m, 1H), 7.60-7.57 (m, 2H), 3.69 (d, J=2.5 Hz, 2H), 3.04 (t, J=2.5 Hz, 1H). $^{13}C$ NMR (126 MHz, DMSO-$d_6$) δ ppm: 140.5, 132.6, 129.1 (2C), 126.7 (2C), 79.3, 74.6, 31.9.

N-Prop-2-ynylcyclohexanesulfonamide (149)

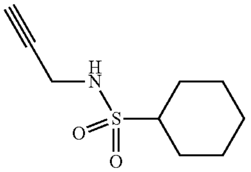

Compound 149 was synthesized according to the general procedure C, using propargylamine (193 µL, 3.01 mmol), cyclohexanesulfonyl chloride (500 mg, 2.74 mmol) and N,N-diisopropylethylamine (954 µL, 5.47 mmol) in $CH_2Cl_2$ (10 mL) overnight. The crude product was purified by flash chromatography on silica gel (cHex to cHex/EtOAc: 4/6) affording compound 149 as yellow oil (116 mg, 20%). LC tr=not visible (254 nm), MS (ESI+): no ionization $[M+H]^+$; MS (ESI−): no ionization $[M-H]^-$. $^1H$ NMR (500 MHz, DMSO-$d_6$) δ ppm: 7.57 (t, J=6.0 Hz, 1H), 3.77 (dd, J=6.0 and 2.5 Hz, 2H), 3.29 (t, J=2.5 Hz, 1H), 2.95 (tt, J=17.6 and 3.4 Hz, 1H), 2.07-2.05 (m, 2H), 1.79 (dt, J=12.7 and 2.9 Hz, 2H), 1.63 (dt, J=12.7 and 3.4 Hz, 1H), 1.38-1.08 (m, 5H). $^{13}C$ NMR (126 MHZ, DMSO-$d_6$) δ ppm: 80.6, 74.3, 59.7, 31.6, 25.9 (2C), 24.8, 24.6 (2C).

2-Methyl-N-prop-2-ynyl-propane-1-sulfonamide (106)

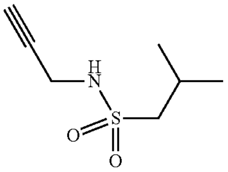

Compound 106 was synthesized according to the general procedure C, using propargylamine (135 µL, 2.11 mmol), 2-methylpropane-1-sulfonyl chloride (300 mg, 1.92 mmol) and N,N-diisopropylethylamine (667 µL, 3.83 mmol) in $CH_2Cl_2$ (10 mL) overnight. The crude product was purified by flash chromatography on silica gel (cHex to cHex/EtOAc: 4/6) affording compound 106 as yellow oil (271 mg, 79%). LC tr=not visible (254 nm), MS (ESI+): no ionization $[M+H]^+$; MS (ESI−): no ionization $[M-H]^-$. $^1H$ NMR (500 MHz, DMSO-$d_6$) δ ppm: 7.58 (t, J=5.9 Hz, 1H), 3.78 (dd, J=5.9 and 2.5 Hz, 2H), 3.30 (t, J=2.5 Hz, 1H), 2.97 (d, J=6.4 Hz, 2H), 2.12 (sep, J=6.8 Hz, 1H), 1.03-1.01 (m, 6H). $^{13}C$ NMR (126 MHz, DMSO-$d_6$) δ ppm: 80.5, 74.6, 59.6, 31.5, 24.2, 22.2 (2C).

1-(7,7-Dimethyl-2-oxo-norbornan-1-yl)-N-prop-2-ynyl-methanesulfonamide (94)

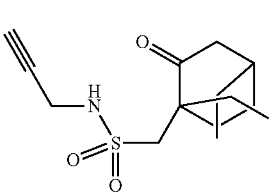 [SMILES: C#CCNS(=O)(=O)CC1(CC)CCC(CC)CC1=O]

Compound 94 was synthesized according to the general procedure C, using propargylamine (84.3 µL, 1.32 mmol), (7,7-dimethyl-2-oxo-norbornan-1-yl)methanesulfonyl chloride (300 mg, 1.2 mmol) and N,N-diisopropylethylamine (417 µL, 2.39 mmol) in $CH_2Cl_2$ (5 mL) overnight. Compound 94 was obtained as a white solid (210 mg, 64%) and used in the next step without further purifications. LC tr=3.59 min, MS (ESI+): m/z=270 $[M+H]^+$. $^1H$ NMR (500 MHz, DMSO-$d_6$) δ ppm: 7.57 (t, J=6.0 Hz, 1H), 3.84 (dd, J=6.0 and 2.5 Hz, 2H), 3.42 (d, J=14.9 Hz, 1H), 3.04 (d, J=14.9 Hz, 1H), 2.37-2.32 (m, 2H), 2.05 (t, J=4.5 Hz, 1H), 1.99-1.90 (m, 2H), 1.54-1.48 (m, 1H), 1.42-1.37 (m, 1H), 1.03 (s, 3H), 0.80 (s, 3H). $^{13}C$ NMR (126 MHz, DMSO-$d_6$) δ ppm: 215.0, 80.5, 75.0, 58.0, 49.2, 47.6, 42.1, 42.0, 31.9, 26.3, 24.6, 19.6, 19.4.

4-Iodo-N-methyl-N-prop-2-ynyl-benzenesulfonamide (115)

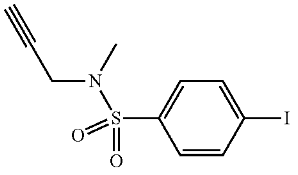

Compound 115 was synthesized according to the general procedure C, using N-methylpropargylamine (92 μL, 1.09 mmol), 4-iodobenzenesulfonyl chloride (300 mg, 0.99 mmol) and N,N-diisopropylethylamine (345 μL, 1.98 mmol) in $CH_2Cl_2$ (5 mL) overnight. Compound 94 was obtained as a white solid (327 mg, 97%) and used in the next step without further purifications. LC tr=4.55 min, MS (ESI+): m/z=336 $[M+H]^+$. $^1H$ NMR (500 MHz, DMSO-$d_6$) δ ppm: 8.01-7.99 (m, 2H), 7.57-7.54 (m, 2H), 4.03 (d, J=2.4 Hz, 2H), 3.16 (t, J=2.4 Hz, 1H), 2.73 (s, 3H). $^{13}C$ NMR (126 MHz, DMSO-$d_6$) δ ppm: 138.1 (2C), 136.3, 129.2 (2C), 101.6, 76.8, 76.6, 39.3, 34.1.

4-Iodo-N-prop-2-ynyl-benzamide (116)

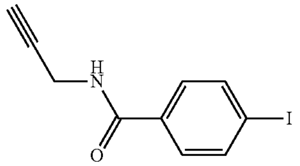

Propargylamine (79.3 μL, 1.24 mmol) and triethylamine (308 μL, 2.25 mmol) were solubilized in $CH_2Cl_2$ (5 mL). The reaction media was cooled at 0° C., and 4-iodobenzoyl chloride (300 mg, 1.13 mmol) was added. The mixture was allowed to reach room temperature and was stirred overnight. Then, it was diluted in water and washed twice with 0.25 M aq. HCl, with sat. aq. $NaHCO_3$ and brine. The organic layer was dried over $MgSO_4$, filtered and concentrated under reduced pressure affording compound 116 as an orange powder (159 mg, 49%). LC tr=3.71 min, MS (ESI+): m/z=286 $[M+H]^+$. $^1H$ NMR (500 MHz, DMSO-$d_6$) δ ppm: 9.01 (t, J=5.4 Hz, 1H), 7.87-7.85 (m, 2H), 7.64-7.62 (m, 2H), 4.04 (dd, J=5.4 and 2.4 Hz, 2H), 3.12 (t, J=2.4 Hz, 1H). $^{13}C$ NMR (126 MHz, DMSO-$d_6$) δ ppm: 165.3, 137.3 (2C), 133.2, 129.3 (2C), 99.2, 81.1, 73.0, 28.5.

4-Iodo-N-prop-2-ynyl-aniline (118)

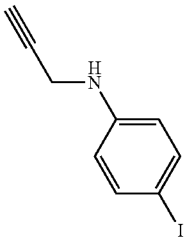

To a solution of 4-iodoaniline (300 mg, 1.37 mmol) in DMF (3 mL) were added $K_2CO_3$ (379 mg, 2.74 mmol) and propargylbromide (143 μL, 1.51 mmol). The resulting solution was stirred at room temperature for 48 h. After 48 h, the conversion was not complete and propargylbromide (195 μL, 2.05 mmol) was added and the mixture was stirred overnight at 60° C. The conversion was not significantly increased and the reaction was therefore stopped at 50% of conversion (LC-MS monitoring). The mixture was then diluted in water and extracted three times with ethyl acetate. Combined organic layers were dried over $MgSO_4$, filtered and concentrated under reduced pressure. Finally, the residue was purified through two successive flash chromatographies on silica gel (cHex to cHex/EtOAc: 6/4) and (cHex/$CH_2Cl_2$ to cHex/$CH_2Cl_2$: 7/3 to 5/5) affording compound 118 as brown oil (100 mg, 28%). LC tr=3.61 min, MS (ESI+): m/z=258 $[M+H]^+$. $^1H$ NMR (500 MHz, DMSO-$d_6$) b: 7.39-7.37 (m, 2H), 6.49-6.48 (m, 2H), 6.22 (t, J=6.1 Hz, 1H), 3.83 (dd, J=6.1 and 2.4 Hz, 2H), 3.08 (t, J=2.4 Hz, 1H). $^{13}C$ NMR (126 MHz, DMSO-$d_6$) δ: 147.5, 137.1 (2C), 115.5 (2C), 81.8, 77.4, 73.2, 31.9.

1-Chloro-4-prop-2-ynylsulfanyl-benzene (120)

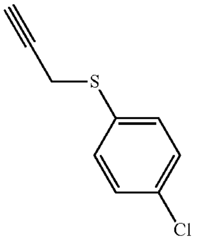

To a solution of 4-chlorobenzenethiol (300 mg, 2.07 mmol) in F (3 mL) were added $K_2CO_3$ (573 mg, 4.15 mmol) and propargylbromide (216 μL, 2.28 mmol). The resulting solution was heated at 60° C. and stirred overnight. The mixture was then diluted in water and extracted three times with ethyl acetate. Combined organic layers were dried over $MgSO_4$, filtered and concentrated under reduced pressure affording the desired product as a brown solid (352 mg, 92%). LC tr=4.81 min, MS (ESI+): m/z=no ionisation $[M+H]^+$, (ESI−): m/z=no ionisation $[M-H]^-$. $^1H$ NMR (500 MHz, DMSO-$d_6$) δ ppm: 7.41 (s, 4H), 3.87 (d, J=2.6 Hz, 2H), 3.16 (t, J=2.6 Hz, 1H). $^{13}C$ NMR (126 MHz, DMSO-$d_6$) δ ppm: 134.0, 131.0, 130.2 (2C), 128.9 (2C), 80.1, 74.0, 20.6.

1-Chloro-4-prop-2-ynoxy-benzene (119)

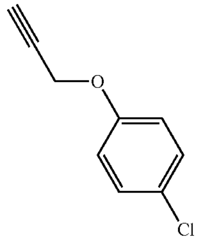

To a solution of 4-chlorophenol (300 mg, 2.33 mmol) in DMF (3 mL) were added $K_2CO_3$ (645 mg, 4.67 mmol) and propargylbromide (243 μL, 2.57 mmol). The resulting solution was heated at 60° C. and stirred overnight. The mixture was then diluted in water and extracted three times with ethyl acetate. Organic layers were combined and solvents were evaporated under reduced pressure and the residue was purified through flash chromatography on silica gel (cHex to cHex/EtOAc: 8/2) affording compound 119 as a brown solid (376 mg, 96%). LC tr=4.55 min, MS (ESI+): m/z=no ionisation $[M+H]^+$, (ESI−): m/z=no ionisation $[M-H]^-$. $^1H$ NMR (500 MHz, DMSO-$d_6$) δ ppm: 7.37-7.34 (m, 2H), 7.03-6.99 (m, 2H), 4.80 (d, J=2.4 Hz, 2H), 3.59 (t, J=2.3 Hz, 1H). $^{13}C$ NMR (126 MHz, DMSO-$d_6$) δ ppm: 156.0, 129.2 (2C), 125.0, 116.7 (2C), 78.9, 78.5, 55.7.

N-(2-Prop-2-ynoxyphenyl)acetamide (100)

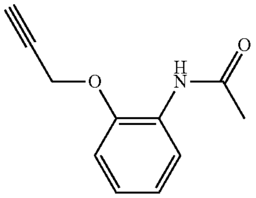

To a solution of N-(2-hydroxyphenyl) acetamide (150 mg, 0.99 mmol) in DMF (5 mL) were added $K_2CO_3$ (274 mg, 1.98 mmol) and propargylbromide (103 μL, 1.09 mmol). The resulting solution was heated at 60° C. and stirred overnight. The mixture was then diluted in water and extracted three times with ethyl acetate. Organic layers were combined and solvents were evaporated under reduced pressure affording compound 100 as a brown solid (182 mg, 96%). LC tr=3.03 min, MS (ESI+): m/z=190 $[M+H]^+$. $^1H$ NMR (500 MHz, DMSO-$d_6$) δ ppm: 9.13 (s, 1H), 7.91 (d, J=7.5 Hz, 1H), 7.12-7.11 (m, 1H), 7.06 (t, J=7.5 Hz, 1H), 6.93 (t, J=7.5 Hz, 1H), 4.86 (d, J=2.0 Hz, 2H), 3.60 (t, J=2.2 Hz, 1H), 2.08 (s, 3H). $^{13}C$ NMR (126 MHz, DMSO-$d_6$) δ ppm: 168.5, 147.6, 127.9, 124.1, 122.6, 121.0, 112.9, 79.2, 78.6, 56.0, 23.8.

1,1-Dioxo-2-prop-2-ynyl-1,2-benzothiazol-3-one (117)

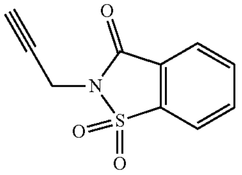

Saccharin (500 mg, 2.73 mmol) was dissolved in dry DMF (3 mL). Sodium carbonate (289 mg, 2.73 mmol) was added portion wise followed by propargyl bromide (441 μL, 80 wt % in toluene, 4.09 mmol). The reaction media was stirred overnight at 80° C. The mixture was then diluted in ethyl acetate and washed with brine. The organic layer was dried over $MgSO_4$, filtered and concentrated under reduced pressure affording compound 117 as a brown solid (548 mg, 89%). LC tr=3.47 min, MS (ESI+): m/z=222 $[M+H]^+$. $^1H$ NMR (500 MHz, DMSO-$d_6$) δ ppm: 8.34 (dt, J=7.7 and 0.8 Hz, 1H), 8.14 (dt, J=7.7 and 0.8 Hz, 1H), 8.07 (td, J=11.4 and 1.1 Hz, 1H), 8.01 (td, J=11.4 and 0.9 Hz, 1H), 4.58 (d, J=2.5 Hz, 2H), 3.40 (t, J=2.5 Hz, 1H). $^{13}C$ NMR (126 MHz, DMSO-$d_6$) δ ppm: 157.9, 136.9, 136.1, 135.4, 126.0, 125.3, 121.7, 77.0, 75.2, 27.5.

1-Chloro-4-prop-2-ynyl-benzene (121)

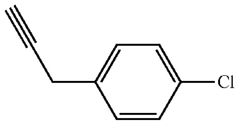

2-(4-chlorophenyl)acetaldehyde (500 mg, 3.23 mmol) and potassium carbonate (894 mg, 6.47 mmol) were mixed in anhydrous methanol (7 mL), followed by a dropwise addition of the Ohira-Bestmann reagent (647 μL, 4.31 mmol), and the reaction was stirred overnight at room temperature overnight. The mixture was then diluted in $CH_2Cl_2$ and washed with 5% aq. $NaHCO_3$. The organic layer was concentrated under reduced pressure and the residue was purified through flash silica gel column (cH to cH/EtOAc 9:1), affording compound 121 as yellow oil (169 mg, 32%). LC tr=5.14 min, MS (ESI+): m/z=no ionization $[M+H]^+$; MS (ESI−): m/z=no ionization $[M-H]^-$. $^1H$ NMR (500 MHz, DMSO-$d_6$) δ ppm: 7.30 (s, 4H), 3.59 (d, J=2.7 Hz, 2H), 2.21 (t, J=2.7 Hz, 1H). $^{13}C$ NMR (126 MHz, DMSO-$d_6$) δ ppm: 134.7, 132.7, 129.3 (2C), 128.8 (2C), 81.5, 71.0, 24.4.

1-Ethynyl-4-iodo-benzene (122)

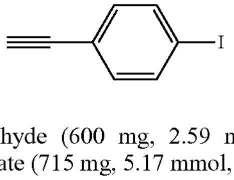

4-iodobenzaldehyde (600 mg, 2.59 mmol, 1 eq) and potassium carbonate (715 mg, 5.17 mmol, 2 eq) were mixed in anhydrous methanol (7.0 mL) followed by a dropwise addition of Ohira-Bestmann reagent (466 μL, 3.10 mmol, 1.2 eq). The resulting mixture was stirred overnight at room temperature. The mixture was then diluted with $CH_2Cl_2$ and washed with 5% aq. $NaHCO_3$. The organic layer was dried over $MgSO_4$, filtered and concentrated under reduced pressure. Finally, the residue was purified through flash silica gel column (cH to cH/EtOAc: 9:1) affording the desired product as a white solid (256 mg, 43%). LC tr=4.96 min, MS (ESI+): m/z=no ionization $[M+H]^+$; MS (ESI−): m/z=no ionization $[M-H]^-$. $^1H$ NMR (500 MHz, $CDCl_3$) δ ppm: 7.68-7.66 (m, 2H), 7.22-7.20 (m, 2H), 3.13 (s, 1H). $^{13}C$ NMR (126 MHz, $CDCl_3$) δ ppm: 137.6 (2C), 133.6 (2C), 121.6, 94.9, 82.7, 78.6.

N-[2-(4-Hydroxyphenyl)ethyl]pent-4-ynamide (109)

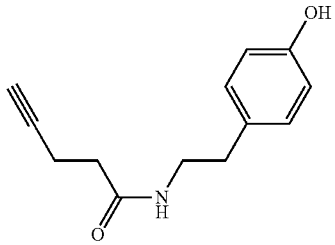 [SMILES: C#CCCC(=O)NCCc1ccc(O)cc1]

Pentynoic acid (100 mg, 1.02 mmol), tyramine (210.0 mg, 1.53 mmol, 1.5 eq) and HBTU (464 mg, 1.22 mmol, 1.2 eq) were put in solution in DMF (5.0 mL) and triethylamine (424 μL, 3.06 mmol, 3 eq), and the mixture was stirred overnight at room temperature. The resulting mixture was then diluted with water and extracted with EtOAc (three times). The organic layers were combined and solvents were evaporated in vacuo. The residue was then purified through flash silica gel column (cH/EtOAc: 9:1 to 5:5), affording compound 109 as a colorless oil (107 mg, 47%). LC tr=2.57 min, MS (ESI+): m/z=218 $[M+H]^+$. $^1H$ NMR (500 MHz, DMSO-$d_6$) δ ppm: 9.19 (s, 1H), 7.95 (t, J=5.5 Hz, 1H), 6.99-6.97 (m, 2H), 6.68-6.65 (m, 2H), 3.20-3.16 (m, 2H), 2.78 (t, J=2.6 Hz, 1H), 2.58-2.55 (m, 2H), 2.35-2.31 (m, 2H), 2.25-2.22 (m, 2H). $^{13}C$ NMR (126 MHz, DMSO-$d_6$) δ ppm: 170.1, 155.7, 129.6 (2C), 129.5, 115.1 (2C), 83.9, 71.4, 40.7, 34.4, 34.2, 14.3.

2-Ethoxycarbonyl-4-methyl-pentanoic acid (80)

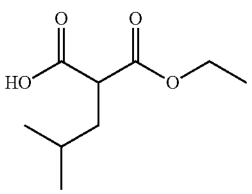

Compound 80 was synthesized according to the general procedure F, using diethylmalonate (1000 mg, 4.62 mmol) and NaOH (222 mg, 5.55 mmol) in $EtOH/H_2O$ (10 mL, 8:2 v/v) overnight. Compound 80 was obtained as colorless oil (711 mg, 80%) and was used in the next step without further purification. LC tr=2.10 min, MS (ESI+): m/z=189 $[M+H]^+$. $^1H$ NMR (MeOD-$d_4$) δ ppm: 4.18 (q, J=7.1 Hz, 2H), 3.41 (t, J=7.6 Hz, 1H), 1.77-1.72 (m, 2H), 1.64-1.50 (m, 1H), 1.26 (t, J=7.1 Hz, 3H), 0.93 (d, J=6.5 Hz, 6H). $^{13}C$ NMR (MeOD-$d_4$) δ ppm: 173.0, 171.6, 62.3, 51.4, 38.8, 27.4, 22.7, 22.5, 14.4.

2-Methoxycarbonyl-3-methyl-butanoic acid (174-a)

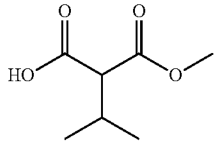

Compound 174-a was synthesized according to the general procedure F, using dimethylmalonate (745 mg, 4.28 mmol) and KOH (240 mg, 4.28 mmol) in $MeOH/H_2O$ (11 mL, 10:1 v/v) overnight. Compound 174-a was obtained as colorless oil (711 mg, 80%) and was used in the next step without further purification. LC tr=2.71 min, MS (ESI+): m/z=161 $[M+H]^+$. $^1H$ NMR (500 MHz, DMSO-$d_6$) δ ppm: 12.85 (s, 1H), 3.63 (s, 3H), 3.11 (d, J=8.6 Hz, 1H), 2.23-2.14 (m, 1H), 0.93 (d, J=6.7 Hz, 3H), 0.91 (d, J=6.7 Hz, 3H). $^{13}C$ NMR (126 MHz, DMSO-$d_6$) δ ppm: 169.7, 169.2, 58.2, 51.9, 28.0, 20.1, 20.0.

2-(Cyclopropylmethyl)-3-ethoxy-3-oxo-propanoic acid (175-a)

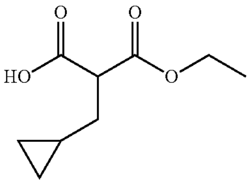

Compound 175-a was synthesized according to the general procedure F, using dimethylmalonate (550 mg, 2.57 mmol) and KOH (144 mg, 2.57 mmol) in $EtOH/H_2O$ (9 mL, 8:1 v/v) overnight. Compound 175-a was obtained as colorless oil (347 mg, 71%) and was used in the next step without further purification. LC tr=not visible, MS (ESI+): m/z=187 $[M+H]^+$. $^1H$ NMR (500 MHz, DMSO-$d_6$) δ ppm: 12.80 (br s, 1H), 4.11 (q, J=7.1 Hz, 2H), 3.40-3.35 (m, 1H), 1.69-1.60 (m, 2H), 1.18 (t, J=7.1 Hz, 3H), 0.71-0.63 (m, 1H), 0.39-0.37 (m, 2H), 0.09-0.03 (m, 2H). $^{13}C$ NMR (126 MHz, DMSO-$d_6$) δ ppm: 170.4, 169.5, 60.6, 51.9, 33.2, 14.0, 8.7, 4.4, 4.2.

2-Benzyl-3-ethoxy-3-oxo-propanoic acid (173-a)

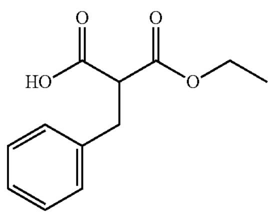 [SMILES: CCOC(=O)C(Cc1ccccc1)C(=O)O]

Compound 173-a was synthesized according to the general procedure F, using dimethylmalonate (1070 mg, 4.28 mmol) and KOH (240 mg, 4.28 mmol) in $EtOH/H_2O$ (11 mL, 10:1 v/v) overnight. Compound 173-a was obtained as colorless oil (694 mg, 72%) and was used in the next step without further purification. LC tr=3.72 min, MS (ESI+): m/z=no ionization $[M+H]^+$. $^1H$ NMR (500 MHz, $CDCl_3$) δ ppm: 10.23 (br s, 1H), 7.36-7.31 (m, 2H), 7.30-7.26 (m, 3H), 4.22 (q, J=7.1 Hz, 2H), 3.76 (t, J=7.7 Hz, 1H), 3.30 (dd, J=7.7 and 2.8 Hz, 2H), 1.26 (t, J=7.1 Hz, 3H). $^{13}C$ NMR (126 MHz, $CDCl_3$) δ ppm: 174.3, 168.9, 137.4, 128.9 (2C), 128.7 (2C), 127.1, 62.0, 53.6, 34.9, 14.1.

Ethyl 2-[[4-[(tert-butoxycarbonylamino)methyl] phenyl]carbamoyl]-4-methyl-pentanoate (81)

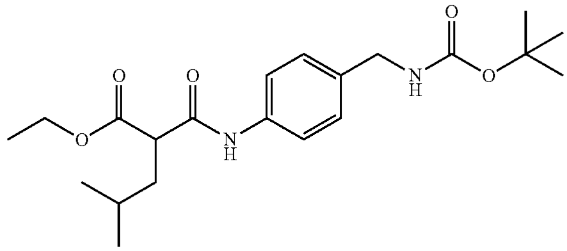 [SMILES: CCOC(=O)C(CC(C)C)C(=O)Nc1ccc(CNC(=O)OC(C)(C)C)cc1]

Compound 81 was synthesized according to the general procedure B, using carboxylic acid 80 (450 mg, 2.39 mmol), tert-butyl N-[(4-aminophenyl)methyl]carbamate (638 mg, 2.87 mmol), HBTU (1540 mg, 4.06 mmol) and trimethylamine (981 μL, 7.17 mmol) in DMF (8 mL) overnight. The crude product was purified by flash chromatography on silica gel (cHex/EtOAc: 9/1 to 7/3) affording compound 81 as an off-white solid (456 mg, 47%). LC tr=3.03 min, MS (ESI−): m/z=391 $[M-H]^-$. $^1H$ NMR (DMSO-$d_6$) δ ppm: 10.18 (s, 1H), 7.52-7.49 (m, 2H), 7.33 (t, J=6.0 Hz, 1H), 7.18-7.15 (m, 2H), 4.15-4.02 (m, 4H), 3.56 (dd, J=8.6 Hz and 6.3 Hz, 1H), 1.80-1.60 (m, 2H), 1.57-1.45 (m, 1H), 1.39 (s, 9H), 1.16 (t, J=7.1 Hz, 3H), 0.90 (d, J=6.6 Hz, 3H), 0.87 (d, J=6.6 Hz, 3H). $^{13}C$ NMR (DMSO-$d_6$) δ ppm: 169.8, 166.9, 155.7, 137.4, 135.4, 127.4 (2C), 119.2 (2C), 77.7, 60.6, 50.9, 43.0, 37.4, 28.2 (3C), 25.6, 22.6, 21.9, 14.0.

Ethyl 2-[[3-[(tert-butoxycarbonylamino)methyl] phenyl]carbamoyl]-4-methyl-pentanoate (110)

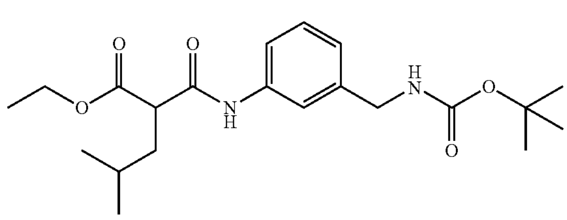 [SMILES: CCOC(=O)C(CC(C)C)C(=O)Nc1cccc(CNC(=O)OC(C)(C)C)c1]

Compound 110 was synthesized according to the general procedure B, using carboxylic acid 80 (320 mg, 1.7 mmol), tert-butyl N-[(3-aminophenyl)methyl]carbamate (416 mg, 1.87 mmol), HBTU (967 mg, 2.55 mmol) and trimethylamine (697 μL, 5.10 mmol) in DMF (5 mL) overnight. The crude product was purified by flash chromatography on silica gel (cHex/EtOAc: 9/1 to 7/3) affording compound 110 as a yellowish solid (507 mg, 74%). LC tr=4.77 min, MS (ESI+): m/z=393 $[M+H]^+$, 337 $[M\text{-tBu}]^+$. $^1H$ NMR (500 MHz, DMSO-$d_6$) δ ppm: 10.24 (s, 1H), 7.47-7.45 (m, 2H), 7.42 (t, J=6.1 Hz, 1H), 7.24 (t, J=8.0 Hz, 1H), 6.93 (d, J=7.6 Hz, 1H), 4.13-4.04 (m, 4H), 3.57 (dd, J=8.9 and 6.0 Hz, 1H), 1.78-1.72 (m, 1H), 1.66-1.60 (m, 1H), 1.48 (sep, J=6.7 Hz, 1H), 1.39 (s, 9H), 1.18-1.14 (m, 3H), 0.89 (d, J=6.6 Hz, 3H), 0.87 (d, J=6.6 Hz, 3H). $^{13}C$ NMR (126 MHz, DMSO-$d_6$) δ ppm: 169.9, 167.1, 155.8, 141.0, 138.8, 128.7, 122.3, 117.8, 117.7, 77.9, 60.7, 50.9, 43.4, 37.5, 28.3 (3C), 25.7, 22.8, 21.9, 14.1.

[4-[(2-Ethoxycarbonyl-4-methyl-pentanoyl)amino] phenyl]methylammonium chloride (82)

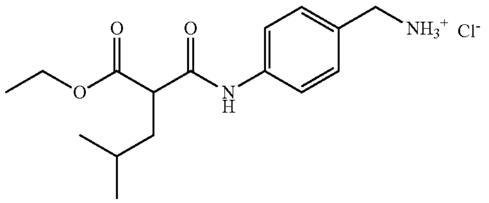 [SMILES: CCOC(=O)C(CC(C)C)C(=O)Nc1ccc(C[NH3+])cc1 ; [Cl-]]

Compound 82 was synthesized according to the general procedure G, using the Boc-protected intermediate 81 (440 mg, 1.12 mmol), 4 N HCl in dioxane (5 mL) in a mixture $CH_2Cl_2$/EtOH (10 mL, 5:5 v/v) overnight. Compound 82 was obtained as yellow oil (369 mg, quant. yield) and was used in the next step without further purification. LC tr=2.15 min, MS (ESI−): m/z=291 $[M-H]^-$. $^1H$ NMR (DMSO-$d_6$) δ ppm: 10.55 (s, 1H), 8.44 (br s, 3H), 7.65-7.60 (m, 2H), 7.44-7.41 (m, 2H), 4.13-4.04 (m, 2H), 3.96-3.91 (m, 2H), 3.68-3.63 (m, 1H), 1.79-1.61 (m, 2H), 1.50 (sep, J=6.7 Hz, 1H), 1.15 (t, J=7.1 Hz, 3H), 0.89 (d, J=6.7 Hz, 3H), 0.87 (d, J=6.7 Hz, 3H). $^{13}C$ NMR (DMSO-$d_6$) δ ppm: 169.8, 167.4, 139.1, 129.6 (2C), 129.0, 119.2 (2C), 60.6, 50.9, 41.8, 37.5, 25.7, 22.7, 22.1, 14.1.

[3-[(2-Ethoxycarbonyl-4-methyl-pentanoyl)amino] phenyl]methylammonium chloride (111)

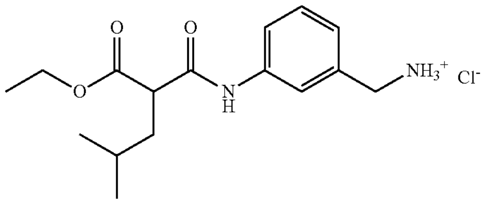 [SMILES: CCOC(=O)C(CC(C)C)C(=O)Nc1cccc(C[NH3+])c1 ; [Cl-]]

Compound 111 was synthesized according to the general procedure G, using the Boc-protected intermediate 110 (495 mg, 1.26 mmol), 4 N HCl in dioxane (7 mL) in a mixture $CH_2Cl_2$/EtOH (14 mL, 7:7 v/v) overnight. Compound 111 was obtained as yellow oil (415 mg, quant. yield) and was used in the next step without further purification. LC tr=2.82 min, MS (ESI+): m/z=293 $[M+H]^+$, 585 $[2M+H]^+$. $^1H$ NMR (500 MHz, DMSO-$d_6$) δ ppm: 10.54 (s, 1H), 8.39 (br s, 3H), 7.79-7.78 (m, 1H), 7.54-7.53 (m, 1H), 7.36 (t, J=7.9 Hz, 1H), 7.21-7.20 (m, 1H), 4.13-4.05 (m, 2H), 3.72-3.65 (m, 2H), 3.51-3.46 (m, 1H), 1.79-1.73 (m, 1H), 1.67-1.61 (m, 1H), 1.49 (sep, J=6.6 Hz, 1H), 1.16 (t, J=7.1 Hz, 3H), 0.90

(d, J=6.6 Hz, 3H), 0.88 (d, J=6.6 Hz, 3H). $^{13}C$ NMR (126 MHz, DMSO-$d_6$) δ ppm: 169.9, 167.4, 139.2, 134.7, 129.2, 124.2, 119.9, 119.4, 60.7, 53.6, 50.9, 37.5, 25.7, 22.9, 22.0, 14.1.

Ethyl 2-[[4-(azidomethyl)phenyl]carbamoyl]-4-methyl-pentanoate (83)

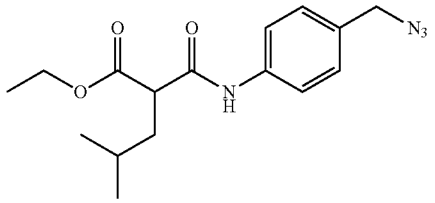 [SMILES: CCOC(=O)C(CC(C)C)C(=O)Nc1ccc(CN=[N+]=[N-])cc1]

Compound 83 was synthesized according to the general procedure A, using amine 82 (350 mg, 0.93 mmol), $ZnCl_2$ (7.6 mg, 0.05 mmol), $K_2CO_3$ (512 mg, 3.7 mmol), anhydrous N,N-diisopropylethylamine (177 μL, 1.02 mmol) and diazo transfer reagent (301 mg, 1.11 mmol) in anhydrous MeOH (5 mL) overnight. The crude product was purified by flash chromatography on silica gel (cHex to cHex/EtOAc: 8/2), affording compound 84 as a yellowish solid (176 mg, 58%). Trans esterification was also observed, leading to the formation of the methyl ester analog (87). LC tr=3.02 min, MS (ESI−): m/z=317 $[M-H]^-$. $^1H$ NMR (300 MHz, $CDCl_3$+TMS) δ ppm: 8.75 (s, 1H), 7.58-7.56 (m, 2H), 7.28-7.24 (m, 2H), 4.28 (br s, 2H), 4.26-4.19 (m, 2H), 3.46 (t, J=7.7 Hz, 1H), 1.90-1.85 (m, 2H), 1.64 (sep, J=6.7 Hz, 1H), 1.30 (t, J=7.1 Hz, 3H), 0.95 (d, J=6.7 Hz, 6H). $^{13}C$ NMR (75 MHz, $CDCl_3$+TMS) δ ppm: 172.8, 166.9, 137.8, 131.3, 129.0 (2C), 120.2 (2C), 61.8, 54.3, 52.4, 40.5, 26.4, 22.4, 22.1, 14.1.

Ethyl 2-[[3-(azidomethyl)phenyl]carbamoyl]-4-methyl-pentanoate (112)

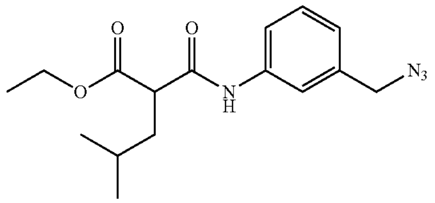 [SMILES: CCOC(=O)C(CC(C)C)C(=O)Nc1cccc(CN=[N+]=[N-])c1]

Compound 112 was synthesized according to the general procedure A, using amine 111 (405 mg, 1.07 mmol), $ZnCl_2$ (8.8 mg, 0.06 mmol), $K_2CO_3$ (296 mg, 2.14 mmol), anhydrous N,N-diisopropylethylamine (392 μL, 2.25 mmol) and diazo transfer reagent (270 mg, 1.29 mmol) in anhydrous MeOH (5 mL) overnight. The crude product was purified by flash chromatography on silica gel (cHex to cHex/EtOAc: 8/2) affording compound 112 as white crystals (121 mg, 31%). LC tr=4.75 min, MS (ESI+): m/z=319 $[M+H]^+$. $^1H$ NMR (500 MHz, DMSO-$d_6$) δ ppm: 10.31 (s, 1H), 7.65-7.64 (m, 1H), 7.55-7.53 (m, 1H), 7.34 (t, J=7.8 Hz, 1H), 7.07-7.06 (m, 1H), 4.44 (s, 2H), 4.16-4.06 (m, 2H), 3.58 (dd, J=8.8 and 6.2 Hz, 1H), 1.78-1.74 (m, 1H), 1.69-1.63 (m, 1H), 1.50 (sep, J=6.7 Hz, 1H), 1.16 (t, J=7.0 Hz, 3H), 0.90 (d, J=6.7 Hz, 3H), 0.88 (d, J=6.7 Hz, 3H). $^{13}C$ NMR (126

MHz, DMSO-$d_6$) δ ppm: 169.7, 167.2, 139.2, 136.4, 129.2, 123.5, 119.0, 118.9, 60.7, 53.6, 51.0, 37.4, 25.6, 22.7, 21.9, 14.0.

Tert-butyl N-[4-(azidomethyl)phenyl]carbamate (170)

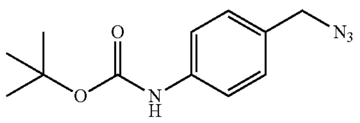 [SMILES: CC(C)(C)OC(=O)Nc1ccc(CN=[N+]=[N-])cc1]

Compound 170 was synthesized according to the general procedure A, using tert-butyl N-[4-(aminomethyl)phenyl] carbamate (500 mg, 2.25 mmol), $ZnCl_2$ (18.4 mg, 0.14 mmol), $K_2CO_3$ (1240 mg, 9.0 mmol), anhydrous N,N-diisopropylethylamine (240 μL, 2.47 mmol) and diazo transfer reagent (566 mg, 2.7 mmol) in anhydrous MeOH (5 mL) overnight. Compound 170 was obtained as orange oil (558 mg, quant. yield) and was used in the next step without further purification. LC tr=4.72 min, MS (ESI+): m/z=no ionization $[M+H]^+$. $^1H$ NMR (500 MHz, DMSO-$d_6$) δ ppm: 9.42 (s, 1H), 7.48-7.45 (m, 2H), 7.26-7.24 (m, 2H), 4.33 (s, 2H), 1.47 (s, 9H). $^{13}C$ NMR (126 MHz, DMSO-$d_6$) δ ppm: 152.7, 139.5, 129.1 (3C), 128.8, 118.2, 79.1, 53.3, 28.1 (3C).

[4-(Azidomethyl)phenyl]ammonium;chloride (171)

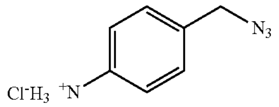 [SMILES: [N-]=[N+]=NCc1ccc([NH3+])cc1 ; "Cl-H3"]

Compound 171 was synthesized according to the general procedure G, using the Boc-protected intermediate 170 (550 mg, 2.22 mmol), 4 N HCl in dioxane (10 mL) in a mixture $CH_2Cl_2$/EtOH (20 mL, 10:10 v/v) overnight. Compound 171 was obtained as an orange solid (409 mg, quant. yield) and was used in the next step without further purification. LC tr=1.40 min, MS (ESI+): m/z=149 $[M+H]^+$. $^1H$ NMR (500 MHz, DMSO-$d_6$) δ ppm: 9.88 (br s, 3H), 7.45-7.43 (m, 2H), 7.33-7.32 (m, 2H), 4.46 (s, 2H).

Methyl 2-[[4-(azidomethyl)phenyl]carbamoyl]-3-methyl-butanoate (174)

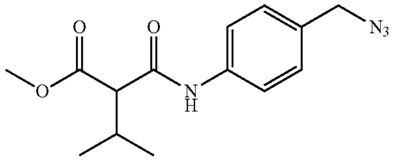 [SMILES: COC(=O)C(C(=O)Nc1ccc(CN=[N+]=[N-])cc1)C(C)C]

Compound 174 was synthesized according to the general procedure B, using carboxylic acid 174-a (300 mg, 1.87 mmol), aniline 171 (415 mg, 2.27 mmol), HBTU (1070 mg, 2.81 mmol) and trimethylamine (1020 μL, 7.49 mmol) in DMF (5 mL) overnight. The crude product was purified by flash chromatography on silica gel (cHex to cHex/EtOAc: 6/4) affording compound 174 as a white solid (203 mg, 37%). LC tr=4.18 min, MS (ESI+): m/z=291 $[M+H]^+$. $^1H$ NMR (500 MHz, DMSO-$d_6$) δ ppm: 10.28 (s, 1H), 7.62-7.60 (m, 2H), 7.33-7.31 (m, 2H), 4.38 (s, 2H), 3.64 (s, 3H), 3.24 (d, J=9.7 Hz, 1H), 2.36-2.28 (m, 1H), 0.95 (d, J=6.7 Hz, 3H), 0.92 (d, J=6.7 Hz, 3H). $^{13}C$ NMR (126 MHz, DMSO-$d_6$) δ ppm: 169.4, 166.3, 138.6, 130.6, 129.2 (2C), 119.4 (2C), 60.0, 53.2, 51.9, 28.4, 20.6, 19.8.

Ethyl 3-[4-(azidomethyl)anilino]-2-(cyclopropylmethyl)-3-oxo-propanoate (175)

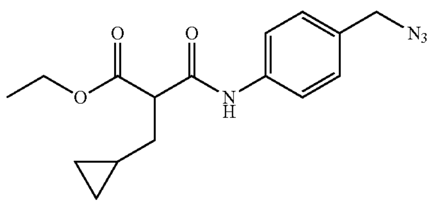 [SMILES: CCOC(=O)C(CC1CC1)C(=O)Nc1ccc(CN=[N+]=[N-])cc1]

Compound 175 was synthesized according to the general procedure B, using carboxylic acid 175-a (340 mg, 1.83 mmol), aniline 171 (405 mg, 2.19 mmol), HBTU (1040 mg, 2.74 mmol) and trimethylamine (1250 μL, 9.13 mmol) in DMF (5 mL) overnight. The crude product was purified by flash chromatography on silica gel (cHex to cHex/EtOAc: 5/5) affording compound 175 as a pale yellow solid (277 mg, 43%). LC tr=4.49 min, MS (ESI+): m/z=317 $[M+H]^+$. $^1H$ NMR (500 MHz, DMSO-$d_6$) δ ppm: 10.30 (s, 1H), 7.62-7.61 (m, 2H), 7.33-7.31 (m, 2H), 4.38 (s, 2H), 4.12-4.09 (m, 2H), 3.59 (dd, J=8.6 and 6.8 Hz, 1H), 1.81-1.63 (m, 2H), 1.17 (t, J=7.1 Hz, 3H), 0.74-0.65 (m, 1H), 0.44-0.34 (m, 2H), 0.11-0.04 (m, 2H). $^{13}C$ NMR (126 MHz, DMSO-$d_6$) δ ppm: 169.5, 167.2, 138.8, 130.5, 129.2 (2C), 119.4 (2C), 60.6, 53.2, 53.2, 33.5, 14.0, 8.8, 4.4, 4.3.

Ethyl 3-[4-(azidomethyl)anilino]-2-benzyl-3-oxo-propanoate (173)

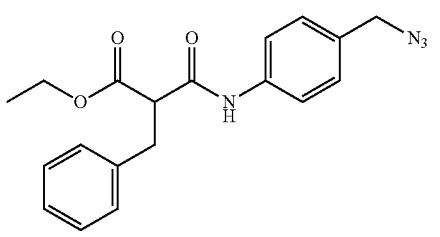 [SMILES: CCOC(=O)C(Cc1ccccc1)C(=O)Nc1ccc(CN=[N+]=[N-])cc1]

Compound 173 was synthesized according to the general procedure B, using carboxylic acid 173-a (300 mg, 1.35 mmol), aniline 171 (299 mg, 1.62 mmol), HBTU (768 mg, 2.02 mmol) and trimethylamine (738 μL, 5.4 mmol) in DMF (3 mL) overnight. The crude product was purified by flash chromatography on silica gel (cHex to cHex/EtOAc: 7/3) affording compound 173 as a white solid (152 mg, 31%). LC tr=4.69 min, MS (ESI+): m/z=353 $[M+H]^+$. $^1H$ NMR (500 MHz, DMSO-$d_6$) δ ppm: 10.25 (s, 1H), 7.54-7.53 (m, 2H), 7.30-7.29 (m, 2H), 7.26-7.15 (m, 5H), 4.36 (s, 2H), 4.11-4.04 (m, 2H), 3.84 (dd, J=8.5 and 6.8 Hz, 1H), 3.14-3.12 (m, 2H), 1.13 (t, J=7.1 Hz, 3H). $^{13}C$ NMR (126 MHz, DMSO-$d_6$) δ ppm: 169.0, 166.4, 138.5, 138.4, 130.6, 129.1 (2C), 128.8 (2C), 128.3 (2C), 126.4, 119.4 (2C), 60.8, 54.3, 53.2, 34.2, 14.0.

N-[4-(Azidomethyl)phenyl]-2-(hydroxycarbamoyl)-4-methyl-pentanamide (Z9)

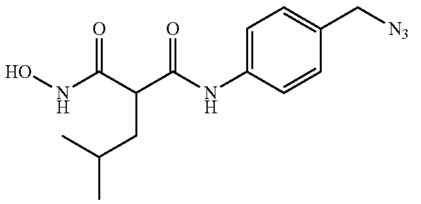 [SMILES: CC(C)CC(C(=O)NO)C(=O)Nc1ccc(CN=[N+]=[N-])cc1]

Compound Z9 was synthesized according to the general procedure D, using ester 83 (176 mg, 0.55 mmol), KCN (7.13 mg, 0.11 mmol) and aq. $NH_2OH$ (2.5 mL, 50% w/w in water) in MeOH (2.5 mL) overnight. The crude product was purified by flash chromatography on silica gel ($CH_2Cl_2$ to $CH_2Cl_2$/MeOH: 95/5) affording compound Z9 as a white solid after lyophilization (65 mg, 38%).

Purity: 100%, LC tr=2.35 min, MS (ESI−): m/z=304 $[M-H]^-$. $^1H$ NMR (300 MHz, DMSO-$d_6$) δ ppm: 10.52 (s, 1H), 9.82 (s, 1H), 8.97 (s, 1H), 7.62-7.59 (m, 2H), 7.32-7.30 (m, 2H), 4.37 (s, 2H), 3.22 (t, J=7.6 Hz, 1H), 1.69 (t, J=7.3 Hz, 2H), 1.49 (sep, J=6.7 Hz, 1H), 0.89 (d, J=2.0 Hz, 3H), 0.87 (d, J=2.0 Hz, 3H). $^{13}C$ NMR (75 MHz, DMSO-$d_6$) δ ppm: 167.8, 166.3, 138.7, 130.4, 129.1 (2C), 119.5 (2C), 53.2, 50.0, 38.0, 25.7, 22.4, 22.3.

N-[4-(Azidomethyl)phenyl]-2-(hydroxycarbamoyl)-3-methyl-butanamide (180)

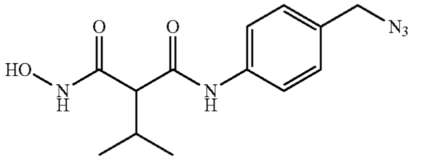 [SMILES: CC(C)C(C(=O)NO)C(=O)Nc1ccc(CN=[N+]=[N-])cc1]

Compound 180 was synthesized according to the general procedure D, using ester 174 (100 mg, 0.34 mmol), KCN (4.44 mg, 0.07 mmol) and aq. $NH_2OH$ (2.5 mL, 50% w/w in water) in MeOH (2.5 mL) overnight. The crude product was purified by flash chromatography on silica gel ($CH_2Cl_2$ to $CH_2Cl_2$/MeOH: 95/5) affording compound 180 as a white solid after lyophilization (43 mg, 43%). LC tr=3.24 min, MS (ESI+): m/z=292 $[M+H]^+$. $^1H$ NMR (500 MHz, DMSO-$d_6$) δ ppm: 10.55 (s, 1H), 9.78 (s, 1H), 9.02 (s, 1H), 7.62-7.60 (m, 2H), 7.32-7.30 (m, 2H), 4.37 (s, 2H), 2.73 (d, J=10.5 Hz, 1H), 2.40-2.33 (m, 1H), 0.90 (d, J=6.6 Hz, 3H), 0.89 (d, J=6.6 Hz, 3H). $^{13}C$ NMR (126 MHz, DMSO-$d_6$) δ ppm: 167.3, 165.9, 138.6, 130.5, 129.1 (2C), 119.6 (2C), 59.7, 53.2, 29.7, 20.4, 20.3.

N-[4-(Azidomethyl)phenyl]-2-(cyclopropylmethyl)-3-(hydroxyamino)-3-oxo-propanamide (181)

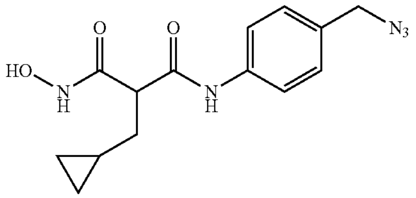 [SMILES: [N-]=[N+]=NCc1ccc(NC(=O)C(CC2CC2)C(=O)NO)cc1]

Compound 181 was synthesized according to the general procedure D, using ester 175 (135 mg, 0.42 mmol), KCN (5.5 mg, 0.08 mmol) and aq. $NH_2OH$ (3.2 mL, 50% w/w in water) in MeOH (3.2 mL) overnight. The crude product was purified by flash chromatography on silica gel ($CH_2Cl_2$ to $CH_2Cl_2$/MeOH: 95/5) affording compound 181 as a white solid after lyophilization (58 mg, 44%). LC tr=3.41 min, MS (ESI+): m/z=304 $[M+H]^+$. $^1H$ NMR (500 MHz, DMSO-$d_6$) δ ppm: 10.51 (br s, 1H), 9.86 (s, 1H), 8.96 (s, 1H), 7.62-7.60 (m, 2H), 7.32-7.30 (m, 2H), 4.37 (s, 2H), 3.23 (t, J=7.5 Hz, 1H), 1.72-1.69 (m, 2H), 0.68-0.61 (m, 1H), 0.40-0.34 (m, 2H), 0.09-0.08 (m, 2H). $^{13}C$ NMR (126 MHz, DMSO-$d_6$) δ ppm: 167.8, 166.2, 138.8, 130.3, 129.1 (2C), 119.4 (2C), 53.3, 52.0, 34.1, 9.0, 4.3, 4.3.

Methyl 2-[[4-[[4-[[(4-iodophenyl)sulfonylamino]methyl]triazol-1-yl]methyl]phenyl]carbamoyl]-4-methyl-pentanoate (88)

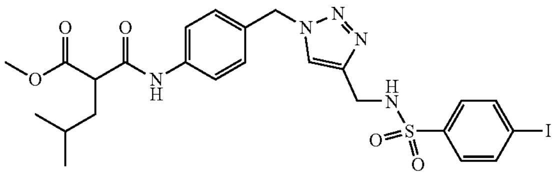 [SMILES: COC(=O)C(CC(C)C)C(=O)Nc1ccc(Cn2cc(CNS(=O)(=O)c3ccc(I)cc3)nn2)cc1]

Compound 88 was synthesized according to the general procedure E, using azide 87 (100 mg, 0.33 mmol), alkyne 93 (106 mg, 0.33 mmol), copper (II) sulfate pentahydrate (16.4 mg, 0.07 mmol) and sodium ascorbate (32.5 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 88 as a white powder (119 mg, 51%). LC tr=4.48 min, MS (ESI+): m/z=626 $[M+H]^+$. $^1H$ NMR (500 MHz, DMSO-$d_6$) δ ppm: 10.32 (s, 1H), 8.19 (t, J=5.9 Hz, 1H), 7.93-7.91 (m, 2H), 7.85 (s, 1H), 7.59-7.57 (m, 2H), 7.51-7.50 (m, 2H), 7.27-7.25 (m, 2H), 5.45 (s, 2H), 4.03 (d, J=5.9 Hz, 2H), 3.63 (s, 3H), 3.58 (dd, J=8.9 and 6.1 Hz, 1H), 1.78-1.73 (m, 1H), 1.68-1.62 (m, 1H), 1.48 (sep, J=6.6 Hz, 1H), 0.89 (d, J=6.6 Hz, 3H), 0.87 (d, J=6.6 Hz, 3H). $^{13}C$ NMR (126 MHz, DMSO-$d_6$) δ ppm: 170.2, 167.1, 143.4, 140.0, 138.7, 138.0 (2C), 130.9, 128.8 (2C), 128.3 (2C), 123.2, 119.4 (2C), 100.4, 52.4, 52.1, 50.8, 38.0, 37.4, 25.6, 22.7, 21.9.

Methyl 2-[[4-[[4-[[(7,7-dimethyl-2-oxo-norbornan-1-yl)methylsulfonylamino]methyl]triazol-1-yl]methyl]phenyl]carbamoyl]-4-methyl-pentanoate (89)

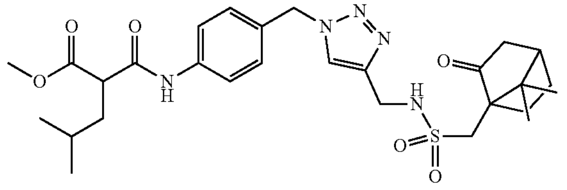

Compound 89 was synthesized according to the general procedure E, using azide 87 (100 mg, 0.33 mmol), alkyne 94 (88.5 mg, 0.33 mmol), copper (II) sulfate pentahydrate (16.4 mg, 0.07 mmol) and sodium ascorbate (32.5 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 89 as colorless oil (137 mg, 64%). LC tr=4.29 min, MS (ESI−): m/z=572 $[M-H]^-$. $^1H$ NMR (500 MHz, DMSO-$d_6$) δ ppm: 10.31 (s, 1H), 8.01 (s, 1H), 7.58-7.56 (m, 2H), 7.29-7.28 (m, 2H), 5.52 (s, 2H), 4.26-4.24 (m, 2H), 3.62 (s, 3H), 3.58 (dd, J=8.9 and 6.0 Hz, 1H), 3.21 (d, J=14.9 Hz, 1H), 3.17 (d, J=5.2 Hz, 1H), 2.84 (d, J=14.9 Hz, 1H), 2.32-2.27 (m, 2H), 2.01 (t, J=4.5 Hz, 1H), 1.89 (d, J=18.3 Hz, 2H), 1.78-1.73 (m, 1H), 1.67-1.62 (m, 1H), 1.50-1.44 (m, 2H), 1.38-1.33 (m, 1H), 0.95 (s, 3H), 0.88 (d, J=6.6 Hz, 3H), 0.87 (d, J=6.6 Hz, 3H), 0.70 (s, 3H). $^{13}C$ NMR (126 MHz, DMSO-$d_6$) δ ppm: 214.6, 170.2, 167.1, 144.6, 138.7, 131.1, 128.8 (2C), 123.2, 119.4 (2C), 57.9, 52.4, 52.1, 50.8, 48.7, 47.6, 42.0, 41.9, 38.0, 37.4, 26.3, 25.6, 24.5, 22.7, 21.9, 19.4, 19.2.

Methyl 4-methyl-2-[[4-[[4-[[(4-phenylphenyl)sulfonylamino]methyl]triazol-1-yl]methyl]phenyl]carbamoyl]pentanoate (90)

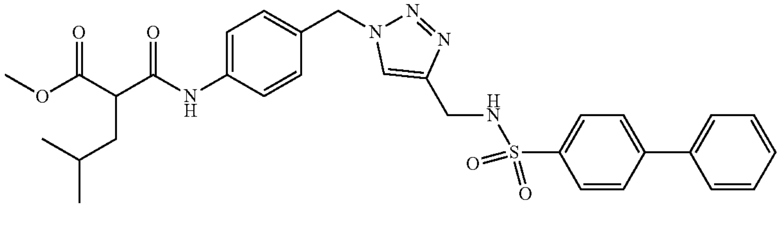 [SMILES: COC(=O)C(CC(C)C)C(=O)Nc1ccc(Cn2cc(CNS(=O)(=O)c3ccc(-c4ccccc4)cc3)nn2)cc1]

Compound 90 was synthesized according to the general procedure E, using azide 87 (100 mg, 0.33 mmol), alkyne 95 (89.2 mg, 0.33 mmol), copper (II) sulfate pentahydrate (16.4 mg, 0.07 mmol) and sodium ascorbate (32.5 mg, 0.16 mmol)

in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 90 as a greenwish powder (139 mg, 62%). LC tr=4.69 min, MS (ESI−): m/z=574 $[M-H]^-$. $^1H$ NMR (500 MHz, DMSO-$d_6$) δ ppm: 10.31 (s, 1H), 8.15 (t, J=5.9 Hz, 1H), 7.89 (s, 1H), 7.84 (s, 4H), 7.74-7.72 (m, 2H), 7.57-7.55 (m, 2H), 7.53-7.50 (m, 2H), 7.46-7.43 (m, 1H), 7.26-7.24 (m, 2H), 5.45 (s, 2H), 4.06 (d, J=5.9 Hz, 2H), 3.62 (s, 3H), 3.58 (dd, J=8.9 and 6.0 Hz, 1H), 1.78-1.72 (m, 1H), 1.68-1.62 (m, 1H), 1.48 (sep, J=6.7 Hz, 1H), 0.88 (d, J=6.7 Hz, 3H), 0.87 (d, J=6.7 Hz, 3H). $^{13}C$ NMR (126 MHz, DMSO-$d_6$) δ ppm: 170.1, 167.1, 143.9, 143.7, 139.1, 138.7, 138.5, 131.0, 129.1 (2C), 128.8 (2C), 128.5, 127.3 (2C), 127.2 (2C), 127.1 (2C), 123.2, 119.4 (2C), 52.4, 52.1, 50.8, 38.1, 37.4, 25.6, 22.6, 21.9.

Methyl 2-[[4-[[4-[3-(4-fluorobenzoyl)thiazolidin-4-yl]triazol-1-yl]methyl]phenyl]carbamoyl]-4-methyl-pentanoate (91)

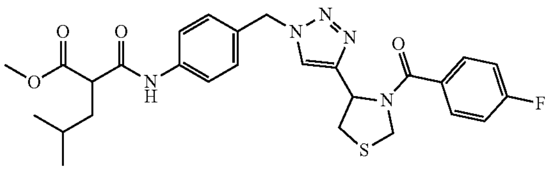 [SMILES: COC(=O)C(CC(C)C)C(=O)Nc1ccc(Cn2cc(C3CSCN3C(=O)c3ccc(F)cc3)nn2)cc1]

Compound 91 was synthesized according to the general procedure E, using azide 87 (80 mg, 0.25 mmol), alkyne 99 (59.1 mg, 0.25 mmol), copper (II) sulfate pentahydrate (12.5 mg, 0.05 mmol) and sodium ascorbate (24.9 mg, 0.13 mmol) in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 91 as brown oil (128 mg, 76%). LC tr=4.40 min, MS (ESI+): m/z=540 $[M+H]^+$. $^1H$ NMR (500 MHz, DMSO-$d_6$) δ ppm: 10.35 (s, 1H), 8.17 (s, 1H), 7.59-7.58 (m, 4H), 7.30-7.28 (m, 4H), 5.96-5.74 (m, 1H), 5.50 (s, 2H), 4.60 (br s, 2H), 3.62 (s, 3H), 3.47-3.42 (m, 1H), 3.29-3.19 (m, 1H), 1.78-1.72 (m, 1H), 1.67-1.61 (m, 1H), 1.51-1.43 (m, 1H), 1.16-0.97 (m, 1H), 0.88 (d, J=6.6 Hz, 3H), 0.86 (d, J=6.8 Hz, 3H). $^{13}C$ NMR (126 MHz, DMSO-$d_6$) δ ppm: 170.2, 167.7, 167.1, 163.1 (d, J=248.7 Hz), 146.7, 138.7, 131.0, 129.9 (d, J=12.4 Hz), 128.7 (2C), 122.7 (2C), 120.2, 119.4 (2C), 115.4 (d, J=21.8 Hz, 2C), 52.5, 52.1, 50.8, 48.6, 37.4, 35.5, 25.7, 25.6, 22.7, 21.9.

Methyl 2-[[4-[[4-[(2-acetamidophenoxy)methyl]triazol-1-yl]methyl]phenyl]carbamoyl]-4-methyl-pentanoate (92)

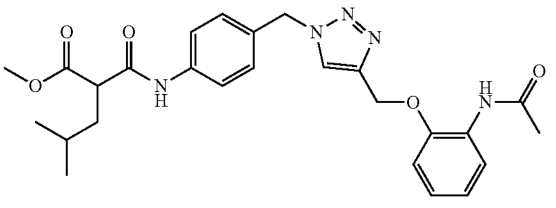 [SMILES: COC(=O)C(CC(C)C)C(=O)Nc1ccc(Cn2cc(COc3ccccc3NC(C)=O)nn2)cc1]

Compound 92 was synthesized according to the general procedure E, using azide 87 (100 mg, 0.33 mmol), alkyne 100 (62.2 mg, 0.33 mmol), copper (II) sulfate pentahydrate (16.4 mg, 0.07 mmol) and sodium ascorbate (32.5 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 92 as a beige powder (139 mg, 62%). LC tr=4.05 min, MS (ESI−): m/z=492 $[M-H]^-$. $^1H$ NMR (500 MHz, DMSO-$d_6$) δ ppm: 10.32 (s, 1H), 9.01 (s, 1H), 8.22 (s, 1H), 7.87 (d, J=7.7 Hz, 1H), 7.59-7.57 (m, 2H), 7.29-7.27 (m, 2H), 7.20 (d, J=7.9 Hz, 1H), 7.04 (t, J=7.4 Hz, 1H), 6.90 (t, J=7.4 Hz, 1H), 5.55 (s, 2H), 5.20 (s, 2H), 3.62 (s, 3H), 3.58 (dd, J=8.9 and 6.1 Hz, 1H), 2.03 (s, 3H), 1.78-1.73 (m, 1H), 1.68-1.62 (m, 1H), 1.48 (sep, J=6.7 Hz, 1H), 0.89 (d, J=6.7 Hz, 3H), 0.87 (d, J=6.7 Hz, 3H). $^{13}C$ NMR (126 MHz, DMSO-$d_6$) δ ppm: 170.2, 168.3, 167.1, 148.5, 143.2, 138.7, 131.0, 128.7 (2C), 127.9, 124.4, 124.2, 122.5, 120.8, 119.4 (2C), 113.3, 62.3, 52.5, 52.1, 50.8, 37.4, 25.6, 23.8, 22.7, 21.9.

Methyl 2-[[4-[[4-[[(4-iodophenyl)sulfonyl-methyl-amino]methyl]triazol-1-yl]methyl]phenyl]carbamoyl]-4-methyl-pentanoate (123)

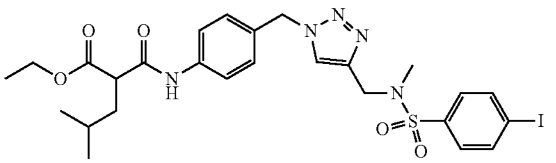 [SMILES: CCOC(=O)C(CC(C)C)C(=O)Nc1ccc(Cn2cc(CN(C)S(=O)(=O)c3ccc(I)cc3)nn2)cc1]

Compound 123 was synthesized according to the general procedure E, using azide 83 (100 mg, 0.31 mmol), alkyne 115 (105 mg, 0.31 mmol), copper (II) sulfate pentahydrate (15.7 mg, 0.06 mmol) and sodium ascorbate (31.1 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 123 as a white powder (132 mg, 59%). LC tr=4.93 min, MS (ESI+): m/z=654 $[M+H]^+$. $^1H$ NMR (500 MHz, DMSO-$d_6$) δ ppm: 10.29 (s, 1H), 8.04 (s, 1H), 7.96-7.94 (m, 2H), 7.59-7.57 (m, 2H), 7.52-7.51 (m, 2H), 7.28-7.26 (m, 2H), 5.49 (s, 2H), 4.26 (s, 2H), 4.13-4.05 (m, 2H), 3.56 (dd, J=8.7 and 6.2 Hz, 1H), 2.64 (s, 3H), 1.77-1.72 (m, 1H), 1.67-1.62 (m, 1H), 1.49 (sep, J=6.7 Hz, 1H), 1.15 (t, J=7.1 Hz, 3H), 0.88 (d, J=6.7 Hz, 3H), 0.87 (d, J=6.7 Hz, 3H). $^{13}C$ NMR (126 MHz, DMSO-$d_6$) δ ppm: 169.7, 167.2, 141.8, 138.8, 138.2 (2C), 136.5, 130.9, 128.9 (2C), 128.7 (2C), 124.0, 119.5 (2C), 101.3, 60.7, 52.5, 50.9, 44.7, 37.4, 34.7, 25.7, 22.7, 21.9, 14.0.

Ethyl 2-[[4-[[4-[[(4-iodobenzoyl)amino]methyl]triazol-1-yl]methyl]phenyl]carbamoyl]-4-methyl-pentanoate (124)

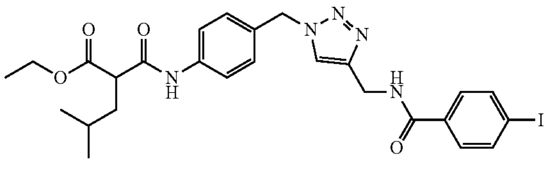 [SMILES: CCOC(=O)C(CC(C)C)C(=O)Nc1ccc(Cn2cc(CNC(=O)c3ccc(I)cc3)nn2)cc1]

Compound 124 was synthesized according to the general procedure E, using azide 83 (100 mg, 0.31 mmol), alkyne 116 (89.5 mg, 0.31 mmol), copper (II) sulfate pentahydrate (15.7 mg, 0.06 mmol) and sodium ascorbate (31.1 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 98/2) affording compound 124 as a white solid (141 mg, 60%). LC tr=4.61 min, MS (ESI+): m/z=604 $[M+H]^+$. $^1$H NMR (500 MHz, DMSO-$d_6$) δ ppm: 10.28 (s, 1H), 9.05 (t, J=5.6 Hz, 1H), 7.98 (s, 1H), 7.85-7.83 (m, 2H), 7.65-7.63 (m, 2H), 7.57-7.55 (m, 2H), 7.30-7.28 (m, 2H), 5.49 (s, 2H), 4.47 (d, J=5.7 Hz, 2H), 4.12-4.05 (m, 2H), 3.55 (dd, J=8.7 and 6.2 Hz, 1H), 1.77-1.71 (m, 1H), 1.67-1.62 (m, 1H), 1.48 (sep, J=6.7 Hz, 1H), 1.15 (t, J=7.1 Hz, 3H), 0.88 (d, J=6.7 Hz, 3H), 0.87 (d, J=6.7 Hz, 3H). $^{13}$C NMR (126 MHz, DMSO-$d_6$) δ ppm: 169.7, 167.1, 165.4, 145.1, 138.7, 137.2 (2C), 133.5, 131.1, 129.3 (2C), 128.8 (2C), 122.9, 119.4 (2C), 98.9, 60.6, 52.4, 50.9, 37.4, 34.9, 25.6, 22.6, 21.9, 14.0.

Ethyl 2-[[4-[[4-[(tert-butoxycarbonylamino)methyl] triazol-1-yl]methyl]phenyl]carbamoyl]-4-methyl-pentanoate (125)

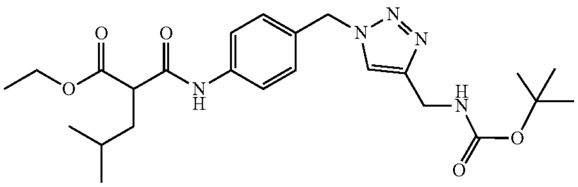 [SMILES: CCOC(=O)C(CC(C)C)C(=O)Nc1ccc(Cn2cc(CNC(=O)OC(C)(C)C)nn2)cc1]

Compound 125 was synthesized according to the general procedure E, using azide 83 (100 mg, 0.31 mmol), N-boc-propargylamine (48.7 mg, 0.31 mmol), copper (II) sulfate pentahydrate (15.7 mg, 0.06 mmol) and sodium ascorbate (31.1 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 125 as a colorless solid (115 mg, 72%). LC tr=4.35 min, MS (ESI+): m/z=474 $[M+H]^+$, 418 $[M+H-tBu]^+$, 374 $[M+H-boc]^+$. $^1$H NMR (500 MHz, DMSO-$d_6$) δ ppm: 10.31 (s, 1H), 7.87 (s, 1H), 7.57-7.56 (m, 2H), 7.31-7.27 (m, 3H), 5.49 (s, 2H), 4.13 (d, J=5.7 Hz, 2H), 4.10-4.07 (m, 2H), 3.55 (dd, J=8.7 and 6.2 Hz, 1H), 1.77-1.71 (m, 1H), 1.66-1.61 (m, 1H), 1.47 (sep, J=6.7 Hz, 1H), 1.36 (s, 9H), 1.14 (t, J=7.1 Hz, 3H), 0.88 (d, J=6.7 Hz, 3H), 0.86 (d, J=6.7 Hz, 3H). $^{13}$C NMR (126 MHz, DMSO-$d_6$) δ ppm: 169.8, 167.2, 155.6, 145.9, 138.7, 131.2, 128.8 (2C), 122.6, 119.4 (2C), 78.0, 60.7, 52.3, 51.0, 37.4, 35.7, 28.3 (3C), 25.7, 22.7, 22.0, 14.1.

Ethyl 2-[[4-[[4-[(4-iodoanilino)methyl]triazol-1-yl] methyl]phenyl]carbamoyl]-4-methyl-pentanoate (126)

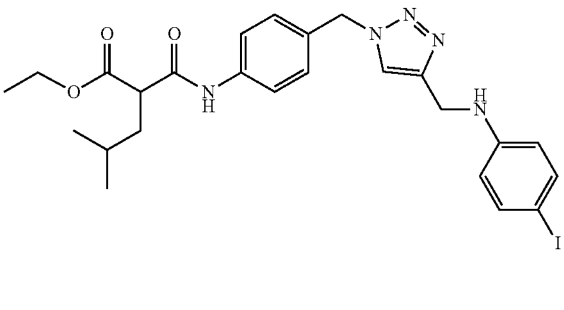 [SMILES: CCOC(=O)C(CC(C)C)C(=O)Nc1ccc(Cn2cc(CNc3ccc(I)cc3)nn2)cc1]

Compound 126 was synthesized according to the general procedure E, using azide 83 (100 mg, 0.31 mmol), alkyne 118 (80.7 mg, 0.31 mmol), copper (II) sulfate pentahydrate (15.7 mg, 0.06 mmol) and sodium ascorbate (31.1 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 98/2) affording compound 126 as yellow oil (170 mg, 85%). LC tr=4.96 min, MS (ESI+): m/z=576 $[M+H]^+$. $^1$H NMR (500 MHz, DMSO-$d_6$) δ ppm: 10.31 (s, 1H), 7.96 (s, 1H), 7.56-7.55 (m, 2H), 7.33-7.31 (m, 2H), 7.27-7.25 (m, 2H), 6.48-6.46 (m, 2H), 6.29 (t, J=8.1 Hz, 1H), 5.49 (s, 2H), 4.23 (d, J=5.4 Hz, 2H), 4.12-4.08 (m, 2H), 3.55 (dd, J=8.8 and 6.2 Hz, 1H), 1.77-1.71 (m, 1H), 1.66-1.61 (m, 1H), 1.47 (sep, J=6.7 Hz, 1H), 1.15 (t, J=7.1 Hz, 3H), 0.88 (d, J=6.7 Hz, 3H), 0.86 (d, J=6.7 Hz, 3H). $^{13}$C NMR (126 MHz, DMSO-$d_6$) δ ppm: 169.8, 167.2, 148.1, 145.6, 138.7, 137.1 (2C), 131.2, 128.8 (2C), 122.8, 119.5 (2C), 115.0 (2C), 76.6, 60.7, 52.4, 50.9, 38.3, 37.4, 25.7, 22.7, 22.0, 14.1.

Ethyl 2-[[4-[[4-[(4-chlorophenoxy)methyl]triazol-1-yl]methyl]phenyl]carbamoyl]-4-methyl-pentanoate (127)

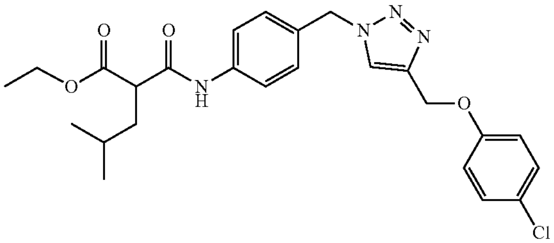 [SMILES: CCOC(=O)C(CC(C)C)C(=O)Nc1ccc(Cn2cc(COc3ccc(Cl)cc3)nn2)cc1]

Compound 127 was synthesized according to the general procedure E, using azide 83 (70 mg, 0.22 mmol), alkyne 119 (36.6 mg, 0.22 mmol), copper (II) sulfate pentahydrate (11 mg, 0.04 mmol) and sodium ascorbate (21.8 mg, 0.11 mmol) in DMF (5 mL) and $H_2O$ (4 mL) overnight. The crude product was purified by flash chromatography on silica gel ($CH_2Cl_2$ to $CH_2Cl_2$/MeOH: 95/5) affording compound 127 as a white solid (59 mg, 54%). LC tr=4.99 min, MS (ESI+): m/z=485 and 487 $[M+H]^+$. $^1$H NMR (500 MHz, DMSO-$d_6$) δ ppm: 10.30 (s, 1H), 8.23 (s, 1H), 7.59-7.57 (m, 2H), 7.33-7.29 (m, 4H), 7.07-7.02 (m, 2H), 5.54 (s, 2H), 5.12 (s, 2H), 4.13-4.05 (m, 2H), 3.56 (dd, J=8.7 and 6.2 Hz, 1H), 1.77-1.72 (m, 1H), 1.67-1.62 (m, 1H), 1.48 (sep, J=6.7 Hz, 1H), 1.15 (t, J=7.1 Hz, 3H), 0.89 (d, J=6.7 Hz, 3H), 0.87 (d, J=6.7 Hz, 3H). $^{13}$C NMR (126 MHz, DMSO-$d_6$) δ ppm: 169.7, 167.2, 156.9, 142.7, 138.8, 130.9, 129.2 (3C), 128.8 (2C), 124.6, 119.5 (2C), 116.5 (2C), 61.4, 60.7, 52.5, 50.9, 37.4, 25.6, 22.6, 21.9, 14.0.

Ethyl 2-[[4-[[4-[(4-chlorophenyl)sulfanylmethyl] triazol-1-yl]methyl]phenyl]carbamoyl]-4-methyl-pentanoate (128)

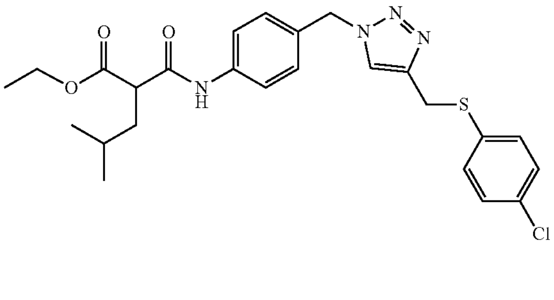

Compound 128 was synthesized according to the general procedure E, using azide 83 (70 mg, 0.22 mmol), alkyne 120 (40.2 mg, 0.22 mmol), copper (II) sulfate pentahydrate (11 mg, 0.04 mmol) and sodium ascorbate (21.8 mg, 0.11 mmol) in DMF (5 mL) and $H_2O$ (4 mL) overnight. The crude product was purified by flash chromatography on silica gel ($CH_2Cl_2$ to $CH_2Cl_2$/MeOH: 95/5) affording compound 128 as a white solid (77 mg, 69%). LC tr=5.01 min, MS (ESI+): m/z=501 and 503 $[M+H]^+$. $^1H$ NMR (500 MHz, DMSO-$d_6$) δ ppm: 10.28 (s, 1H), 7.92 (s, 1H), 7.57-7.55 (m, 2H), 7.36-7.31 (m, 4H), 7.21-7.19 (m, 2H), 5.47 (s, 2H), 4.27 (s, 2H), 4.13-4.05 (m, 2H), 3.56 (dd, J=8.7 and 6.2 Hz, 1H), 1.77-1.72 (m, 1H), 1.68-1.62 (m, 1H), 1.49 (sep, J=6.7 Hz, 1H), 1.15 (t, J=7.1 Hz, 3H), 0.89 (d, J=6.7 Hz, 3H), 0.87 (d, J=6.7 Hz, 3H). $^{13}C$ NMR (126 MHz, DMSO-$d_6$) δ ppm: 169.7, 167.1, 143.5, 138.7, 134.7, 131.0, 130.7, 130.2 (2C), 128.8 (2C), 128.5 (2C), 123.3, 119.4 (2C), 60.6, 52.4, 50.9, 37.4, 27.3, 25.6, 22.6, 21.9, 14.0.

Ethyl 2-[[4-[[4-[(4-chlorophenyl)methyl]triazol-1-yl]methyl]phenyl]carbamoyl]-4-methyl-pentanoate (129)

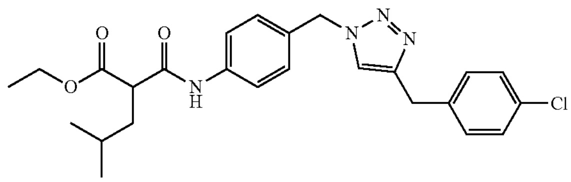 [SMILES: CCOC(=O)C(CC(C)C)C(=O)Nc1ccc(Cn2cc(Cc3ccc(Cl)cc3)nn2)cc1]

Compound 129 was synthesized according to the general procedure E, using azide 83 (100 mg, 0.31 mmol), alkyne 121 (47.3 mg, 0.31 mmol), copper (II) sulfate pentahydrate (15.7 mg, 0.06 mmol) and sodium ascorbate (31.1 mg, 0.16 mmol) in DMF (5.5 mL) and $H_2O$ (4.5 mL) overnight. The crude product was purified by flash chromatography on silica gel (cHex to cHex/EtOAc: 5/5) affording compound 129 as a white solid (85 mg, 54%). LC tr=4.92 min, MS (ESI+): m/z=469 and 471 $[M+H]^+$. $^1H$ NMR (500 MHz, DMSO-$d_6$) δ ppm: 10.29 (s, 1H), 7.85 (s, 1H), 7.57-7.55 (m, 2H), 7.34-7.33 (m, 2H), 7.28-7.24 (m, 4H), 5.47 (s, 2H), 4.13-4.05 (m, 2H), 3.96 (s, 2H), 3.55 (dd, J=8.7 and 6.2 Hz, 1H), 1.77-1.71 (m, 1H), 1.67-1.62 (m, 1H), 1.48 (sep, J=6.7 Hz, 1H), 1.15 (t, J=7.1 Hz, 3H), 0.88 (d, J=6.7 Hz, 3H), 0.87 (d, J=6.7 Hz, 3H). $^{13}C$ NMR (126 MHz, DMSO-$d_6$) δ ppm: 169.7, 167.1, 145.9, 138.7, 138.6, 131.1, 130.8, 130.4 (2C), 128.7 (2C), 128.3 (2C), 122.5, 119.4 (2C), 60.7, 52.4, 50.9, 37.4, 30.5, 25.6, 22.6, 21.9, 14.0.

Ethyl 2-[[4-[[4-(4-iodophenyl)triazol-1-yl]methyl]phenyl]carbamoyl]-4-methyl-pentanoate (130)

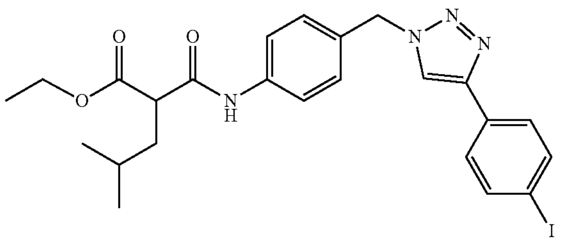 [SMILES: CCOC(=O)C(CC(C)C)C(=O)Nc1ccc(Cn2cc(-c3ccc(I)cc3)nn2)cc1]

Compound 130 was synthesized according to the general procedure E, using azide 83 (100 mg, 0.31 mmol), alkyne 122 (71.6 mg, 0.31 mmol), copper (II) sulfate pentahydrate (15.7 mg, 0.06 mmol) and sodium ascorbate (31.1 mg, 0.16 mmol) in DMF (5.5 mL) and $H_2O$ (4.5 mL) overnight. The crude product was purified by flash chromatography on silica gel (cHex to cHex/EtOAc: 7/3) affording compound 130 as a white solid (151 mg, 82%). LC tr=5.21 min, MS (ESI+): m/z=547 $[M+H]^+$. $^1H$ NMR (500 MHz, DMSO-$d_6$) δ ppm: 10.33 (s, 1H), 8.64 (s, 1H), 7.80-7.78 (m, 2H), 7.66-7.64 (m, 2H), 7.60-7.59 (m, 2H), 7.34-7.32 (m, 2H), 5.58 (s, 2H), 4.12-4.05 (m, 2H), 3.56 (dd, J=8.8 and 6.1 Hz, 1H), 1.77-1.71 (m, 1H), 1.66-1.61 (m, 1H), 1.47 (sep, J=6.7 Hz, 1H), 1.14 (t, J=7.1 Hz, 3H), 0.88 (d, J=6.7 Hz, 3H), 0.86 (d, J=6.7 Hz, 3H). $^{13}C$ NMR (126 MHz, DMSO-$d_6$) δ ppm: 169.7, 167.2, 145.7, 138.8, 137.7 (2C), 130.8, 130.2, 128.8 (2C), 127.2 (2C), 121.7, 119.5 (2C), 93.7, 60.7, 52.7, 50.9, 37.4, 25.6, 22.6, 21.9, 14.0.

Ethyl 2-[[3-[[4-[[(4-iodophenyl)sulfonylamino]methyl]triazol-1-yl]methyl]phenyl]carbamoyl]-4-methyl-pentanoate (113)

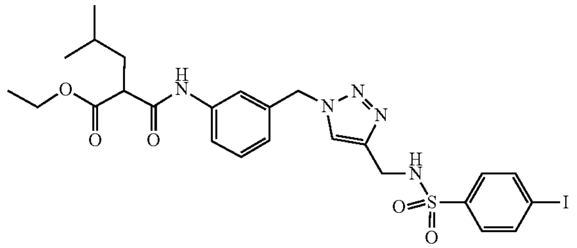 [SMILES: CCOC(=O)C(CC(C)C)C(=O)Nc1cccc(Cn2cc(CNS(=O)(=O)c3ccc(I)cc3)nn2)c1]

Compound 113 was synthesized according to the general procedure E, using azide 112 (110 mg, 0.35 mmol), alkyne 93 (111 mg, 0.35 mmol), copper (II) sulfate pentahydrate (17.3 mg, 0.07 mmol) and sodium ascorbate (34.2 mg, 0.17 mmol) in DMF (5.5 mL) and $H_2O$ (4.5 mL) overnight. The crude product was purified by flash chromatography on silica gel ($CH_2Cl_2$ to $CH_2Cl_2$/MeOH: 98/2) affording compound 113 as yellow oil (218 mg, 86%). LC tr=4.71 min, MS (ESI+): m/z=640 $[M+H]^+$. $^1H$ NMR (500 MHz, DMSO-$d_6$) δ ppm: 10.30 (s, 1H), 8.21 (br s, 1H), 7.93-7.92 (m, 2H), 7.90 (s, 1H), 7.56-7.55 (m, 2H), 7.52-7.50 (m, 2H), 7.33-7.30 (m, 1H), 6.97-6.96 (m, 1H), 5.50 (s, 2H), 4.13-4.06 (m, 2H), 4.05-4.04 (m, 2H), 3.56 (dd, J=8.7 and 6.2 Hz, 1H), 1.78-1.72 (m, 1H), 1.67-1.62 (m, 1H), 1.48 (sep, J=6.7 Hz, 1H), 1.15 (t, J=7.1 Hz, 3H), 0.89 (d, J=6.7 Hz, 3H), 0.87 (d, J=6.7 Hz, 3H). $^{13}C$ NMR (126 MHz, DMSO-$d_6$) δ ppm: 169.7, 167.2, 143.5, 140.0, 139.2, 138.0 (2C), 136.6, 129.3, 128.3 (2C), 123.5, 123.2, 119.0, 118.7, 100.4, 60.7, 52.7, 50.9, 38.0, 37.4, 25.7, 22.7, 21.9, 14.1.

Ethyl 2-[[4-[[4-[[(4-fluorophenyl)sulfonylamino]methyl]triazol-1-yl]methyl]phenyl]carbamoyl]-4-methyl-pentanoate (150)

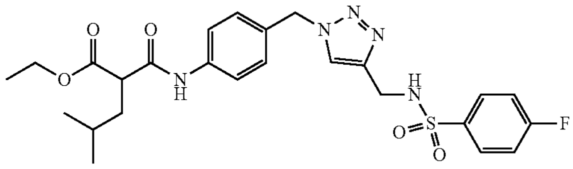 [SMILES: CCOC(=O)C(CC(C)C)C(=O)Nc1ccc(Cn2cc(CNS(=O)(=O)c3ccc(F)cc3)nn2)cc1]

Compound 150 was synthesized according to the general procedure E, using azide 83 (100 mg, 0.31 mmol), alkyne 141 (67 mg, 0.31 mmol), copper (II) sulfate pentahydrate (15.7 mg, 0.06 mmol) and sodium ascorbate (31.1 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 150 as a pale yellow solid (137 mg, 76%). LC tr=4.38 min, MS (ESI+): m/z=532 $[M+H]^+$. $^1H$ NMR (500 MHz, DMSO-$d_6$) δ ppm: 10.29 (s, 1H), 8.15 (t, J=5.8 Hz, 1H), 7.85 (s, 1H), 7.82-7.79 (m, 2H), 7.58-7.56 (m, 2H), 7.37-7.33 (m, 2H), 7.25-7.23 (m, 2H), 5.45 (s, 2H), 4.13-4.06 (m, 2H), 4.04 (d, J=5.8 Hz, 2H), 3.56 (dd, J=8.7 and 6.2 Hz, 1H), 1.77-1.72 (m, 1H), 1.68-1.62 (m, 1H), 1.49 (sep, J=6.7 Hz, 1H), 1.15 (t, J=7.1 Hz, 3H), 0.89 (d, J=6.7 Hz, 3H), 0.87 (d, J=6.7 Hz, 3H). $^{13}C$ NMR (126 MHz, DMSO-$d_6$) δ ppm: 169.7, 167.2, 164.1 (d, J=250.8 Hz), 143.5, 138.7, 136.8 (d, J=2.9 Hz), 130.9, 129.6 (d, J=9.2 Hz, 2C), 128.8 (2C), 123.2, 119.4 (2C), 116.2 (d, J=22.1 Hz, 2C), 60.7, 52.4, 51.0, 38.0, 37.4, 25.7, 22.7, 21.9, 14.0.

Ethyl 2-[[4-[[4-[[(4-chlorophenyl)sulfonylamino] methyl]triazol-1-yl]methyl]phenyl]carbamoyl]-4-methyl-pentanoate (151)

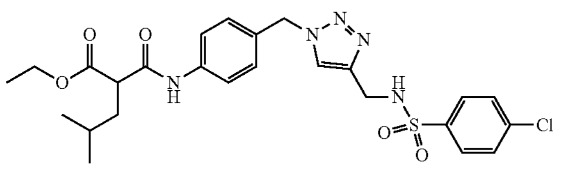

Compound 151 was synthesized according to the general procedure E, using azide 83 (100 mg, 0.31 mmol), alkyne 142 (72.1 mg, 0.31 mmol), copper (II) sulfate pentahydrate (15.7 mg, 0.06 mmol) and sodium ascorbate (31.1 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 98/2) affording compound 151 as a colorless wax (138 mg, 73%). LC tr=4.55 min, MS (ESI+): m/z=548 and 550 $[M+H]^+$. $^1H$ NMR (500 MHz, DMSO-$d_6$) δ ppm: 10.29 (s, 1H), 8.22 (t, J=5.9 Hz, 1H), 7.86 (s, 1H), 7.75-7.73 (m, 2H), 7.59-7.57 (m, 4H), 7.25-7.24 (m, 2H), 5.45 (s, 2H), 4.11-4.05 (m, 4H), 3.56 (dd, J=8.7 and 6.2 Hz, 1H), 1.78-1.72 (m, 1H), 1.68-1.62 (m, 1H), 1.49 (sep, J=6.7 Hz, 1H), 1.15 (t, J=7.1 Hz, 3H), 0.89 (d, J=6.7 Hz, 3H), 0.87 (d, J=6.7 Hz, 3H). $^{13}C$ NMR (126 MHz, DMSO-$d_6$) δ ppm: 169.7, 167.1, 143.4, 139.3, 138.7, 137.2, 130.9, 129.2 (2C), 128.8 (2C), 128.5 (2C), 123.2, 119.4 (2C), 60.7, 52.3, 50.9, 38.0, 37.4, 25.6, 22.6, 21.9, 14.0.

Ethyl 2-[[4-[[4-[[(4-methoxyphenyl)sulfonylamino] methyl]triazol-1-yl]methyl]phenyl]carbamoyl]-4-methyl-pentanoate (152)

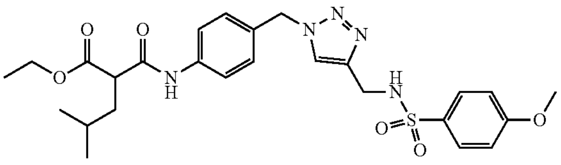 [SMILES: CCOC(=O)C(CC(C)C)C(=O)Nc1ccc(Cn2cc(CNS(=O)(=O)c3ccc(OC)cc3)nn2)cc1]

Compound 152 was synthesized according to the general procedure E, using azide 83 (100 mg, 0.31 mmol), alkyne 143 (70.8 mg, 0.31 mmol), copper (II) sulfate pentahydrate (15.7 mg, 0.06 mmol) and sodium ascorbate (31.1 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 152 as a white solid (141 mg, 76%). LC tr=4.34 min, MS (ESI+): m/z=544 $[M+H]^+$. $^1H$ NMR (500 MHz, DMSO-$d_6$) δ ppm: 10.29 (s, 1H), 7.92 (t, J=5.8 Hz, 1H), 7.85 (s, 1H), 7.70-7.69 (m, 2H), 7.58-7.56 (m, 2H), 7.25-7.24 (m, 2H), 7.07-7.05 (m, 2H), 5.46 (s, 2H), 4.13-4.05 (m, 2H), 3.98 (d, J=5.9 Hz, 2H), 3.82 (s, 3H), 3.56 (dd, J=8.9 and 6.5 Hz, 1H), 1.77-1.72 (m, 1H), 1.68-1.62 (m, 1H), 1.48 (sep, J=6.7 Hz, 1H), 1.15 (t, J=7.1 Hz, 3H), 0.89 (d, J=6.7 Hz, 3H), 0.87 (d, J=6.7 Hz, 3H). $^{13}C$ NMR (126 MHz, DMSO-$d_6$) δ ppm: 169.7, 167.1, 162.1, 143.7, 138.7, 131.9, 131.0, 128.7 (4C), 123.2, 119.4 (2C), 114.3 (2C), 60.7, 55.6, 52.4, 51.0, 38.1, 37.4, 25.7, 22.7, 21.9, 14.0.

Ethyl 2-[[4-[[4-[[(2-chlorophenyl)sulfonylamino] methyl]triazol-1-yl]methyl]phenyl]carbamoyl]-4-methyl-pentanoate (153)

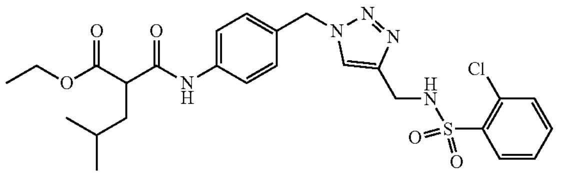 [SMILES: CCOC(=O)C(CC(C)C)C(=O)Nc1ccc(Cn2cc(CNS(=O)(=O)c3ccccc3Cl)nn2)cc1]

Compound 153 was synthesized according to the general procedure E, using azide 83 (100 mg, 0.31 mmol), alkyne 144 (72.1 mg, 0.31 mmol), copper (II) sulfate pentahydrate (15.7 mg, 0.06 mmol) and sodium ascorbate (31.1 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 98/2) affording compound 153 as colorless oil (170 mg, 82%). LC tr=4.40 min, MS (ESI+): m/z=548 and 550 $[M+H]^+$. $^1H$ NMR (500 MHz, DMSO-$d_6$) δ ppm: 10.31 (s, 1H), 8.37 (br s, 1H), 7.88 (dd, J=7.9 and 1.6 Hz, 1H), 7.73 (s, 1H), 7.59-7.57 (m, 2H), 7.53 (td, J=11.5 and 1.6 Hz, 1H), 7.48 (dd, J=7.9 and 1.3 Hz, 1H), 7.42 (td, J=11.3 and 1.3 Hz, 1H), 7.23-7.22 (m, 2H), 5.42 (s, 2H), 4.15 (br s, 2H), 4.11-4.08 (m, 2H), 3.56 (dd, J=9.0 and 6.4 Hz, 1H), 1.78-1.73 (m, 1H), 1.68-1.63 (m, 1H), 1.49 (sep, J=6.6 Hz, 1H), 1.15 (t, J=7.0 Hz, 3H), 0.89 (d, J=6.6 Hz, 3H), 0.87 (d, J=6.6 Hz, 3H). $^{13}C$ NMR (126 MHz, DMSO-$d_6$) δ ppm: 169.7, 167.2, 143.6, 138.7, 138.0, 133.8, 131.5, 130.9, 130.5, 130.3, 128.8 (2C), 127.4, 123.0, 119.5 (2C), 60.7, 52.3, 51.0, 37.8, 37.4, 25.7, 22.6, 21.9, 14.0.

Ethyl 2-[[4-[[4-[[(3-chlorophenyl)sulfonylamino] methyl]triazol-1-yl]methyl]phenyl]carbamoyl]-4-methyl-pentanoate (154)

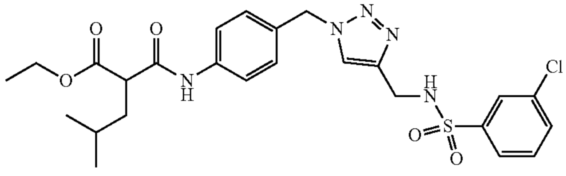 [SMILES: CCOC(=O)C(CC(C)C)C(=O)Nc1ccc(Cn2cc(CNS(=O)(=O)c3cccc(Cl)c3)nn2)cc1]

Compound 154 was synthesized according to the general procedure E, using azide 83 (100 mg, 0.31 mmol), alkyne 145 (72.1 mg, 0.31 mmol), copper (II) sulfate pentahydrate (15.7 mg, 0.06 mmol) and sodium ascorbate (31.1 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 98/2) affording compound 154 as a white solid (136 mg, 74%). LC tr=4.55 min, MS (ESI+): m/z=548 and 550 $[M+H]^+$. $^1$H NMR (500 MHz, DMSO-$d_6$) δ ppm: 10.30 (s, 1H), 8.28 (br s, 1H), 7.82 (s, 1H), 7.74 (t, J=1.7 Hz, 1H), 7.70-7.68 (m, 1H), 7.66-7.64 (m, 1H), 7.58-7.56 (m, 2H), 7.53 (t, J=7.9 Hz, 1H), 7.25-7.23 (m, 2H), 5.44 (s, 2H), 4.13-4.06 (m, 4H), 3.56 (dd, J=8.7 and 6.2 Hz, 1H), 1.78-1.72 (m, 1H), 1.68-1.62 (m, 1H), 1.49 (sep, J=6.7 Hz, 1H), 1.15 (t, J=7.1 Hz, 3H), 0.89 (d, J=6.7 Hz, 3H), 0.87 (d, J=6.7 Hz, 3H). $^{13}$C NMR (126 MHz, DMSO-$d_6$) δ ppm: 169.7, 167.2, 143.3, 142.4, 138.7, 133.7, 132.3, 131.1, 130.9, 128.8 (2C), 126.1, 125.2, 123.1, 119.5 (2C), 60.7, 52.4, 50.9, 38.0, 37.4, 25.7, 22.6, 21.9, 14.0.

Ethyl 2-[[4-[[4-[[(3,4-dichlorophenyl)sulfonylamino]methyl]triazol-1-yl]methyl]phenyl]carbamoyl]-4-methyl-pentanoate (155)

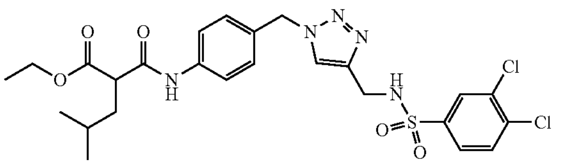 [SMILES: CCOC(=O)C(CC(C)C)C(=O)Nc1ccc(Cn2cc(CNS(=O)(=O)c3ccc(Cl)c(Cl)c3)nn2)cc1]

Compound 155 was synthesized according to the general procedure E, using azide 83 (70 mg, 0.22 mmol), alkyne 146 (58.1 mg, 0.22 mmol), copper (II) sulfate pentahydrate (11 mg, 0.04 mmol) and sodium ascorbate (21.8 mg, 0.11 mmol) in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 155 as a white powder (108 mg, 77%). LC tr=4.76 min, MS (ESI+): m/z=582, 584 and 586 $[M+H]^+$. $^1$H NMR (500 MHz, DMSO-$d_6$) δ ppm: 10.29 (s, 1H), 8.36 (br s, 1H), 7.91 (d, J=2.1 Hz, 1H), 7.88 (s, 1H), 7.77 (d, J=8.4 Hz, 1H), 7.67 (dd, J=8.4 and 2.1 Hz, 1H), 7.58-7.57 (m, 2H), 7.25-7.23 (m, 2H), 5.45 (s, 2H), 4.11-4.05 (m, 4H), 3.56 (dd, J=8.8 and 6.2 Hz, 1H), 1.78-1.72 (m, 1H), 1.68-1.62 (m, 1H), 1.49 (sep, J=6.6 Hz, 1H), 1.15 (t, J=7.1 Hz, 3H), 0.89 (d, J=6.6 Hz, 3H), 0.87 (d, J=6.6 Hz, 3H). $^{13}$C NMR (126 MHz, DMSO-$d_6$) δ ppm: 169.7, 167.1, 143.2, 140.9, 138.7, 135.4, 131.9, 131.4, 130.8, 128.7 (2C), 128.4, 126.6, 123.2, 119.5 (2C), 60.7, 52.4, 50.9, 38.0, 37.4, 25.6, 22.6, 21.9, 14.0.

Ethyl 2-[[4-[[4-[[(4-chlorophenyl)methylsulfonylamino]methyl]triazol-1-yl]methyl]phenyl]carbamoyl]-4-methyl-pentanoate (156)

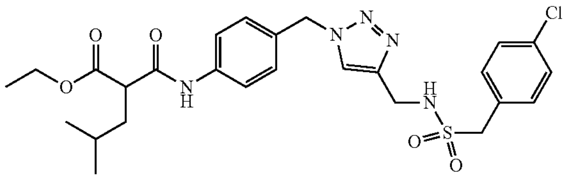 [SMILES: CCOC(=O)C(CC(C)C)C(=O)Nc1ccc(Cn2cc(CNS(=O)(=O)Cc3ccc(Cl)cc3)nn2)cc1]

Compound 156 was synthesized according to the general procedure E, using azide 83 (70 mg, 0.22 mmol), alkyne 147 (53.6 mg, 0.22 mmol), copper (II) sulfate pentahydrate (11 mg, 0.04 mmol) and sodium ascorbate (21.8 mg, 0.11 mmol) in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 156 as colorless oil (65 mg, 45%). LC tr=4.60 min, MS (ESI+): m/z=562 and 564 $[M+H]^+$. $^1$H NMR (500 MHz, DMSO-$d_6$) δ ppm: 10.29 (s, 1H), 7.99 (s, 1H), 7.63 (t, J=5.9 Hz, 1H), 7.59-7.57 (m, 2H), 7.37-7.36 (m, 2H), 7.32-7.30 (m, 2H), 7.28-7.27 (m, 2H), 5.53 (s, 2H), 4.34 (s, 2H), 4.17 (d, J=5.9 Hz, 2H), 4.13-4.05 (m, 2H), 3.55 (dd, J=8.6 and 6.2 Hz, 1H), 1.77-1.71 (m, 1H), 1.68-1.62 (m, 1H), 1.48 (sep, J=6.7 Hz, 1H), 1.15 (t, J=7.1 Hz, 3H), 0.88 (d, J=6.7 Hz, 3H), 0.87 (d, J=6.7 Hz, 3H). $^{13}$C NMR (126 MHz, DMSO-$d_6$) δ ppm: 169.7, 167.1, 144.7, 138.8, 132.9, 132.5 (2C), 131.1, 129.3, 128.8 (2C), 128.3 (2C), 123.2, 119.4 (2C), 60.7, 56.7, 52.4, 50.9, 38.0, 37.4, 25.6, 22.6, 21.9, 14.0.

Ethyl 2-[[4-[[4-(benzenesulfonamidomethyl)triazol-1-yl]methyl]phenyl]carbamoyl]-4-methyl-pentanoate (157)

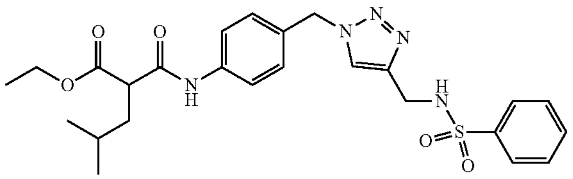 [SMILES: CCOC(=O)C(CC(C)C)C(=O)Nc1ccc(Cn2cc(CNS(=O)(=O)c3ccccc3)nn2)cc1]

Compound 157 was synthesized according to the general procedure E, using azide 83 (100 mg, 0.31 mmol), alkyne 148 (61.3 mg, 0.31 mmol), copper (II) sulfate pentahydrate (15.7 mg, 0.06 mmol) and sodium ascorbate (31.1 mg, 0.17 mmol) in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 157 as colorless wax (123 mg, 68%). LC tr=4.32 min, MS (ESI+): m/z=514 $[M+H]^+$. $^1$H NMR (500 MHz, DMSO-$d_6$) δ ppm: 10.33 (s, 1H), 8.13 (t, J=5.9 Hz, 1H), 7.81 (s, 1H), 7.76-7.74 (m, 2H), 7.61-7.51 (m, 5H), 7.25-7.23 (m, 2H), 5.44 (s, 2H), 4.12-4.05 (m, 2H), 4.03 (d, J=5.9 Hz, 2H), 3.56 (dd, J=9.0 and 6.1 Hz, 1H), 1.78-1.72 (m, 1H), 1.67-1.62 (m, 1H), 1.48 (sep, J=6.7 Hz, 1H), 1.15 (t, J=7.1 Hz, 3H), 0.89 (d, J=6.7 Hz, 3H), 0.87 (d, J=6.7 Hz, 3H). $^{13}$C NMR (126 MHz, DMSO-$d_6$) δ ppm: 170.2, 167.6, 141.1, 140.8, 139.2, 132.8, 131.4, 129.5 (2C), 129.2 (2C), 126.9 (2C), 123.6, 119.9 (2C), 61.1, 52.8, 51.4, 38.6, 37.8, 26.1, 23.1, 22.4, 14.5.

Ethyl 2-[[4-[[4-[(cyclohexylsulfonylamino)methyl]triazol-1-yl]methyl]phenyl]carbamoyl]-4-methyl-pentanoate (158)

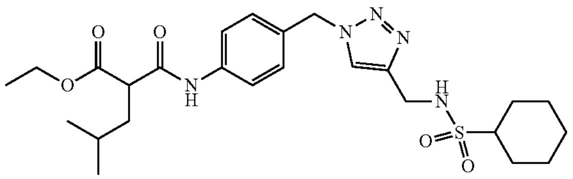 [SMILES: CCOC(=O)C(CC(C)C)C(=O)Nc1ccc(Cn2cc(CNS(=O)(=O)C3CCCCC3)nn2)cc1]

Compound 158 was synthesized according to the general procedure E, using azide 83 (70 mg, 0.22 mmol), alkyne 149 (44.3 mg, 0.22 mmol), copper (II) sulfate pentahydrate (11 mg, 0.04 mmol) and sodium ascorbate (21.8 mg, 0.11 mmol) in DMF (5.5 mL) and $H_2O$ (4.5 mL) overnight. The crude product was purified by flash chromatography on silica gel ($CH_2Cl_2$ to $CH_2Cl_2$/MeOH: 9/1) affording compound 158 as colorless oil (58 mg, 47%). LC tr=4.39 min, MS (ESI+): m/z=520 $[M+H]^+$. $^1H$ NMR (500 MHz, DMSO-$d_6$) δ ppm: 10.28 (s, 1H), 8.01 (s, 1H), 7.58-7.56 (m, 2H), 7.50 (t, J=5.4 Hz, 1H), 7.31-7.29 (m, 2H), 5.52 (s, 2H), 4.18 (d, J=4.6 Hz, 2H), 4.10-4.07 (m, 2H), 3.56-3.53 (m, 1H), 2.71-2.64 (m, 1H), 1.89-1.87 (m, 2H), 1.77-1.71 (m, 1H), 1.67-1.64 (m, 3H), 1.53-1.52 (m, 1H), 1.49-1.46 (m, 1H), 1.23-1.21 (m, 2H), 1.15 (t, J=6.8 Hz, 3H), 1.03-1.00 (m, 3H), 0.89-0.86 (m, 6H). $^{13}C$ NMR (126 MHz, DMSO-$d_6$) δ ppm: 169.7, 167.1, 144.9, 138.7, 131.1, 128.7 (2C), 123.1, 119.4 (2C), 60.6, 59.4, 52.4, 50.9, 37.7, 37.4, 25.9 (2C), 25.6, 24.8, 24.4 (2C), 22.6, 21.9, 14.0.

Ethyl 2-[[4-[[4-[(isobutylsulfonylamino)methyl]triazol-1-yl]methyl]phenyl]carbamoyl]-4-methyl-pentanoate (159)

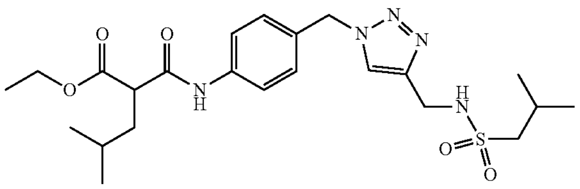 [SMILES: CCOC(=O)C(CC(C)C)C(=O)Nc1ccc(Cn2cc(CNS(=O)(=O)CC(C)C)nn2)cc1]

Compound 159 was synthesized according to the general procedure E, using azide 83 (100 mg, 0.31 mmol), alkyne 106 (55 mg, 0.31 mmol), copper (II) sulfate pentahydrate (15.7 mg, 0.06 mmol) and sodium ascorbate (31.1 mg, 0.17 mmol) in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 159 as colorless oil (85 mg, 51%). LC tr=4.29 min, MS (ESI+): m/z=494 $[M+H]^+$. $^1H$ NMR (500 MHz, DMSO-$d_6$) δ ppm: 10.29 (s, 1H), 8.01 (s, 1H), 7.58-7.56 (m, 2H), 7.53 (t, J=5.9 Hz, 1H), 7.30-7.28 (m, 2H), 5.52 (s, 2H), 4.18 (d, J=5.9 Hz, 2H), 4.10-4.07 (m, 2H), 3.55 (dd, J=8.6 and 6.3 Hz, 1H), 2.80 (d, J=6.4 Hz, 2H), 1.97 (sep, J=6.7 Hz, 1H), 1.77-1.71 (m, 1H), 1.67-1.62 (m, 1H), 1.48 (sep, J=6.7 Hz, 1H), 1.15 (t, J=7.1 Hz, 3H), 0.91 (d, J=6.7 Hz, 6H), 0.88 (d, J=6.7 Hz, 3H), 0.87 (d, J=6.7 Hz, 3H). $^{13}C$ NMR (126 MHz, DMSO-$d_6$) δ ppm: 169.7, 167.2, 144.6, 138.7, 131.1, 128.7 (2C), 123.2, 119.4 (2C), 60.7, 59.2, 52.4, 50.9, 37.6, 37.4, 25.6, 24.1, 22.7, 22.1 (2C), 21.9, 14.0.

Ethyl 2-benzyl-3-[4-[[4-[[(4-iodophenyl)sulfonylamino]methyl]triazol-1-yl]methyl]anilino]-3-oxo-propanoate (177)

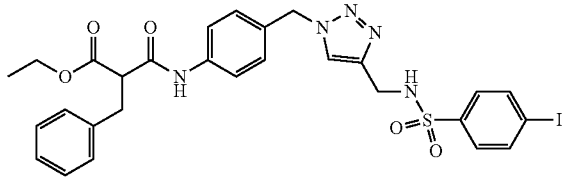 [SMILES: CCOC(=O)C(Cc1ccccc1)C(=O)Nc1ccc(Cn2cc(CNS(=O)(=O)c3ccc(I)cc3)nn2)cc1]

Compound 177 was synthesized according to the general procedure E, using azide 173 (65 mg, 0.18 mmol), alkyne 93 (59.2 mg, 0.18 mmol), copper (II) sulfate pentahydrate (9.21 mg, 0.04 mmol) and sodium ascorbate (18.3 mg, 0.09 mmol) in DMF (5 mL) and $H_2O$ (4 mL) overnight. The crude product was purified by flash chromatography on silica gel ($CH_2Cl_2$ to $CH_2Cl_2$/MeOH: 95/5) affording compound 176 as a colorless solid (94 mg, 74%). LC tr=4.59 min, MS (ESI+): m/z=674 $[M+H]^+$. $^1H$ NMR (500 MHz, DMSO-$d_6$) δ ppm: 10.20 (s, 1H), 8.18 (t, J=5.6 Hz, 1H), 7.93-7.91 (m, 2H), 7.84 (s, 1H), 7.51-7.49 (m, 4H), 7.26-7.22 (m, 6H), 7.18-7.15 (m, 1H), 5.44 (s, 2H), 4.08 (q, J=7.0 Hz, 2H), 4.02 (d, J=5.5 Hz, 2H), 3.82 (dd, J=8.2 and 7.1 Hz, 1H), 3.16-3.08 (m, 2H), 1.12 (t, J=7.0 Hz, 3H). $^{13}C$ NMR (126 MHz, DMSO-$d_6$) δ ppm: 169.0, 166.4, 143.4, 140.0, 138.5, 138.4, 138.0 (2C), 130.9, 128.8 (2C), 128.7 (2C), 128.3 (2C), 128.2 (2C), 126.4, 123.2, 119.5 (2C), 100.4, 60.8, 54.3, 52.3, 38.0, 34.2, 14.0.

2-(Hydroxycarbamoyl)-N-[4-[[4-[[(4-iodophenyl)sulfonylamino]methyl]triazol-1-yl]methyl]phenyl]-4-methyl-pentanamide (Hit L1)

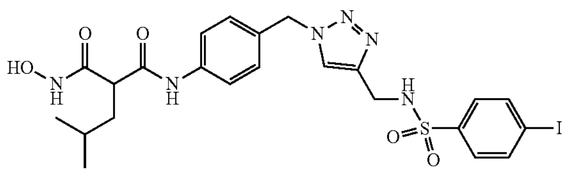 [SMILES: CC(C)CC(C(=O)NO)C(=O)Nc1ccc(Cn2cc(CNS(=O)(=O)c3ccc(I)cc3)nn2)cc1]

Hit L1 was synthesized according to the general procedure D, using ester 88 (110 mg, 0.17 mmol), KCN (2.27 mg, 0.03 mmol) and $NH_2OH$ (1.5 mL, 50% w/w in water) in MeOH (1.5 mL) overnight. The crude product was purified by flash chromatography on silica gel ($CH_2Cl_2$ to $CH_2Cl_2$/MeOH: 95/5) affording compound Hit L1 as a white solid after lyophilization (96 mg, 85%). Purity: 97%, LC tr=3.77 min, MS (ESI+): m/z=627 $[M+H]^+$. $^1H$ NMR (300 MHz, DMSO-$d_6$) δ ppm: 10.54 (br s, 1H), 9.92 (s, 1H), 8.96 (br s, 1H), 8.34-8.08 (m, 1H), 7.93-7.91 (m, 2H), 7.83 (s, 1H), 7.58-7.57 (m, 2H), 7.51-7.49 (m, 2H), 7.24-7.23 (m, 2H), 5.44 (s, 2H), 4.03 (s, 2H), 3.23 (t, J=7.5 Hz, 1H), 1.67 (t, J=7.1 Hz, 2H), 1.46 (sep, J=6.6 Hz, 1H), 0.85-0.87 (m, 6H). $^{13}C$ NMR (126 MHz, DMSO-$d_6$) δ ppm: 167.9, 166.3, 143.5, 140.1, 138.8, 138.0 (2C), 130.7, 128.7 (2C), 128.3 (2C), 123.2, 119.6 (2C), 100.4, 52.4, 49.9, 38.1, 38.0, 25.7, 22.4, 22.3. HRMS-ESI+ (m/z): calcd. for $C_{23}H_{28}IN_6O_5S$ $[M+H]^+$ 627.0887, found 627.0877.

N-[4-[[4-[[(7,7-Dimethyl-2-oxo-norbornan-1-yl)methylsulfonylamino]methyl]triazol-1-yl]methyl]phenyl]-2-(hydroxycarbamoyl)-4-methyl-pentanamide (Hit L2)

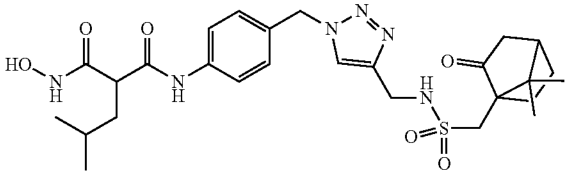 [SMILES: CC(C)CC(C(=O)NO)C(=O)Nc1ccc(Cn2cc(CNS(=O)(=O)CC34CCC(CC3=O)C4(C)C)nn2)cc1]

Hit L2 was synthesized according to the general procedure D, using ester 89 (127 mg, 0.22 mmol), KCN (2.85 mg, 0.04 mmol) and $NH_2OH$ (2 mL, 50% w/w in water) in MeOH (2 mL) overnight. The crude product was purified by flash chromatography on silica gel ($CH_2Cl_2$ to $CH_2Cl_2$/MeOH: 95/5) followed by preparative HPLC ($H_2O$+0.05% FA/ACN+0.05% FA: 95:5 to 5:95) affording compound Hit L2 as a white solid after lyophilization (13 mg, 10%). Purity: 100%, LC tr=3.57 min, MS (ESI+): m/z=575 $[M+H]^+$. $^1H$ NMR (500 MHz, DMSO-$d_6$) δ ppm: 10.52 (br s, 1H), 9.81 (s, 1H), 8.96 (s, 1H), 8.00 (s, 1H), 7.57-7.55 (m, 3H), 7.28-7.26 (m, 2H), 5.51 (s, 2H), 4.26-4.24 (m, 2H), 3.24-3.18 (m, 2H), 2.87-2.84 (m, 1H), 2.33-2.28 (m, 2H), 2.01 (t, J=4.4 Hz, 1H), 1.91-1.87 (m, 2H), 1.69-1.65 (m, 2H), 1.50-1.46 (m, 2H), 1.39-1.34 (m, 1H), 0.96 (s, 3H), 0.87 (d, J=6.6 Hz, 3H), 0.86 (d, J=6.6 Hz, 3H), 0.71 (s, 3H). $^{13}C$ NMR (126 MHz, DMSO-$d_6$) δ ppm: 214.6, 167.8, 168.3, 144.6, 138.7, 130.9, 128.6 (2C), 123.2, 119.5 (2C), 57.9, 52.4, 50.0, 48.6, 47.6, 42.0, 41.9, 38.0, 38.0, 26.3, 25.7, 24.5, 22.4, 22.3, 19.4, 19.2. HRMS-ESI+ (m/z): calcd. for $C_{27}H_{39}N_6O_6S$ $[M+H]^+$: 575.2652, found 575.2645.

2-(Hydroxycarbamoyl)-4-methyl-N-[4-[[4-[[(4-phenylphenyl)sulfonylamino]methyl]triazol-1-yl]methyl]phenyl]pentanamide (Hit L3)

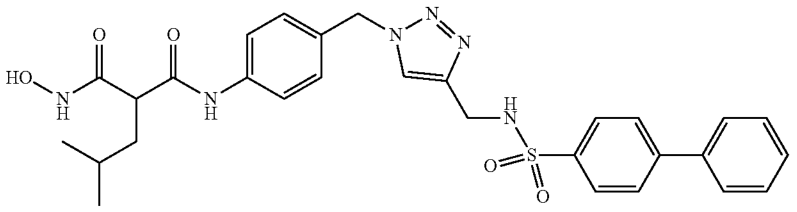 [SMILES: CC(C)CC(C(=O)NO)C(=O)Nc1ccc(Cn2cc(CNS(=O)(=O)c3ccc(-c4ccccc4)cc3)nn2)cc1]

Hit L3 was synthesized according to the general procedure D, using ester 90 (129 mg, 0.22 mmol), KCN (2.85 mg, 0.04 mmol) and $NH_2OH$ (2 mL, 50% w/w in water) in MeOH (2 mL) overnight. The crude product was purified by flash chromatography on silica gel ($CH_2Cl_2$ to $CH_2Cl_2$/MeOH: 95/5) affording compound Hit L3 as a white solid after lyophilization (42 mg, 32%). Purity: 100%, LC tr=4.02 min, MS (ESI+): m/z=577 $[M+H]^+$. $^1H$ NMR (500 MHz, DMSO-$d_6$) δ ppm: 10.52 (s, 1H), 9.82 (s, 1H), 8.97 (s, 1H), 7.62-7.59 (m, 2H), 7.32-7.30 (m, 2H), 4.37 (s, 2H), 3.22 (t, J=7.6 Hz, 1H), 1.69 (t, J=7.3 Hz, 2H), 1.49 (sep, J=6.7 Hz, 1H), 0.89 (d, J=2.0 Hz, 3H), 0.87 (d, J=2.0 Hz, 3H). $^{13}C$ NMR (126 MHz, DMSO-$d_6$) δ ppm: 167.9, 166.2, 143.9, 143.6, 139.1, 138.8, 138.5, 130.7, 129.2 (2C), 128.6 (2C), 128.5, 127.3 (2C), 127.3 (2C), 127.1 (2C), 123.2, 119.5 (2C), 52.4, 49.8, 38.2, 37.9, 25.7, 22.4, 22.3. HRMS-ESI+ (m/z): calcd. for $C_{29}H_{33}N_6O_5S$ $[M+H]^+$ 577.2233, found 577.2221.

N-[4-[[4-[3-(4-Fluorobenzoyl)thiazolidin-4-yl]triazol-1-yl]methyl]phenyl]-2-(hydroxycarbamoyl)-4-methyl-pentanamide (Hit L4)

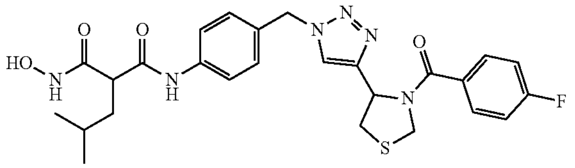 [SMILES: CC(C)CC(C(=O)NO)C(=O)Nc1ccc(Cn2cc(C3CSCN3C(=O)c3ccc(F)cc3)nn2)cc1]

Compound Hit L4 was synthesized according to the general procedure D, using ester 91 (154 mg, 0.28 mmol), KCN (3.7 mg, 0.06 mmol) and $NH_2OH$ (2.5 mL, 50% w/w in water) in MeOH (2.5 mL) overnight. The crude product was purified by flash chromatography on silica gel ($CH_2Cl_2$ to $CH_2Cl_2$/MeOH: 95/5) affording compound Hit L4 as a white solid after lyophilization (26 mg, 21%). Purity: 95%, LC tr=3.63 min, MS (ESI+): m/z=541 $[M+H]^+$. $^1H$ NMR (500 MHz, DMSO-$d_6$) δ ppm: 10.53 (s, 1H), 9.82 (s, 1H), 8.96 (s, 1H), 8.16 (s, 1H), 7.58-7.57 (m, 4H), 7.28-7.26 (m, 4H), 5.98-5.60 (m, 1H), 5.50 (s, 2H), 4.57 (br s, 2H), 3.44 (s, 1H), 3.22-3.21 (m, 2H), 1.69-1.66 (m, 2H), 1.50-1.44 (m, 1H), 1.23-0.97 (m, 1H), 0.88-0.86 (m, 6H). $^{13}C$ NMR (126 MHz, DMSO-$d_6$) δ ppm: 167.8, 167.7, 166.3, 163.0 (d, J=239.2 Hz), 146.7, 138.7, 130.8, 129.9 (d, J=11.9 Hz), 129.3, 128.6 (2C), 122.8 (2C), 119.6 (2C), 115.4 (d, J=21.9 Hz, 2C), 53.0, 52.5, 50.0, 38.0, 35.7, 25.7, 23.7, 22.4, 22.3. HRMS-ESI+ (m/z): calcd. for $C_{26}H_{30}FN_6O_4S$ $[M+H]^+$ 541.2033, found 541.2024.

N-[4-[[4-[(2-Acetamidophenoxy)methyl]triazol-1-yl]methyl]phenyl]-2-(hydroxycarbamoyl)-4-methyl-pentanamide (Hit L5)

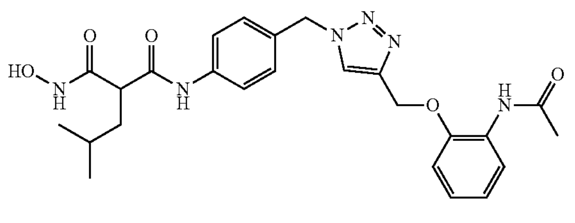 [SMILES: CC(=O)Nc1ccccc1OCc1cn(Cc2ccc(NC(=O)C(CC(C)C)C(=O)NO)cc2)nn1]

Hit L5 was synthesized according to the general procedure D, using ester 92 (66 mg, 0.13 mmol), KCN (1.7 mg, 0.03 mmol) and $NH_2OH$ (1.3 mL, 50% w/w in water) in MeOH (1.3 mL) overnight. The crude product was purified by preparative HPLC ($H_2O$+0.05% FA/ACN+0.05% FA: 95:5 to 5:95) affording compound Hit L5 as a white solid after lyophilization (18 mg, 27%). Purity: 100%, LC tr=3.30 min, MS (ESI+): m/z=495 $[M+H]^+$. $^1H$ NMR (500 MHz, DMSO-$d_6$) δ ppm: 10.51 (br s, 1H), 9.83 (s, 1H), 9.01 (s, 1H), 8.97 (br s, 1H), 8.22 (s, 1H), 7.86 (d, J=7.6 Hz, 1H), 7.57-7.56 (m, 2H), 7.27-7.25 (m, 2H), 7.20 (d, J=8.1 Hz, 1H), 7.04 (t, J=7.6 Hz, 1H), 6.90 (t, J=7.5 Hz, 1H), 5.54 (s, 2H), 5.20 (s, 2H), 3.21 (t, J=7.6 Hz, 1H), 2.03 (s, 3H), 1.67 (t, J=7.0 Hz, 2H), 1.47 (sep, J=6.6 Hz, 1H), 0.87 (d, J=6.5 Hz, 3H), 0.86 (d, J=6.5 Hz, 3H). $^{13}C$ NMR (126 MHz, DMSO-$d_6$) δ ppm: 168.4, 167.8, 166.2, 148.5, 143.1, 138.7, 130.8, 128.6 (2C), 127.9, 124.5, 124.3, 122.5, 120.8, 119.6 (2C), 113.3, 62.3, 52.5, 49.9, 38.0, 25.7, 23.9, 22.4, 22.3. HRMS-ESI+ (m/z): calcd. for $C_{25}H_{31}N_6O_5$ $[M+H]^+$ 495.2278, found 495.2352.

2-(Hydroxycarbamoyl)-N-[4-[[4-[[(4-iodophenyl) sulfonyl-methyl-amino]methyl]triazol-1-yl]methyl] phenyl]-4-methyl-pentanamide (131)

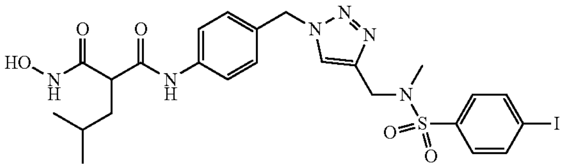 [SMILES: CC(C)CC(C(=O)NO)C(=O)Nc1ccc(Cn2cc(CN(C)S(=O)(=O)c3ccc(I)cc3)nn2)cc1]

Compound 131 was synthesized according to the general procedure D, using ester 123 (120 mg, 0.18 mmol), KCN (3.55 mg, 0.05 mmol) and $NH_2OH$ (2.5 mL, 50% w/w in water) in MeOH (2.5 mL) for 72 h. The crude product was purified by flash chromatography on silica gel ($CH_2Cl_2$ to $CH_2Cl_2$/MeOH: 95/5) affording compound 131 as a white solid after lyophilization (64 mg, 55%). Purity: 100%, LC tr=4.07 min, MS (ESI+): m/z=641 $[M+H]^+$. $^1H$ NMR (500 MHz, DMSO-$d_6$) δ ppm: 10.52 (s, 1H), 9.81 (s, 1H), 8.97 (s, 1H), 8.03 (s, 1H), 7.96-7.94 (m, 2H), 7.59-7.57 (m, 2H), 7.52-7.51 (m, 2H), 7.26-7.24 (m, 2H), 5.48 (s, 2H), 4.26 (s, 2H), 3.20 (t, J=7.6 Hz, 1H), 2.63 (s, 3H), 1.68 (t, J=7.3 Hz, 2H), 1.47 (sep, J=6.6 Hz, 1H), 0.87 (d, J=6.5 Hz, 3H), 0.86 (d, J=6.5 Hz, 3H). $^{13}C$ NMR (126 MHz, DMSO-$d_6$) δ ppm: 167.8, 166.3, 141.8, 138.7, 138.2 (2C), 136.5, 130.7, 128.9 (2C), 128.6 (2C), 124.0, 119.6 (2C), 101.3, 52.5, 50.0, 44.7, 38.0, 34.7, 25.7, 22.4, 22.3. HRMS-ESI+ (m/z): calcd. for $C_{24}H_{30}IN_6O_5S$ $[M+H]^+$ 641.1043, found 641.1033.

N-[[1-[[4-[[2-(Hydroxycarbamoyl)-4-methyl-pentanoyl]amino]phenyl]methyl]triazol-4-yl]methyl]-4-iodo-benzamide (132)

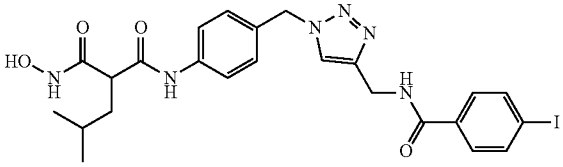 [SMILES: CC(C)CC(C(=O)NO)C(=O)Nc1ccc(Cn2cc(CNC(=O)c3ccc(I)cc3)nn2)cc1]

Compound 132 was synthesized according to the general procedure D, using ester 124 (132 mg, 0.22 mmol), KCN (4.23 mg, 0.07 mmol) and $NH_2OH$ (2 mL, 50% w/w in water) in MeOH (2 mL) for 72 h. The crude product was purified by flash chromatography on silica gel ($CH_2Cl_2$ to $CH_2Cl_2$/MeOH: 9/1) affording compound 132 as a white solid after lyophilization (53 mg, 41%). Purity: 100%, LC tr=3.73 min, MS (ESI+): m/z=591 $[M+H]^+$. $^1H$ NMR (500 MHz, DMSO-$d_6$) δ ppm: 10.52 (s, 1H), 9.80 (s, 1H), 9.05 (t, J=7.1 Hz, 1H), 8.97 (s, 1H), 7.97 (s, 1H), 7.85-7.83 (m, 2H), 7.64-7.63 (m, 2H), 7.56-7.54 (m, 2H), 7.28-7.26 (m, 2H), 5.48 (s, 2H), 4.47 (d, J=4.3 Hz, 2H), 3.20 (t, J=6.6 Hz, 1H), 1.67 (t, J=7.3 Hz, 2H), 1.49-1.44 (m, 1H), 0.88-0.85 (m, 6H). $^{13}C$ NMR (126 MHz, DMSO-$d_6$) δ ppm: 167.8, 166.3, 165.5, 145.1, 138.7, 137.2 (2C), 133.5, 131.0, 129.3 (2C), 128.7 (2C), 122.9, 119.6 (2C), 99.0, 52.4, 49.9, 38.0, 34.9, 25.7, 22.4, 22.3. HRMS-ESI+ (m/z): calcd. for $C_{24}H_{28}IN_6O_4$ $[M+H]^+$ 591.1217, found 591.1208.

Tert-butyl N-[[1-[[4-[[2-(hydroxycarbamoyl)-4-methyl-pentanoyl]amino]phenyl]methyl]triazol-4-yl] methyl]carbamate (133)

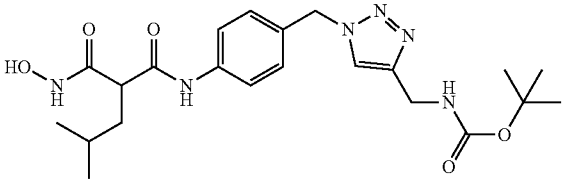 [SMILES: CC(C)CC(C(=O)NO)C(=O)Nc1ccc(Cn2cc(CNC(=O)OC(C)(C)C)nn2)cc1]

Compound 133 was synthesized according to the general procedure D, using ester 125 (105 mg, 0.22 mmol), KCN (4.29 mg, 0.07 mmol) and $NH_2OH$ (2.3 mL, 50% w/w in water) in MeOH (2.3 mL) for 48 h. The crude product was purified by preparative HPLC ($H_2O$+0.05% FA/ACN+0.05% FA: 95:5 to 5:95) affording compound 133 as a white solid after lyophilization (36 mg, 35%). Purity: 100%, LC tr=3.41 min, MS (ESI+): m/z=921 $[2M+H]^+$, 461 $[M+H]^+$, 405 $[M-tBu+H]^+$, 361 $[M-Boc+H]^+$. $^1H$ NMR (500 MHz, DMSO-$d_6$) δ ppm: 10.54 (s, 1H), 9.83 (s, 1H), 8.99 (s, 1H), 7.87 (s, 1H), 7.57-7.55 (m, 2H), 7.31 (t, J=5.8 Hz, 1H), 7.26-7.25 (m, 2H), 5.49 (s, 2H), 4.13 (d, J=5.9 Hz, 2H), 3.20 (t, J=7.6 Hz, 1H), 1.67 (t, J=7.3 Hz, 2H), 1.46 (sep, J=6.6 Hz, 1H), 1.36 (s, 9H), 0.87 (d, J=6.5 Hz, 3H), 0.86 (d, J=6.5 Hz, 3H). $^{13}C$ NMR (126 MHz, DMSO-$d_6$) δ ppm: 167.9, 166.3, 155.6, 145.9, 138.7, 131.0, 128.6 (2C), 122.6, 119.5 (2C), 77.9, 52.3, 50.0, 38.0, 35.7, 28.3 (3C), 25.7, 22.4, 22.3. HRMS-ESI+ (m/z): calcd. for $C_{22}H_{33}N_6O_5$ $[M+H]^+$ 461.2512, found 461.2480.

2-(Hydroxycarbamoyl)-N-[4-[[4-[(4-iodoanilino)methyl]triazol-1-yl]methyl]phenyl]-4-methyl-pentanamide (134)

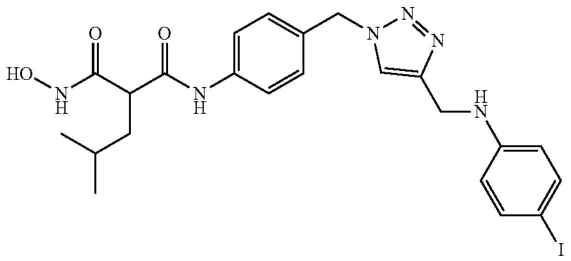 [SMILES: CC(C)CC(C(=O)NO)C(=O)Nc1ccc(Cn2cc(CNc3ccc(I)cc3)nn2)cc1]

Compound 134 was synthesized according to the general procedure D, using ester 126 (158 mg, 0.27 mmol), KCN (5.31 mg, 0.08 mmol) and $NH_2OH$ (2.5 mL, 50% w/w in water) in MeOH (2.5 mL) for 72 h. The crude product was purified by flash chromatography on silica gel ($CH_2Cl_2$ to $CH_2Cl_2$/MeOH: 9/1) affording compound 134 as a white solid after lyophilization (31 mg, 20%). Purity: 100%, LC tr=4.13 min, MS (ESI+): m/z=563 $[M+H]^+$. $^1H$ NMR (500 MHz, DMSO-$d_6$) δ ppm: 10.52 (s, 1H), 9.80 (s, 1H), 8.97 (s, 1H), 7.94 (s, 1H), 7.56-7.54 (m, 2H), 7.33-7.31 (m, 2H), 7.26-7.24 (m, 2H), 6.49-6.47 (m, 2H), 6.27 (t, J=5.8 Hz, 1H), 5.48 (s, 2H), 4.24 (d, J=5.8 Hz, 2H), 3.20 (t, J=7.6 Hz, 1H), 1.67 (t, J=7.2 Hz, 2H), 1.47 (sep, J=6.7 Hz, 1H), 0.87 (d, J=6.6 Hz, 3H), 0.86 (d, J=6.6 Hz, 3H). $^{13}C$ NMR (126 MHz, DMSO-$d_6$) δ ppm: 167.8, 166.1, 148.1, 145.5, 138.6, 137.1 (2C), 131.0, 128.6 (2C), 122.7, 119.6 (2C), 115.0 (2C), 76.5, 52.4, 49.9, 38.3, 38.0, 25.7, 22.4, 22.3. HRMS-ESI+(m/z): calcd. for $C_{23}H_{28}IN_6O_3$ $[M+H]^+$ 563.1268, found 563.1232.

N-[4-[[4-[(4-Chlorophenoxy)methyl]triazol-1-yl]methyl]phenyl]-2-(hydroxycarbamoyl)-4-methyl-pentanamide (135)

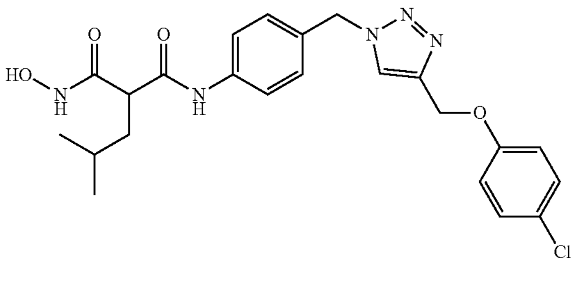

Compound 135 was synthesized according to the general procedure D, using ester 127 (50 mg, 0.1 mmol), KCN (2.0 mg, 0.03 mmol) and $NH_2OH$ (1.5 mL, 50% w/w in water) in MeOH (1.5 mL) for 72 h. The crude product was purified by preparative HPLC ($H_2O$+0.05% FA/ACN+0.05% FA: 95:5 to 5:95) affording compound 135 as a white solid after lyophilization (21 mg, 43%). Purity: 100%, LC tr=4.13 min, MS (ESI+): m/z=472 and 474 $[M+H]^+$. $^1H$ NMR (500 MHz, DMSO-$d_6$) δ ppm: 10.53 (s, 1H), 9.83 (s, 1H), 8.97 (s, 1H), 8.23 (s, 1H), 7.58-7.56 (m, 2H), 7.33-7.32 (m, 2H), 7.29-7.27 (m, 2H), 7.06-7.04 (m, 2H), 5.53 (s, 2H), 5.11 (s, 2H), 3.21 (t, J=7.6 Hz, 1H), 1.69-1.67 (m, 2H), 1.47 (sep, J=6.7 Hz, 1H), 0.87 (d, J=6.6 Hz, 3H), 0.86 (d, J=6.6 Hz, 3H). $^{13}C$ NMR (126 MHz, DMSO-$d_6$) δ ppm: 167.8, 166.3, 156.9, 142.7, 138.7, 130.8, 129.2 (2C), 128.7 (2C), 124.6, 124.6, 119.6 (2C), 116.5 (2C), 61.4, 52.5, 49.9, 38.0, 25.7, 22.4, 22.3. HRMS-ESI+ (m/z): calcd. for $C_{23}H_{27}ClN_5O_4$ $[M+H]^+$ 472.1752, found 472.1718.

N-[4-[[4-[(4-Chlorophenyl)sulfanylmethyl]triazol-1-yl]methyl]phenyl]-2-(hydroxycarbamoyl)-4-methyl-pentanamide (136)

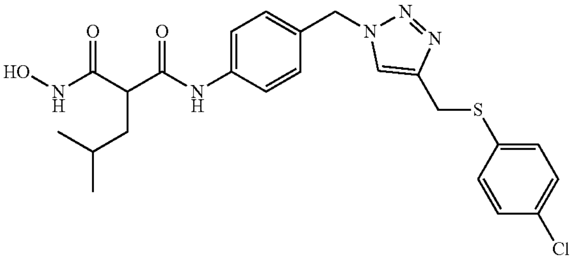 [SMILES: CC(C)CC(C(=O)NO)C(=O)Nc1ccc(Cn2cc(COc3ccc(Cl)cc3)nn2)cc1]

Compound 136 was synthesized according to the general procedure D, using ester 128 (70 mg, 0.14 mmol), KCN (2.7 mg, 0.04 mmol) and $NH_2OH$ (1.5 mL, 50% w/w in water) in MeOH (1.5 mL) for 72 h. The crude product was purified by preparative HPLC ($H_2O$+0.05% FA/ACN+0.05% FA: 95:5 to 5:95) affording compound 136 as a white solid after lyophilization (11 mg, 15%). Purity: 95%, LC tr=4.13 min, MS (ESI+): m/z=488 and 490 $[M+H]^+$. $^1H$ NMR (500 MHz, DMSO-$d_6$) δ ppm: 10.55 (s, 1H), 9.83 (s, 1H), 8.97 (br s, 1H), 7.93 (s, 1H), 7.56-7.54 (m, 2H), 7.36-7.32 (m, 4H), 7.19-7.18 (m, 2H), 5.46 (s, 2H), 4.27 (s, 2H), 3.21 (t, J=7.6 Hz, 1H), 1.69-1.66 (m, 2H), 1.47 (sep, J=6.6 Hz, 1H), 0.87 (d, J=6.6 Hz, 3H), 0.86 (d, J=6.6 Hz, 3H). $^{13}C$ NMR (126 MHz, DMSO-$d_6$) δ ppm: 167.8, 166.3, 143.5, 138.7, 134.7, 130.8, 130.6, 130.2 (2C), 128.8 (2C), 128.4 (2C), 123.3, 119.5 (2C), 52.4, 49.9, 38.0, 27.3, 25.7, 22.4, 22.3. HRMS-ESI+ (m/z): calcd. for $C_{23}H_{27}ClN_5O_3S$ $[M+H]^+$ 488.1523, found 488.1490.

N-[4-[[4-[(4-Chlorophenyl)methyl]triazol-1-yl]methyl]phenyl]-2-(hydroxycarbamoyl)-4-methyl-pentanamide (137)

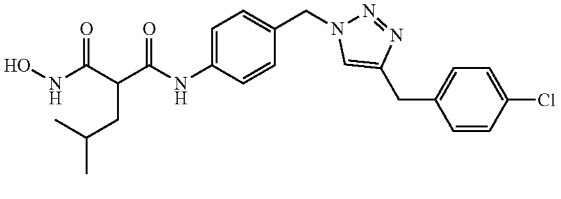 [SMILES: CC(C)CC(C(=O)NO)C(=O)Nc1ccc(Cn2cc(Cc3ccc(Cl)cc3)nn2)cc1]

Compound 137 was synthesized according to the general procedure D, using ester 129 (75 mg, 0.16 mmol), KCN (3.1 mg, 0.05 mmol) and $NH_2OH$ (1.5 mL, 50% w/w in water) in MeOH (1.5 mL) for 72 h. The crude product was purified by preparative HPLC ($H_2O$+0.05% FA/ACN+0.05% FA: 95:5 to 5:95) affording compound 137 as a white solid after lyophilization (11 mg, 15%). Purity: 100%, LC tr=4.04 min, MS (ESI+): m/z=456 and 458 $[M+H]^+$. $^1H$ NMR (500 MHz, DMSO-$d_6$) δ ppm: 10.53 (br s, 1H), 9.81 (s, 1H), 8.97 (br s, 1H), 7.84 (s, 1H), 7.56-7.54 (m, 2H), 7.34-7.32 (m, 2H), 7.26-7.24 (m, 4H), 5.46 (s, 2H), 3.96 (s, 2H), 3.20 (t, J=7.6

Hz, 1H), 1.67 (t, J=7.0 Hz, 2H), 1.47 (sep, J=6.7 Hz, 1H), 0.87 (d, J=6.6 Hz, 3H), 0.86 (d, J=6.6 Hz, 3H). $^{13}$C NMR (126 MHz, DMSO-$d_6$) δ ppm: 167.8, 166.3, 146.0, 138.7, 138.6, 130.9, 130.8, 130.4 (2C), 128.6 (2C), 128.3 (2C), 122.5, 119.5 (2C), 52.4, 49.9, 38.0, 30.5, 25.7, 22.4, 22.3. HRMS-ESI+ (m/z): calcd. for $C_{23}H_{27}ClN_5O_3$ [M+H]$^+$ 456.1802, found 456.1773.

2-(Hydroxycarbamoyl)-N-[4-[[4-(4-iodophenyl)triazol-1-yl]methyl]phenyl]-4-methyl-pentanamide (138)

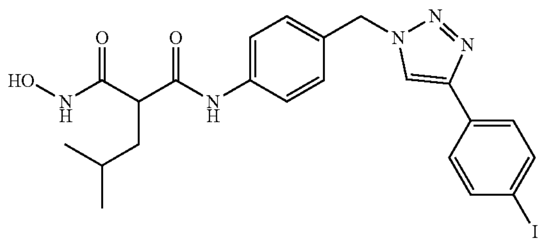 [SMILES: CC(C)CC(C(=O)NO)C(=O)Nc1ccc(Cn2cc(-c3ccc(I)cc3)nn2)cc1]

Compound 138 was synthesized according to the general procedure D, using ester 130 (140 mg, 0.25 mmol), KCN (4.96 mg, 0.08 mmol) and $NH_2OH$ (2.5 mL, 50% w/w in water) in MeOH (2.5 mL) for 72 h. The crude product was purified by flash chromatography on silica gel ($CH_2Cl_2$ to $CH_2Cl_2$/MeOH: 95/5) affording compound 138 as a white solid after lyophilization (28 mg, 20%). Purity: 100%, LC tr=4.31 min, MS (ESI+): m/z=534 [M+H]$^+$. $^1$H NMR (500 MHz, DMSO-$d_6$) δ ppm: 10.52 (br s, 1H), 9.83 (s, 1H), 8.98 (br s, 1H), 8.63 (s, 1H), 7.81-7.79 (m, 2H), 7.67-7.59 (m, 4H), 7.33-7.32 (m, 2H), 5.58 (s, 2H), 3.20 (t, J=7.3 Hz, 1H), 1.67 (t, J=6.9 Hz, 2H), 1.51-1.43 (m, 1H), 0.88-0.85 (m, 6H). $^{13}$C NMR (126 MHz, DMSO-$d_6$) δ ppm: 167.9, 166.3, 145.7, 138.8, 137.7 (2C), 130.6, 130.3, 128.7 (2C), 127.2 (2C), 121.7, 119.6 (2C), 93.8, 52.7, 50.0, 38.0, 25.7, 22.4, 22.3. HRMS-ESI+ (m/z): calcd. for $C_{22}H_{25}IN_5O_3$ [M+H]$^+$ 534.1002, found 534.0970.

2-(Hydroxycarbamoyl)-N-[3-[[4-[[(4-iodophenyl) sulfonylamino]methyl]triazol-1-yl]methyl]phenyl]-4-methyl-pentanamide (114)

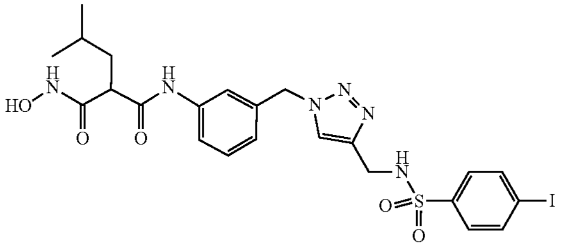 [SMILES: CC(C)CC(C(=O)NO)C(=O)Nc1cccc(Cn2cc(CNS(=O)(=O)c3ccc(I)cc3)nn2)c1]

Compound 114 was synthesized according to the general procedure D, using ester 113 (206 mg, 0.32 mmol), KCN (4.15 mg, 0.06 mmol) and $NH_2OH$ (3.5 mL, 50% w/w in water) in MeOH (3.5 mL) for 96 h. The crude product was purified by flash chromatography on silica gel ($CH_2Cl_2$ to $CH_2Cl_2$/MeOH: 95/5) affording compound 114 as a white solid after lyophilization (13 mg, 6%). Purity: 95%, LC tr=3.84 min, MS (ES+): m/z=627 [M+H]$^+$. $^1$H NMR (500 MHz, DMSO-$d_6$) δ ppm: 10.52 (br s, 1H), 9.83 (s, 1H), 8.96 (s, 1H), 8.21 (br s, 1H), 7.94-7.92 (m, 2H), 7.89 (s, 1H), 7.56-7.51 (m, 4H), 7.32-7.29 (m, 1H), 6.96-6.95 (m, 1H), 5.49 (s, 2H), 4.04 (s, 2H), 3.21 (t, J=7.5 Hz, 1H), 1.70-1.64 (m, 2H), 1.47 (sep, J=6.6 Hz, 1H), 0.87 (d, J=6.4 Hz, 3H), 0.86 (d, J=6.4 Hz, 3H). $^{13}$C NMR (126 MHz, DMSO-$d_6$) δ ppm: 167.8, 166.3, 143.5, 140.0, 139.1, 138.0 (2C), 136.4, 129.2, 128.3 (2C), 123.4, 123.0, 119.1, 118.9, 100.4, 52.7, 49.9, 38.0, 37.9, 25.7, 22.4, 22.3. HRMS-ESI+ (m/z): calcd. for $C_{23}H_{28}IN_6O_5S$ [M+H]$^+$627.0887, found 627.0879.

N-[4-[[4-[[(4-Fluorophenyl)sulfonylamino]methyl] triazol-1-yl]methyl]phenyl]-2-(hydroxycarbamoyl)-4-methyl-pentanamide (160)

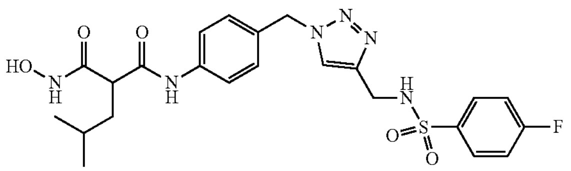 [SMILES: CC(C)CC(C(=O)NO)C(=O)Nc1ccc(Cn2cc(CNS(=O)(=O)c3ccc(F)cc3)nn2)cc1]

Compound 160 was synthesized according to the general procedure D, using ester 150 (127 mg, 0.23 mmol), KCN (4.62 mg, 0.07 mmol) and $NH_2OH$ (3 mL, 50% w/w in water) in MeOH (3 mL) for 72 h. The crude product was purified by flash chromatography on silica gel ($CH_2Cl_2$ to $CH_2Cl_2$/MeOH: 95/5) affording compound 160 as a white solid after lyophilization (96 mg, 78%). Purity: 100%, LC tr=3.46 min, MS (ESI+): m/z=519 [M+H]$^+$. $^1$H NMR (500 MHz, DMSO-$d_6$) δ ppm: 10.51 (br s, 1H), 9.83 (s, 1H), 8.97 (br s, 1H), 8.19 (br s, 1H), 7.84 (s, 1H), 7.82-7.79 (m, 2H), 7.57-7.56 (m, 2H), 7.38-7.34 (m, 2H), 7.23-7.22 (m, 2H), 5.45 (s, 2H), 4.04 (s, 2H), 3.21 (t, J=7.5 Hz, 1H), 1.68 (t, J=7.2 Hz, 2H), 1.47 (sep, J=6.6 Hz, 1H), 0.87 (d, J=6.3 Hz, 3H), 0.86 (d, J=6.3 Hz, 3H). $^{13}$C NMR (126 MHz, DMSO-$d_6$) δ ppm: 167.8, 166.3, 164.1 (d, J=250.8 Hz), 143.5, 138.7, 136.8 (d, J=2.8 Hz), 130.7, 129.6 (d, J=9.2 Hz, 2C), 128.6 (2C), 123.2, 119.6 (2C), 116.2 (d, J=22.8 Hz, 2C), 52.4, 49.9, 38.1, 38.0, 25.7, 22.4, 22.3. HRMS-ESI+ (m/z): calcd. for $C_{23}H_{28}FN_6O_5S$ [M+H]$^+$: 519.1826, found 519.1819.

N-[4-[[4-[[(4-Chlorophenyl)sulfonylamino]methyl] triazol-1-yl]methyl]phenyl]-2-(hydroxycarbamoyl)-4-methyl-pentanamide (161)

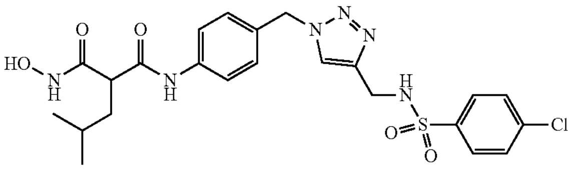 [SMILES: CC(C)CC(C(=O)NO)C(=O)Nc1ccc(Cn2cc(CNS(=O)(=O)c3ccc(Cl)cc3)nn2)cc1]

Compound 161 was synthesized according to the general procedure D, using ester 151 (128 mg, 0.23 mmol), KCN (4.52 mg, 0.07 mmol) and $NH_2OH$ (2.8 mL, 50% w/w in water) in MeOH (2.8 mL) for 72 h. The crude product was purified by flash chromatography on silica gel ($CH_2Cl_2$ to $CH_2Cl_2$/MeOH: 9/1) affording compound 161 as a white solid after lyophilization (59 mg, 47%). Purity: 100%, LC tr=3.64 min, MS (ESI+): m/z=535 and 537 [M+H]$^+$. $^1$H NMR (500 MHz, DMSO-$d_6$) δ ppm: 10.53 (s, 1H), 9.81 (s, 1H), 8.98 (s, 1H), 8.22 (t, J=6.0 Hz, 1H), 7.85 (s, 1H), 7.75-7.73 (m, 2H), 7.60-7.56 (m, 4H), 7.24-7.22 (m, 2H), 5.44 (s, 2H), 4.05 (d, J=3.6 Hz, 2H), 3.21 (t, J=7.5 Hz, 1H), 1.68 (t, J=6.9 Hz, 2H), 1.47 (sep, J=6.6 Hz, 1H), 0.88-0.86 (m, 6H). $^{13}C$ NMR (126 MHz, DMSO-$d_6$) δ ppm: 169.7, 167.1, 143.4, 139.3, 138.7, 137.2, 130.9, 129.2 (2C), 128.8 (2C), 128.5 (2C), 123.2, 119.4 (2C), 52.3, 50.9, 38.0, 37.4, 25.6, 22.6, 21.9. HRMS-ESI+ (m/z): calcd. for $C_{23}H_{28}ClN_6O_5S$ $[M+H]^+$ 535.1530, found 535.1526.

2-(Hydroxycarbamoyl)-N-[4-[[4-[[(4-methoxyphenyl)sulfonylamino]methyl]triazol-1-yl]methyl]phenyl]-4-methyl-pentanamide (162)

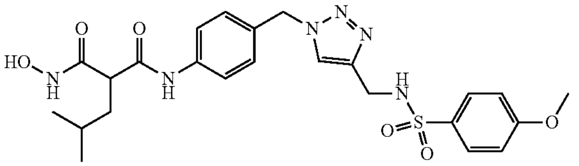 [SMILES: COc1ccc(S(=O)(=O)NCc2cn(Cc3ccc(NC(=O)C(CC(C)C)C(=O)NO)cc3)nn2)cc1]

Compound 162 was synthesized according to the general procedure D, using ester 152 (131 mg, 0.24 mmol), KCN (4.66 mg, 0.07 mmol) and $NH_2OH$ (3 mL, 50% w/w in water) in MeOH (3 mL) for 72 h. The crude product was purified by flash chromatography on silica gel ($CH_2Cl_2$ to $CH_2Cl_2$/MeOH: 9/1) affording compound 162 as a white solid after lyophilization (34 mg, 26%). Purity: 100%, LC tr=3.43 min, MS (ESI+): m/z=531 $[M+H]^+$. Purity: 100%, LC tr=3.43 min, MS (ESI+): m/z=531 $[M+H]^+$. $^1H$ NMR (500 MHz, DMSO-$d_6$) δ ppm: 10.53 (br s, 1H), 9.83 (s, 1H), 8.97 (br s, 1H), 7.92 (br s, 1H), 7.84 (s, 1H), 7.71-7.69 (m, 2H), 7.57-7.56 (m, 2H), 7.24-7.22 (m, 2H), 7.07-7.05 (m, 2H), 5.45 (s, 2H), 3.98 (s, 2H), 3.82 (s, 3H), 3.21 (t, J=7.6 Hz, 1H), 1.68 (t, J=7.2 Hz, 2H), 1.47 (sep, J=6.6 Hz, 1H), 0.88-0.86 (m, 6H). $^{13}C$ NMR (126 MHz, DMSO-$d_6$) δ ppm: 167.8, 166.3, 162.1, 143.7, 138.7, 131.9, 130.8, 128.7 (2C), 128.6 (2C), 123.2, 119.5 (2C), 114.3 (2C), 55.6, 52.4, 49.9, 38.1, 38.0, 25.7, 22.4, 22.3. HRMS-ESI+ (m/z): calcd. for $C_{24}H_{31}N_6O_6S$ $[M+H]^+$: 531.2026, found 531.1997.

N-[4-[[4-[[(2-Chlorophenyl)sulfonylamino]methyl]triazol-1-yl]methyl]phenyl]-2-(hydroxycarbamoyl)-4-methyl-pentanamide (163)

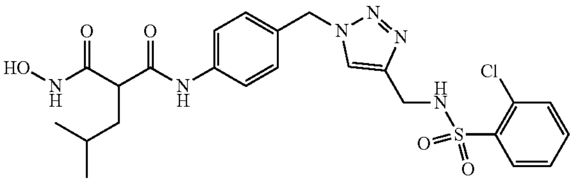 [SMILES: CC(C)CC(C(=O)NO)C(=O)Nc1ccc(Cn2cc(CNS(=O)(=O)c3ccccc3Cl)nn2)cc1]

Compound 163 was synthesized according to the general procedure D, using ester 153 (160 mg, 0.29 mmol), KCN (5.65 mg, 0.09 mmol) and $NH_2OH$ (3 mL, 50% w/w in water) in MeOH (3 mL) for 72 h. The crude product was purified by flash chromatography on silica gel ($CH_2Cl_2$ to $CH_2Cl_2$/MeOH: 9/1) affording compound 163 as a white solid after lyophilization (12 mg, 7%). Purity: 100%, LC tr=3.43 min, MS (ESI+): m/z=535 and 537 $[M+H]^+$. $^1H$ NMR (DMSO-$d_6$) δ ppm: 10.55 (br s, 1H), 9.84 (s, 1H), 8.99 (br s, 1H), 8.37 (br s, 1H), 7.90-7.89 (m, 1H), 7.74 (s, 1H), 7.59-7.57 (m, 2H), 7.55-7.49 (m, 2H), 7.45-7.42 (m, 1H), 7.22-7.21 (m, 2H), 5.42 (s, 2H), 4.16 (s, 2H), 3.22 (t, J=7.6 Hz, 1H), 1.69 (t, J=7.0 Hz, 2H), 1.49 (sep, J=6.6 Hz, 1H), 0.89 (d, J=6.4 Hz, 3H), 0.88 (d, J=6.4 Hz, 3H). $^{13}C$ NMR (126 MHz, DMSO-$d_6$) δ ppm: 167.9, 166.3, 143.7, 138.7, 138.0, 133.9, 131.6, 130.8, 130.6, 130.4, 128.7 (2C), 127.5, 123.1, 119.6 (2C), 52.3, 50.0, 38.0, 37.9, 25.8, 22.5, 22.3. HRMS-ESI+ (m/z): calcd. for $C_{23}H_{28}ClN_6O_5S$ $[M+H]^+$ 535.1530, found 535.1500.

N-[4-[[4-[[(3-Chlorophenyl)sulfonylamino]methyl]triazol-1-yl]methyl]phenyl]-2-(hydroxycarbamoyl)-4-methyl-pentanamide (164)

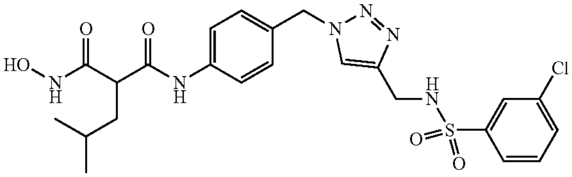 [SMILES: CC(C)CC(C(=O)NO)C(=O)Nc1ccc(Cn2cc(CNS(=O)(=O)c3cccc(Cl)c3)nn2)cc1]

Compound 164 was synthesized according to the general procedure D, using ester 154 (125 mg, 0.23 mmol), KCN (4.41 mg, 0.07 mmol) and $NH_2OH$ (2.5 mL, 50% w/w in water) in MeOH (2.5 mL) for 72 h. The crude product was purified by flash chromatography on silica gel ($CH_2Cl_2$ to $CH_2Cl_2$/MeOH: 9/1) affording compound 164 as a white solid after lyophilization (67 mg, 55%). Purity: 100%, LC tr=3.66 min, MS (ESI+): m/z=535 and 537 $[M+H]^+$. $^1H$ NMR (500 MHz, DMSO-$d_6$) δ ppm: 10.53 (br s, 1H), 9.82 (s, 1H), 8.98 (s, 1H), 8.29 (br s, 1H), 7.84 (s, 1H), 7.75-7.74 (m, 1H), 7.70-7.66 (m, 2H), 7.58-7.55 (m, 3H), 7.24-7.22 (m, 2H), 5.45 (s, 2H), 4.09 (s, 2H), 3.21 (t, J=7.6 Hz, 1H), 1.71-1.67 (m, 2H), 1.48 (sep, J=6.7 Hz, 1H), 0.88 (d, J=6.6 Hz, 3H), 0.87 (d, J=6.6 Hz, 3H). $^{13}C$ NMR (126 MHz, DMSO-$d_6$) δ ppm: 167.9, 166.3, 143.3, 142.4, 138.8, 133.7, 132.4, 131.2, 130.7, 128.7 (2C), 126.2, 125.2, 123.2, 119.6 (2C), 52.4, 50.0, 38.1, 38.0, 25.8, 22.4, 22.3. HRMS-ESI+ (m/z): calcd. for $C_{23}H_{28}ClN_6O_5S$ $[M+H]^+$ 535.1530, found 535.1496.

N-[4-[[4-[[(3,4-Dichlorophenyl)sulfonylamino]methyl]triazol-1-yl]methyl]phenyl]-2-(hydroxycarbamoyl)-4-methyl-pentanamide (165)

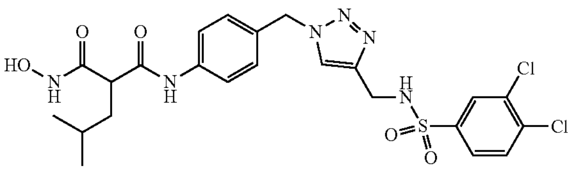 [SMILES: CC(C)CC(C(=O)NO)C(=O)Nc1ccc(Cn2cc(CNS(=O)(=O)c3ccc(Cl)c(Cl)c3)nn2)cc1]

Compound 165 was synthesized according to the general procedure D, using ester 155 (108 mg, 0.18 mmol), KCN (3.59 mg, 0.06 mmol) and $NH_2OH$ (1.8 mL, 50% w/w in water) in MeOH (1.8 mL) for 72 h. The crude product was purified by flash chromatography on silica gel ($CH_2Cl_2$ to $CH_2Cl_2$/MeOH: 95/5) affording compound 165 as a white solid after lyophilization (19 mg, 18%). Purity: 95%, LC tr=3.94 min, MS (ESI−): m/z=569, 571 and 573 $[M+H]^+$. $^1H$ NMR (500 MHz, DMSO-$d_6$) δ ppm: 10.54 (br s, 1H), 9.82 (s, 1H), 8.97 (s, 1H), 8.35 (br s, 1H), 7.91-7.90 (m, 1H), 7.88 (s, 1H), 7.79-7.78 (m, 1H), 7.68-7.67 (m, 1H), 7.58-7.56 (m, 2H), 7.24-7.22 (m, 2H), 5.44 (s, 2H), 4.10 (s, 2H), 3.21 (t, J=7.6 Hz, 1H), 1.69-1.66 (m, 2H), 1.47 (sep, J=6.7 Hz, 1H), 0.87 (d, J=6.6 Hz, 3H), 0.86 (d, J=6.6 Hz, 3H). $^{13}C$ NMR (126 MHz, DMSO-$d_6$) δ ppm: 167.8, 166.3, 143.2, 140.9, 138.7, 135.4, 131.9, 131.5, 130.7, 128.6 (2C), 128.4, 126.7, 123.3, 119.9 (2C), 52.4, 50.0, 38.0, 38.0, 25.7, 22.4, 22.3. HRMS-ESI+(m/z): calcd. for $C_{23}H_{27}Cl_2N_6O_5S$ $[M+H]^+$ 569.1141, found 569.1099.

N-[4-[[4-[[(4-Chlorophenyl)methylsulfonylamino]methyl]triazol-1-yl]methyl]phenyl]-2-(hydroxycarbamoyl)-4-methyl-pentanamide (166)

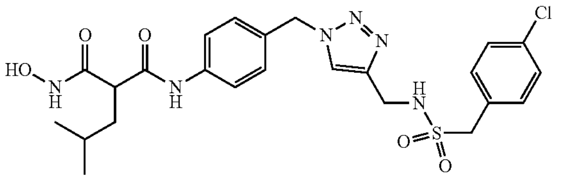 [SMILES: CC(C)CC(C(=O)NO)C(=O)Nc1ccc(Cn2cc(CNS(=O)(=O)Cc3ccc(Cl)cc3)nn2)cc1]

Compound 166 was synthesized according to the general procedure D, using ester 156 (58 mg, 0.1 mmol), KCN (2 mg, 0.03 mmol) and $NH_2OH$ (1.2 mL, 50% w/w in water) in MeOH (1.2 mL) for 72 h. The crude product was purified by flash chromatography on silica gel ($CH_2Cl_2$ to $CH_2Cl_2$/MeOH: 9/1) affording compound 166 as a white solid after lyophilization (13 mg, 23%). Purity: 100%, LC tr=3.74 min, MS (ESI+): m/z=549 and 551 $[M+H]^+$. $^1H$ NMR (500 MHz, DMSO-$d_6$) δ ppm: 10.52 (s, 1H), 9.81 (s, 1H), 8.97 (s, 1H), 7.97 (s, 1H), 7.64 (t, J=5.9 Hz, 1H), 7.58-7.56 (m, 2H), 7.38-7.37 (m, 2H), 7.30-7.28 (m, 4H), 5.52 (s, 2H), 4.34 (s, 2H), 4.17 (d, J=5.8 Hz, 2H), 3.20 (t, J=7.6 Hz, 1H), 1.67 (t, J=6.2 Hz, 2H), 1.47 (sep, J=6.6 Hz, 1H), 0.87 (d, J=6.4 Hz, 3H), 0.86 (d, J=6.4 Hz, 3H). $^{13}C$ NMR (126 MHz, DMSO-$d_6$) δ ppm: 167.8, 166.3, 148.7, 138.7, 132.9, 132.5 (2C), 130.9, 129.3, 128.7 (2C), 128.3 (2C), 123.2, 119.5 (2C), 56.7, 52.4, 49.9, 38.0, 38.0, 25.7, 22.4, 22.2. HRMS-ESI+ (m/z): calcd. for $C_{24}H_{30}ClN_6O_5S$ $[M+H]^+$ 549.1687, found 549.1653.

N-[4-[[4-(Benzenesulfonamidomethyl)triazol-1-yl]methyl]phenyl]-2-(hydroxycarbamoyl)-4-methyl-pentanamide (167)

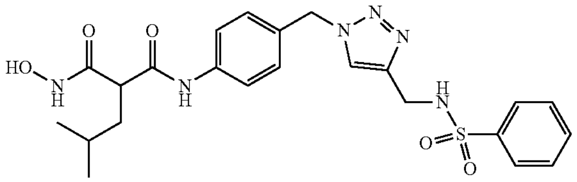 [SMILES: CC(C)CC(C(=O)NO)C(=O)Nc1ccc(Cn2cc(CNS(=O)(=O)c3ccccc3)nn2)cc1]

Compound 167 was synthesized according to the general procedure D, using ester 157 (113 mg, 0.22 mmol), KCN (4.25 mg, 0.07 mmol) and $NH_2OH$ (2.5 mL, 50% w/w in water) in MeOH (2.5 mL) for 72 h. The crude product was purified by flash chromatography on silica gel ($CH_2Cl_2$ to $CH_2Cl_2$/MeOH: 9/1) affording compound 167 as a white solid after lyophilization (19 mg, 17%). Purity: 100%, LC tr=3.36 min, MS (ESI+): m/z=501 $[M+H]^+$. $^1H$ NMR (500 MHz, DMSO-$d_6$) δ ppm: 10.50 (br s, 1H), 9.83 (s, 1H), 8.96 (br s, 1H), 8.13 (br s, 1H), 7.80 (s, 1H), 7.76-7.75 (m, 2H), 7.61-7.51 (m, 5H), 7.23-7.21 (m, 2H), 5.44 (s, 2H), 4.03 (s, 2H), 3.21 (t, J=7.6 Hz, 1H), 1.68 (t, J=7.2 Hz, 2H), 1.47 (sep, J=6.6 Hz, 1H), 0.88 (d, J=6.5 Hz, 3H), 0.87 (d, J=6.5 Hz, 3H). $^{13}C$ NMR (126 MHz, DMSO-$d_6$) δ ppm: 167.9, 166.3, 143.6, 140.4, 138.7, 132.4, 130.7, 129.1 (2C), 128.7 (2C), 126.5 (2C), 123.1, 119.6 (2C), 52.4, 50.0, 38.1, 38.0, 25.7, 22.4, 22.3. HRMS-ESI+ (m/z): calcd. for $C_{23}H_{29}N_6O_5S$ $[M+H]^+$ 501.1920, found 501.1889.

N-[4-[[4-[(Cyclohexylsulfonylamino)methyl]triazol-1-yl]methyl]phenyl]-2-(hydroxycarbamoyl)-4-methyl-pentanamide (168)

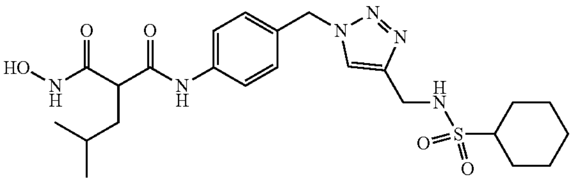 [SMILES: CC(C)CC(C(=O)NO)C(=O)Nc1ccc(Cn2cc(CNS(=O)(=O)C3CCCCC3)nn2)cc1]

Compound 168 was synthesized according to the general procedure D, using ester 158 (50 mg, 0.1 mmol), KCN (1.9 mg, 0.03 mmol) and $NH_2OH$ (1.2 mL, 50% w/w in water) in MeOH (1.2 mL) for 48 h. The crude product was purified by flash chromatography on silica gel ($CH_2Cl_2$ to $CH_2Cl_2$/MeOH: 9/1) affording compound 168 as a white solid after lyophilization (7 mg, 14%). Purity: 100%, LC tr=3.36 min, MS (ESI+): m/z=501 $[M+H]^+$. $^1H$ NMR (500 MHz, DMSO-$d_6$) δ ppm: 10.53 (br s, 1H), 9.83 (s, 1H), 8.96 (br s, 1H), 7.99 (s, 1H), 7.58-7.56 (m, 2H), 7.50 (t, J=5.8 Hz, 1H), 7.28-7.27 (m, 2H), 5.52 (s, 2H), 4.18 (d, J=5.8 Hz, 2H), 3.20 (t, J=7.6 Hz, 1H), 2.75-2.70 (m, 1H), 1.90-1.88 (m, 2H), 1.69-1.66 (m, 4H), 1.55-1.54 (m, 1H), 1.47 (sep, J=6.6 Hz, 1H), 1.27-1.20 (m, 2H), 1.07-1.03 (m, 3H), 0.87-0.86 (m, 6H). $^{13}C$ NMR (126 MHz, DMSO-$d_6$) δ ppm: 167.8, 166.2, 144.9, 138.7, 130.9, 128.6 (2C), 123.1, 119.5 (2C), 59.4, 52.4, 49.9, 38.0, 37.7, 25.9 (2C), 25.7, 24.8, 24.5 (2C), 22.4, 22.3. HRMS-ESI+ (m/z): calcd. for $C_{23}H_{35}N_6O_5S$ $[M+H]^+$ 507.2390, found 507.2356.

2-(Hydroxycarbamoyl)-N-[4-[[4-[(isobutylsulfonylamino)methyl]triazol-1-yl]methyl]phenyl]-4-methyl-pentanamide (169)

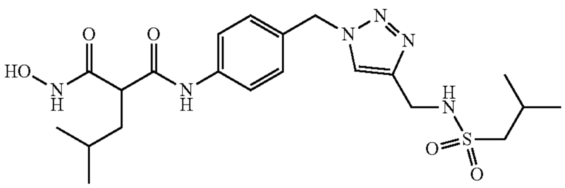 [SMILES: CC(C)CC(C(=O)NO)C(=O)Nc1ccc(Cn2cc(CNS(=O)(=O)CC(C)C)nn2)cc1]

Compound 169 was synthesized according to the general procedure D, using ester 159 (75 mg, 0.15 mmol), KCN (2.94 mg, 0.05 mmol) and $NH_2OH$ (1.5 mL, 50% w/w in water) in MeOH (1.5 mL) overnight. The crude product was purified by flash chromatography on silica gel ($CH_2Cl_2$ to $CH_2Cl_2$/MeOH: 95/5) affording compound 169 as a white solid after lyophilization (35 mg, 48%). Purity: 100%, LC tr=3.33 min, MS (ESI+): m/z=481 $[M+H]^+$. $^1H$ NMR (500 MHz, DMSO-$d_6$) δ ppm: 10.52 (s, 1H), 9.80 (s, 1H), 8.97 (s, 1H), 8.00 (s, 1H), 7.57-7.55 (m, 2H), 7.53 (t, J=6.0 Hz, 1H), 7.28-7.26 (m, 2H), 5.52 (s, 2H), 4.18 (d, J=6.0 Hz, 2H), 3.20 (t, J=7.6 Hz, 1H), 2.82 (d, J=6.4 Hz, 2H), 1.97 (sep, J=6.7 Hz, 1H), 1.68-1.66 (m, 2H), 1.47 (sep, J=6.7 Hz, 1H), 0.92 (d, J=6.6 Hz, 6H), 0.87 (d, J=6.6 Hz, 3H), 0.86 (d, J=6.6 Hz, 3H). $^{13}C$ NMR (126 MHz, DMSO-$d_6$) δ ppm: 167.9, 166.3, 144.6, 138.7, 130.9, 128.6 (2C), 123.2, 119.5 (2C), 59.2, 52.4, 50.0, 38.0, 37.6, 25.7, 24.2, 22.4, 22.3, 22.2 (2C). HRMS-ESI+ (m/z): calcd. for $C_{21}H_{33}N_6O_5S$ $[M+H]^+$ 481.2233, found 481.2202.

2-Benzyl-3-(hydroxyamino)-N-[4-[[4-[[(4-iodophenyl)sulfonylamino]methyl]triazol-1-yl]methyl]phenyl]-3-oxo-propanamide (179)

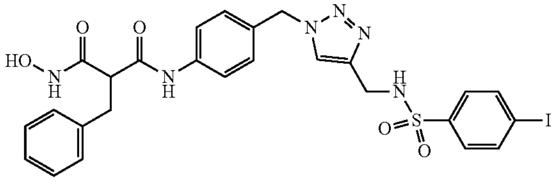 [SMILES: O=C(NO)C(Cc1ccccc1)C(=O)Nc1ccc(Cn2cc(CNS(=O)(=O)c3ccc(I)cc3)nn2)cc1]

Compound 179 was synthesized according to the general procedure D, using ester 177 (85 mg, 0.13 mmol), KCN (2.44 mg, 0.04 mmol) and $NH_2OH$ (1.8 mL, 50% w/w in water) in MeOH (1.8 mL) for 96 h. The crude product was purified by flash chromatography on silica gel ($CH_2Cl_2$ to $CH_2Cl_2$/MeOH: 9/1) affording compound 179 as a white solid after lyophilization (67 mg, 81%). Purity: 100%, LC tr=3.85 min, MS (ESI+): m/z=661 $[M+H]^+$. $^1H$ NMR (500 MHz, DMSO-$d_6$) δ ppm: 10.50 (br s, 1H), 9.86 (s, 1H), 8.97 (br s, 1H), 8.17 (br s, 1H), 7.93-7.91 (m, 2H), 7.83 (s, 1H), 7.55-7.50 (m, 4H), 7.27-7.23 (m, 6H), 7.18-7.15 (m, 1H), 5.44 (s, 2H), 4.03 (s, 2H), 3.46 (t, J=7.5 Hz, 1H), 3.16-3.06 (m, 2H). $^{13}C$ NMR (126 MHz, DMSO-$d_6$) δ ppm: 167.0, 165.4, 143.4, 140.0, 138.9, 138.7, 138.0 (2C), 130.7, 128.8 (2C), 128.7 (2C), 128.3 (2C), 128.2 (2C), 126.3, 123.2, 119.5 (2C), 100.4, 53.1, 52.4, 38.0, 34.4. HRMS-ESI+(m/z): calcd. for $C_{26}H_{26}IN_6O_5S$ $[M+H]^+$ 661.0730, found 661.0683.

2-(Hydroxycarbamoyl)-N-[4-[[4-[[(4-iodophenyl)sulfonylamino]methyl]triazol-1-yl]methyl]phenyl]-3-methyl-butanamide (182)

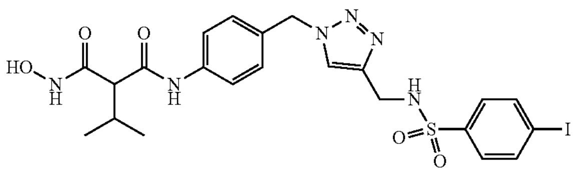 [SMILES: CC(C)C(C(=O)NO)C(=O)Nc1ccc(Cn2cc(CNS(=O)(=O)c3ccc(I)cc3)nn2)cc1]

Compound 182 was synthesized according to the general procedure E, using azide 180 (35 mg, 0.12 mmol), alkyne 93 (38.6 mg, 0.12 mmol), copper (II) sulfate pentahydrate (6.0 mg, 0.02 mmol) and sodium ascorbate (11.9 mg, 0.06 mmol) in DMF (2.5 mL) and $H_2O$ (1.5 mL) overnight. The crude product was purified by flash chromatography on silica gel ($CH_2Cl_2$ to $CH_2Cl_2$/MeOH: 95/5) affording compound 182 as a white solid after lyophilization (41 mg, 55%). Purity: 100%, LC tr=3.51 min, MS (ESI+): m/z=613 $[M+H]^+$. $^1H$ NMR (500 MHz, DMSO-$d_6$) δ ppm: 10.56 (s, 1H), 9.77 (s, 1H), 9.02 (s, 1H), 8.19 (t, J=5.8 Hz, 1H), 7.93-7.91 (m, 2H), 7.84 (s, 1H), 7.59-7.57 (m, 2H), 7.51-7.49 (m, 2H), 7.25-7.23 (m, 2H), 5.44 (s, 2H), 4.03 (d, J=5.7 Hz, 2H), 2.71 (d, J=10.5 Hz, 1H), 2.39-2.32 (m, 1H), 0.89-0.87 (m, 6H). HRMS-ESI+(m/z): calcd. for $C_{22}H_{26}IN_6O_5S$ $[M+H]^+$ 613.0730, found 613.0689.

2-(Cyclopropylmethyl)-3-(hydroxyamino)-N-[4-[[4-[[(4-iodophenyl) sulfonylamino]methyl]triazol-1-yl]methyl]phenyl]-3-oxo-propanamide (183)

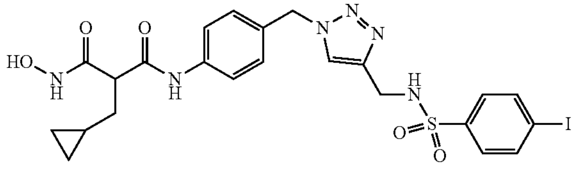 [SMILES: O=C(NO)C(CC1CC1)C(=O)Nc1ccc(Cn2cc(CNS(=O)(=O)c3ccc(I)cc3)nn2)cc1]

Compound 183 was synthesized according to the general procedure E, using azide 181 (50 mg, 0.17 mmol), alkyne 93 (52.9 mg, 0.12 mmol), copper (II) sulfate pentahydrate (8.2 mg, 0.03 mmol) and sodium ascorbate (16.3 mg, 0.08 mmol) in DMF (3 mL) and $H_2O$ (2 mL) overnight. The crude product was purified by flash chromatography on silica gel ($CH_2Cl_2$ to $CH_2Cl_2$/MeOH: 95/5) affording compound 183 as a white solid after lyophilization (49 mg, 47%). Purity: 100%, LC tr=3.64 min, MS (ESI+): m/z=625 $[M+H]^+$. $^1H$ NMR (500 MHz, DMSO-$d_6$) δ ppm: 10.51 (s, 1H), 9.85 (s, 1H), 8.96 (s, 1H), 8.20-8.17 (m, 1H), 7.93-7.91 (m, 2H), 7.84 (s, 1H), 7.58-7.50 (m, 4H), 7.25-7.23 (m, 2H), 5.44 (s, 2H), 4.03-4.02 (m, 2H), 3.21 (t, J=6.9 Hz, 1H), 1.69 (t, J=6.7 Hz, 2H), 0.65-0.62 (m, 1H), 0.37-0.35 (m, 2H), 0.08-0.07 (m, 2H). $^{13}C$ NMR (126 MHz, DMSO-$d_6$) δ ppm: 167.8, 166.2, 143.4, 140.0, 138.8, 138.0 (2C), 130.7, 128.7 (2C), 128.3 (2C), 123.2, 119.5 (2C), 100.4, 52.4, 52.0, 38.0, 34.1, 9.0, 4.3, 4.3. HRMS-ESI+ (m/z): calcd. for $C_{23}H_{26}IN_6O_5S$ $[M+H]^+$ 625.0730, found 625.0691.

2-(Hydroxycarbamoyl)-4-methyl-N-[4-[[4-[(1,1,3-trioxo-1,2-benzothiazol-2-yl)methyl]triazol-1-yl]methyl]phenyl]pentanamide (139)

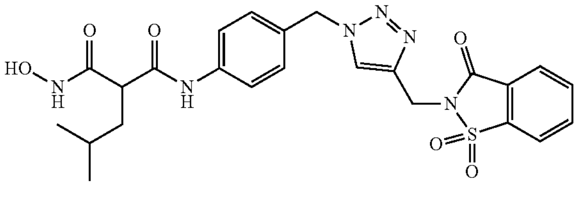 [SMILES: CC(C)CC(C(=O)NO)C(=O)Nc1ccc(Cn2cc(CN3C(=O)c4ccccc4S3(=O)=O)nn2)cc1]

Compound 139 was synthesized according to the general procedure E, using azide Z9 (50 mg, 0.26 mmol), alkyne 117 (145 mg, 0.66 mmol), copper (II) sulfate pentahydrate (8.2 mg, 0.03 mmol) and sodium ascorbate (51.9 mg, 0.26 mmol) in DMF (5.5 mL) and $H_2O$ (4.5 mL) for 72 h. The crude product was purified by preparative HPLC ($H_2O$+0.05% FA/ACN+0.05% FA 95:5 to 5:95) affording compound 139 as a white solid after lyophilization (21 mg, 15%). Purity: 100%, LC tr=2.55 min, MS (ESI+): m/z=527 $[M+H]^+$. $^1H$ NMR (500 MHz, DMSO-$d_6$) δ ppm: 10.53 (s, 1H), 9.81 (s, 1H), 8.96 (s, 1H), 8.32-8.30 (m, 1H), 8.14-8.12 (m, 2H), 8.07-7.99 (m, 2H), 7.56-7.54 (m, 2H), 7.25-7.24 (m, 2H), 5.51 (s, 2H), 4.97 (s, 2H), 3.20 (t, J=7.6 Hz, 1H), 1.67 (t, J=7.2 Hz, 2H), 1.46 (sep, J=6.6 Hz, 1H), 0.87 (d, J=6.6 Hz, 3H), 0.86 (d, J=6.6 Hz, 3H). $^{13}C$ NMR (126 MHz, DMSO-$d_6$) δ ppm: 167.8, 166.3, 158.3, 141.4, 138.7, 136.9, 136.0, 135.3, 130.8, 128.6 (2C), 126.2, 125.2, 124.0, 121.6, 119.5 (2C), 52.5, 49.9, 38.0, 33.5, 25.7, 22.4, 22.3. HRMS-ESI+ (m/z): calcd. for $C_{24}H_{27}N_6O_6S$ $[M+H]^+$ 527.1712, found 527.1619.

Ethyl 2-[[4-[[5-[(tert-butoxycarbonylamino)methyl] triazol-1-yl]methyl]phenyl]carbamoyl]-4-methyl-pentanoate (184)

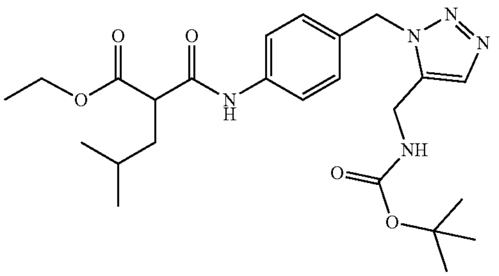 [SMILES: CCOC(=O)C(CC(C)C)C(=O)Nc1ccc(Cn2nncc2CNC(=O)OC(C)(C)C)cc1]

To a microwave tube filled with dioxane (6.0 mL) and degassed with $N_2$ during 10 min was added Cp*RuCl(COD) (16.7 mg, 0.04 mmol, 0.05 eq) and the mixture was stirred under $N_2$ at room temperature during 2 min. Then, 83 (280 mg, 0.88 mmol) and N-Boc-propargylamine (136 mg, 0.88 mmol) were added, the tube was sealed, and the reaction medium was heated at 80° C. and stirred overnight. After, dioxane was evaporated under reduced pressure, and the crude was purified through flash chromatography on silica gel column ($CH_2Cl_2$ to $CH_2Cl_2$/MeOH: 95/5) affording compound 184 as brown oil (295 mg, 70%). LC tr=4.40 min, MS (ESI+): m/z=947 $[2M+H]^+$, 474 $[M+H]^+$, 418 $[M\text{-}tBu+H]^+$, 374 $[M\text{-}Boc+H]^+$. $^1H$ NMR (500 MHz, DMSO-$d_6$) δ ppm: 10.28 (s, 1H), 7.58-7.56 (m, 2H), 7.53 (s, 1H), 7.46 (t, J=5.5 Hz, 1H), 7.17-7.16 (m, 2H), 5.54 (s, 2H), 4.18 (d, J=5.7 Hz, 2H), 4.13-4.06 (m, 2H), 3.56 (dd, J=8.7 and 6.1 Hz, 1H), 1.78-1.72 (m, 1H), 1.68-1.62 (m, 1H), 1.53-1.44 (m, 1H), 1.36 (s, 9H), 1.16 (t, J=7.1 Hz, 3H), 0.89 (d, J=6.7 Hz, 3H), 0.87 (d, J=6.7 Hz, 3H). $^{13}C$ NMR (126 MHz, DMSO-$d_6$) δ ppm: 169.7, 167.1, 155.5, 138.5, 135.7, 132.7, 130.7, 128.0 (2C), 119.4 (2C), 78.4, 60.6, 50.9, 50.2, 37.4, 32.9, 28.1 (3C), 25.6, 22.7, 21.9, 14.0.

tert-butyl N-[[3-[[4-[[2-(hydroxycarbamoyl)-4-methyl-pentanoyl]amino]phenyl]methyl]triazol-4-yl] methyl]carbamate (185)

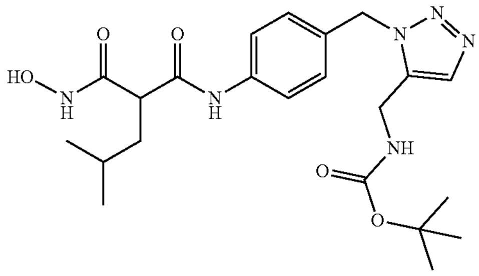 [SMILES: CC(C)CC(C(=O)NO)C(=O)Nc1ccc(Cn2nncc2CNC(=O)OC(C)(C)C)cc1]

To a solution of ethyl 2-[[4-[[5-[(tert-butoxycarbonylamino)methyl]triazol-1-yl]methyl]phenyl]carbamoyl]-4-methyl-pentanoate (70 mg, 0.15 mmol) in methanol (1.5 mL) was added aqueous hydroxylamine (1.5 mL, 50% w/w in water) and KCN (2.86 mg, 0.04 mmol, 0.3 eq.). The mixture was stirred 48 h. Then, the solvents were removed under reduced pressure and the residue was purified through preparative HPLC ($H_2O$+0.05% FA/ACN+0.05% FA: 95:5 to 5:95) to give the expected product as a white solid after lyophilization (18 mg, 26%). Purity: 100%, LC tr=3.46 min, MS (ESI+): m/z=921 $[2M+H]^+$, 461 $[M+H]^+$, 405 $[M\text{-}tBu+H]^+$, 361 $[M\text{-}Boc+H]^+$. $^1H$ NMR (500 MHz, DMSO-$d_6$) δ: 10.53 (s, 1H), 9.82 (s, 1H), 8.96 (s, 1H), 7.57-7.55 (m, 2H), 7.51 (s, 1H), 7.46 (t, J=5.3 Hz, 1H), 7.16-7.14 (m, 2H), 5.53 (s, 2H), 4.16 (d, J=5.7 Hz, 2H), 3.20 (t, J=7.6 Hz, 1H), 1.69-1.65 (m, 2H), 1.47 (sep, J=6.7 Hz, 1H), 1.36 (s, 9H), 0.87 (d, J=6.5 Hz, 3H), 0.86 (d, J=6.5 Hz, 3H). $^{13}C$ NMR (126 MHz, DMSO-$d_6$) δ: 167.8, 166.2, 155.5, 138.5, 135.7, 132.7, 130.5, 128.0 (2C), 119.5 (2C), 78.4, 50.2, 49.9, 38.0, 32.9, 28.1 (3C), 25.7, 22.4, 22.3. HRMS-ESI+ (m/z): calcd. for $C_{22}H_{33}N_6O_5$ $[M+H]^+$ 461.2512, found 461.2480.

[3-[[4-[(2-Ethoxycarbonyl-4-methyl-pentanoyl) amino]phenyl]methyl]triazol-4-yl]methylammonium;chloride (186)

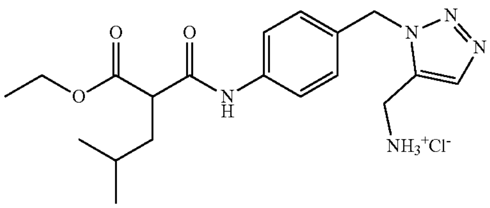

Compound 184 (290 mg, 0.61 mmol) was dissolved in ethanol and dichloromethane (5 mL, 2.5:2.5 v/v) and 4 N HCl in dioxane (2.5 mL) was added. The mixture was stirred overnight at room temperature. Then, solvents were evaporated to give compound 186 as a yellowish oil (251 mg, yield considered quantitative). LC tr=3.04 min, MS (ESI+): m/z=374 $[M+H]^+$. $^1H$ NMR (500 MHz, DMSO-$d_6$) δ: 10.47 (s, 1H), 8.74 (br s, 3H), 7.89 (s, 1H), 7.61-7.59 (m, 2H), 7.21-7.19 (m, 2H), 5.68 (s, 2H), 4.15-4.05 (m, 4H), 1.76-1.71 (m, 1H), 1.67-1.61 (m, 1H), 1.48 (sep, J=6.7 Hz, 1H), 1.15 (t, J=7.1 Hz, 3H), 0.88 (d, J=6.6 Hz, 3H), 0.86 (d, J=6.6 Hz, 3H). $^{13}C$ NMR (126 MHz, DMSO-$d_6$) δ: 169.8, 167.3, 138.8, 134.3, 131.1, 130.3, 128.2 (2C), 119.5 (2C), 60.6, 50.9, 50.6, 37.4, 31.1, 25.7, 22.7, 22.0, 14.0.

Ethyl 2-[[4-[[5-[[(4-iodophenyl)sulfonylamino] methyl]triazol-1-yl]methyl]phenyl]carbamoyl]-4-methyl-pentanoate (187)

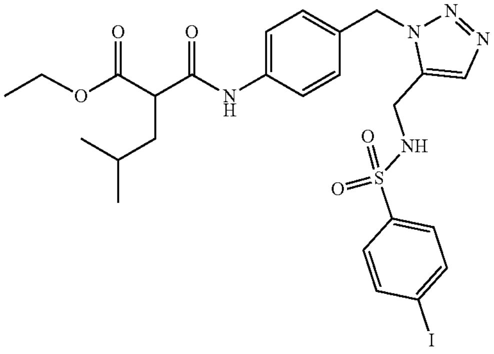 [SMILES: CCOC(=O)C(CC(C)C)C(=O)Nc1ccc(Cn2nncc2CNS(=O)(=O)c2ccc(I)cc2)cc1]

Compound 187 was synthesized according to the general procedure C, using 186 (70 mg, 0.17 mmol), 4-iodobenzenesulfonyl chloride (62 mg, 0.21 mmol) and N,N-diisopropylethylamine (89 μL, 0.51 mmol) in DMF (2 mL) overnight. The crude product was purified by flash chromatography on silica gel ($CH_2Cl_2$ to $CH_2Cl_2$/MeOH: 95/5) affording compound 187 as brown oil (71 mg, 64%). LC tr=4.68 min, MS (ESI+): m/z=640 $[M+H]^+$. $^1H$ NMR (500 MHz, DMSO-$d_6$) δ ppm: 10.30 (s, 1H), 8.39 (t, J=5.5 Hz, 1H), 7.96-7.94 (m, 2H), 7.57-7.55 (m, 2H), 7.50 (s, 1H), 7.48-7.46 (m, 2H), 7.13-7.11 (m, 2H), 5.48 (s, 2H), 4.14-4.04 (m, 4H), 3.56 (dd, J=8.7 and 6.2 Hz, 1H), 1.78-1.73 (m, 1H), 1.68-1.62 (m, 1H), 1.49 (sep, J=6.7 Hz, 1H), 1.15 (t, J=7.1 Hz, 3H), 0.89 (d, J=6.7 Hz, 3H), 0.87 (d, J=6.7 Hz, 3H). $^{13}C$ NMR (DMSO-$d_6$) δ ppm: 169.7, 167.1, 139.4, 138.6, 138.2 (2C), 133.5, 133.4, 130.3, 128.2 (2C), 128.2 (2C), 119.4 (2C), 100.9, 60.7, 50.9, 50.3, 37.4, 35.3, 25.6, 22.7, 21.9, 14.0.

Ethyl 2-[[4-[[5-[[(4-fluorophenyl)sulfonylamino] methyl]triazol-1-yl]methyl]phenyl]carbamoyl]-4-methyl-pentanoate (188)

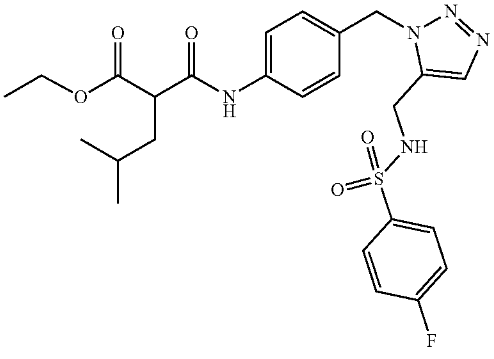

Compound 188 was synthesized according to the general procedure C, using 186 (70 mg, 0.17 mmol), 4-fluorobenzenesulfonyl chloride (39.9 mg, 0.21 mmol) and N,N-diisopropylethylamine (89 μL, 0.51 mmol) in DMF (2 mL) overnight. The crude product was purified by flash chromatography on silica gel ($CH_2Cl_2$ to $CH_2Cl_2$/MeOH: 95/5) affording compound 188 as pale yellow oil (65 mg, 70%). LC tr=4.41 min, MS (ESI+): m/z=532 $[M+H]^+$. $^1H$ NMR (500 MHz, DMSO-$d_6$) δ ppm: 10.29 (s, 1H), 8.35 (s, 1H), 7.78-7.75 (m, 2H), 7.56-7.55 (m, 2H), 7.49 (s, 1H), 7.41-7.38 (m, 2H), 7.13-7.12 (m, 2H), 5.48 (s, 2H), 4.12-4.06 (m, 4H), 3.56 (dd, J=8.7 and 6.2 Hz, 1H), 1.78-1.72 (m, 1H), 1.68-1.62 (m, 1H), 1.49 (sep, J=6.7 Hz, 1H), 1.15 (t, J=7.1 Hz, 3H), 0.89 (d, J=6.7 Hz, 3H), 0.87 (d, J=6.7 Hz, 3H). $^{13}C$ NMR (126 MHz, DMSO-$d_6$) δ ppm: 169.7, 167.2, 164.2 (J=251.4 Hz), 138.6, 136.2 (J=2.8 Hz), 133.5, 133.2, 130.3, 129.6 (J=9.2 Hz, 2C), 128.2 (2C), 119.4 (2C), 116.4 (J=23.0 Hz, 2C), 60.7, 50.9, 50.3, 37.4, 35.3, 25.6, 22.6, 21.9, 14.0.

Ethyl 2-[[4-[[5-[(isobutylsulfonylamino)methyl] triazol-1-yl]methyl]phenyl]carbamoyl]-4-methyl-pentanoate (189)

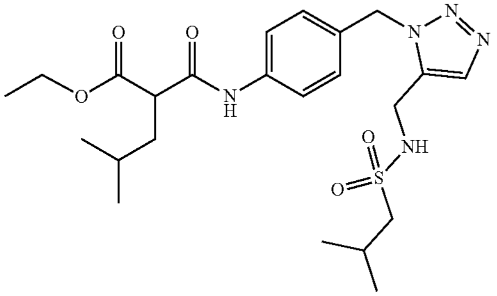 [SMILES: CCOC(=O)C(CC(C)C)C(=O)Nc1ccc(Cn2nncc2CNS(=O)(=O)CC(C)C)cc1]

Compound 189 was synthesized according to the general procedure C, using 186 (100 mg, 0.24 mmol), 4-fluorobenzenesulfonyl chloride (45.9 mg, 0.29 mmol) and N,N-diisopropylethylamine (127 μL, 0.73 mmol) in DMF (2 mL) overnight. The crude product was purified by flash chromatography on silica gel ($CH_2Cl_2$ to $CH_2Cl_2$/MeOH: 95/5) affording compound 189 as yellow oil (80 mg, 65%). LC tr=4.30 min, MS (ESI+): m/z=494 $[M+H]^+$. $^1H$ NMR (500 MHz, DMSO-$d_6$) δ ppm: 10.29 (s, 1H), 7.72 (t, J=5.2 Hz, 1H), 7.67 (s, 1H), 7.58-7.56 (m, 2H), 7.21-7.19 (m, 2H), 5.56 (s, 2H), 4.22 (d, J=5.2 Hz, 2H), 4.14-4.04 (m, 2H), 3.55 (dd, J=8.8 and 6.2 Hz, 1H), 2.82 (d, J=6.5 Hz, 2H), 2.01 (sep, J=6.7 Hz, 1H), 1.77-1.71 (m, 1H), 1.67-1.61 (m, 1H), 1.48 (sep, J=6.7 Hz, 1H), 1.15 (t, J=7.1 Hz, 3H), 0.96 (d, J=6.7 Hz, 6H), 0.88 (d, J=6.7 Hz, 3H), 0.87 (d, J=6.7 Hz, 3H). $^{13}C$ NMR (126 MHz, DMSO-$d_6$) δ ppm: 169.7, 167.1, 138.6, 134.4, 133.4, 130.5, 128.2 (2C), 119.4 (2C), 60.7, 58.9, 50.9, 50.3, 37.4, 34.9, 25.6, 24.2, 22.7, 22.2 (2C), 21.9, 14.0.

2-(Hydroxycarbamoyl)-N-[4-[[5-[[(4-iodophenyl)sulfonylamino]methyl]triazol-1-yl]methyl]phenyl]-4-methyl-pentanamide (190)

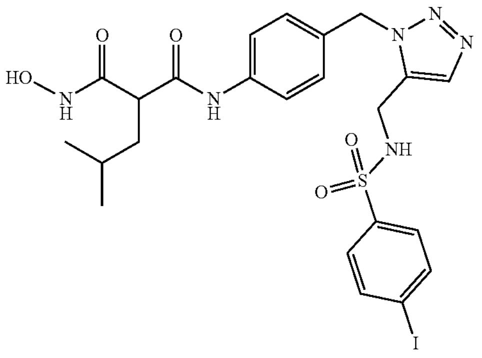

Compound 190 was synthesized according to the general procedure D, using ester 187 (64 mg, 0.1 mmol), KCN (1.94 mg, 0.03 mmol) and $NH_2OH$ (1.2 mL, 50% w/w in water) in MeOH (1.2 mL) for 48 h. The crude product was purified through preparative HPLC ($H_2O$+0.05% FA/ACN+0.05% FA: 95:5 to 5:95) to give compound 190 as a white solid after lyophilization (18 mg, 29%). Purity: 100%, LC tr=3.82 min, MS (ESI+): m/z=627 $[M+H]^+$. $^1H$ NMR (500 MHz, DMSO-$d_6$) δ ppm: 10.54 (br s, 1H), 9.82 (s, 1H), 8.97 (s, 1H), 8.39 (br s, 1H), 7.97-7.95 (m, 2H), 7.56-7.54 (m, 2H), 7.49-7.47 (m, 3H), 7.11-7.10 (m, 2H), 5.47 (s, 2H), 4.05 (s, 2H), 3.21 (t, J=7.6 Hz, 1H), 1.70-1.66 (m, 2H), 1.48 (sep, J=6.6 Hz, 1H), 0.87 (d, J=6.6 Hz, 3H), 0.86 (d, J=6.6 Hz, 3H). $^{13}C$ NMR (126 MHz, DMSO-$d_6$) δ ppm: 167.9, 166.3, 139.4, 138.6, 138.2 (2C), 133.5, 133.4, 130.2, 128.2 (2C), 128.1 (2C), 119.6 (2C), 100.9, 50.3, 50.0, 38.0, 35.3, 25.7, 22.4, 22.3. HRMS-ESI+ (m/z): calcd. for $C_{23}H_{28}IN_6O_5S$ $[M+H]^+$: 627.0887, found 627.0881.

N-[4-[[5-[[(4-Fluorophenyl)sulfonylamino]methyl]triazol-1-yl]methyl]phenyl]-2-(hydroxycarbamoyl)-4-methyl-pentanamide (191)

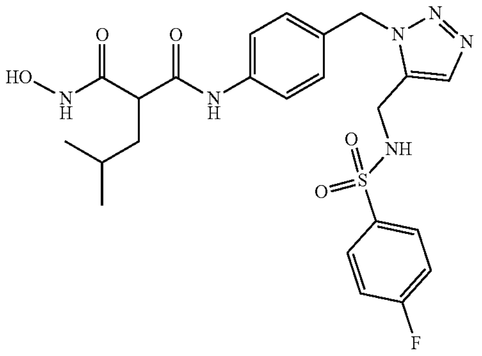 [SMILES: CC(C)CC(C(=O)NO)C(=O)Nc1ccc(Cn2nncc2CNS(=O)(=O)c2ccc(I)cc2)cc1]

Compound 191 was synthesized according to the general procedure D, using ester 188 (58 mg, 0.11 mmol), KCN (2.11 mg, 0.03 mmol) and $NH_2OH$ (1.2 mL, 50% w/w in water) in MeOH (1.2 mL) for 48 h. The crude product was purified through preparative HPLC ($H_2O$+0.05% FA/ACN+0.05% FA: 95:5 to 5:95) to give compound 191 as a white solid after lyophilization (21 mg, 37%). Purity: 100%, LC tr=3.50 min, MS (ESI+): m/z=519 $[M+H]^+$. $^1H$ NMR (500 MHz, DMSO-$d_6$) δ ppm: 10.53 (br s, 1H), 9.82 (s, 1H), 8.96 (s, 1H), 8.35 (br s, 1H), 7.79-7.76 (m, 2H), 7.56-7.54 (m, 2H), 7.48 (s, 1H), 7.42-7.39 (m, 2H), 7.12-7.10 (m, 2H), 5.48 (s, 2H), 4.06 (s, 2H), 3.21 (t, J=7.6 Hz, 1H), 1.70-1.66 (m, 2H), 1.47 (sep, J=6.7 Hz, 1H), 0.87 (d, J=6.7 Hz, 3H), 0.86 (d, J=6.7 Hz, 3H). $^{13}C$ NMR (126 MHz, DMSO-$d_6$) δ ppm: 167.9, 166.3, 164.2 (d, J=251.1 Hz), 138.6, 136.2 (d, J=2.7 Hz), 133.5, 133.3, 130.1, 129.6 (d, J=9.6 Hz, 2C), 128.1 (2C), 119.5 (2C), 116.4 (d, J=22.5 Hz, 2C), 50.3, 50.0, 38.0, 35.3, 25.7, 22.4, 22.3. HRMS-ESI+ (m/z): calcd. for $C_{23}H_{28}FN_6O_5S$ $[M+H]^+$ 519.1826, found 519.1821.

2-(Hydroxycarbamoyl)-N-[4-[[5-[(isobutylsulfonylamino)methyl]triazol-1-yl]methyl]phenyl]-4-methyl-pentanamide (192)

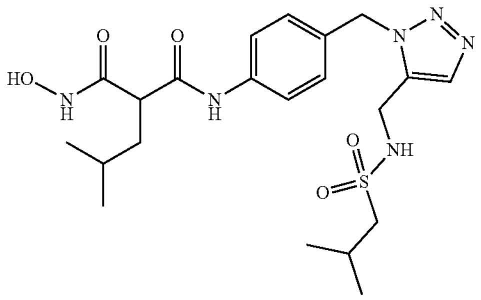 [SMILES: CC(C)CC(C(=O)NO)C(=O)Nc1ccc(Cn2nncc2CNS(=O)(=O)CC(C)C)cc1]

Compound 192 was synthesized according to the general procedure D, using ester 189 (70 mg, 0.14 mmol), KCN (2.74 mg, 0.04 mmol) and $NH_2OH$ (1.5 mL, 50% w/w in water) in MeOH (1.5 mL) for 48 h. The crude product was purified through preparative HPLC ($H_2O$+0.05% FA/ACN+0.05% FA: 95:5 to 5:95) to give compound 192 as a white solid after lyophilization (34 mg, 50%). Purity: 100%, LC tr=3.36 min, MS (ESI+): m/z=481 $[M+H]^+$. $^1H$ NMR (500 MHz, DMSO-$d_6$) δ ppm: 10.52 (s, 1H), 9.81 (s, 1H), 8.96 (s, 1H), 7.72 (t, J=5.4 Hz, 1H), 7.67 (s, 1H), 7.57-7.55 (m, 2H), 7.19-7.17 (m, 2H), 5.55 (s, 2H), 4.22 (d, J=5.1 Hz, 2H), 3.20 (t, J=7.6 Hz, 1H), 2.84 (d, J=6.4 Hz, 2H), 2.02 (sep, J=6.7 Hz, 1H), 1.69-1.65 (m, 2H), 1.47 (sep, J=6.7 Hz, 1H), 0.97 (d, J=6.7 Hz, 6H), 0.87 (d, J=6.7 Hz, 3H), 0.86 (d, J=6.7 Hz, 3H). $^{13}C$ NMR (126 MHz, DMSO-$d_6$) δ ppm: 167.8, 166.3, 138.6, 134.4, 133.4, 130.4, 128.1 (2C), 119.5 (2C), 58.9, 50.3, 50.0, 38.0, 35.0, 25.7, 24.2, 22.4, 22.3, 22.2 (2C). HRMS-ESI$^-$ (m/z): calcd. for $C_{21}H_{31}IN_6O_5S$ $[M-H]^-$ 479.2077, found 479.2083.

N-[4-[[4-(Aminomethyl)triazol-1-yl]methyl]phenyl]-2-(hydroxycarbamoyl)-4-methyl-pentanamide (140)

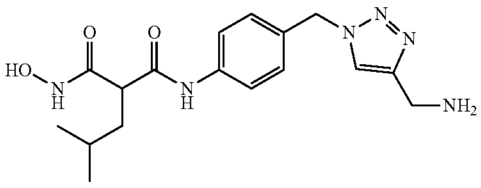 [SMILES: CC(C)CC(C(=O)NO)C(=O)Nc1ccc(Cn2cc(CN)nn2)cc1]

Compound 139 (30 mg, 0.07 mmol) was dissolved in $CH_2Cl_2$ (1 mL) and was cooled down to 0° C. with an ice-bath before an addition of 4N HCl in dioxane (1 mL). The mixture was stirred at room temperature overnight. Solvents were then evaporated under reduced pressure, and the crude product was purified through preparative HPLC ($H_2O$+0.05% FA/ACN+0.05% FA: 95:5 to 5:95) to give compound 140 as a beige solid after lyophilization (8 mg, 30%). Purity: 100%, LC tr=2.29 min, MS (ESI+): m/z=361 $[M+H]^+$. $^1H$ NMR (500 MHz, DMSO-$d_6$) δ ppm: 10.33 (s, 1H), 8.62 (m, 2H), 8.10 (s, 1H), 7.63-7.61 (m, 2H), 7.30-7.28 (m, 2H), 5.56 (s, 2H), 4.04 (s, 2H), 3.59-3.15 (m, 3H), 1.65 (t, J=7.2 Hz, 2H), 1.44 (sep, J=6.7 Hz, 1H), 0.86 (d, J=6.4 Hz, 3H), 0.85 (d, J=6.6 Hz, 3H). $^{13}C$ NMR (126 MHz, DMSO-$d_6$) δ ppm: 166.7, 166.1, 141.6, 139.0, 130.5, 128.7 (2C), 123.9, 119.4 (2C), 52.6, 49.3, 37.4, 34.3, 25.6, 22.5, 22.3. HRMS-ESI+ (m/z): calcd. for $C_{17}H_{25}N_6O_3$ $[M+H]^+$ 361.1988, found 361.1958.

tert-Butyl 4-[methoxy(methyl)carbamoyl]thiazolidine-3-carboxylate (96)

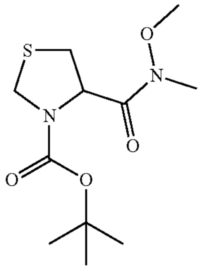 [SMILES: CON(C)C(=O)C1CSCN1C(=O)OC(C)(C)C]

To a solution of 3-tert-butoxycarbonylthiazolidine-4-carboxylic acid (1000 mg, 4.3 mmol) in DMF (8 mL) were added triethylamine (3520 μL, 25.6 mmol), HOBt (656 mg, 4.3 mmol) and EDC·HCl (2880 mg, 15.0 mmol) and the reaction media was stirred for 20 minutes. A suspension of N-methoxymethanamine;hydrochloride (836 mg, 8.6 mmol) and triethylamine (1170 μL, 8.6 mmol) in DMF (2 mL) was then added and the mixture was stirred at room temperature overnight. Triethylamine salts were filtered; the filtrate was dissolved in water and extracted with ethyl acetate. Combined organic layers were dried over $MgSO_4$, filtered and concentrated under reduced pressure. The residue was finally purified through flash chromatography on silica gel (cHex to cHex/EtOAc: 5/5) affording compound 96 as a white solid (903 mg, 80%). LC tr=3.53 min, MS (ESI+): m/z=221 $[M+H-tBu]^+$, 177 $[M+H-Boc]^+$. $^1H$ NMR (500 MHz, $CDCl_3$) δ ppm: 5.02-5.00 (m, 0.5H), 4.83-4.81 (m, 0.4H), 4.66-4.65 (m, 0.4H), 4.59-4.58 (m, 0.6 Hz), 4.45-4.44 (m, 0.4H), 4.44-4.42 (m, 0.6H), 3.71 (s, 1.6H), 3.66 (s, 1.4H), 3.36-3.26 (m, 1H), 3.13 (s, 3H), 2.99-2.93 (m, 1H), 1.38 (s, 4.9H), 1.34 (s, 4.1H). $^{13}C$ NMR (126 MHz, $CDCl_3$) δ ppm: 171.2 (min), 170.8 (maj), 153.2 (maj), 152.9 (min), 80.8 (min), 80.7 (maj), 61.3 (maj), 61.3 (min), 59.5 (min), 59.3 (maj), 49.9 (min), 49.4 (maj), 34.5 (min), 33.4 (maj), 32.4 (min), 32.2 (maj), 28.2 (maj), 28.2 (min).

tert-Butyl 4-formylthiazolidine-3-carboxylate (97)

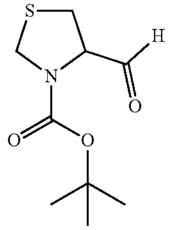

Compound 96 (903 mg, 3.27 mmol) was dissolved in anhydrous THE (30 mL) and cooled down to 0° C. before addition of a solution of LAH (2.4 M in THF, 1.7 mL, 4.08 mmol). The mixture was stirred for 30 minutes and then quenched carefully with 1M aq. $KHSO_4$ at 0° C. The resulting blurry solution was poured in 1M aq. HCl and extracted with $CH_2Cl_2$. Combined organic layers were dried over $MgSO_4$, filtered and concentrated under reduced pressure. The residue was filtered through a pad of silica gel ($CH_2Cl_2$), affording compound 97 as yellow oil (620 mg, 87%). LC tr=not visible, MS (ESI+): m/z=no ionization. $^1H$ NMR (500 MHz, $CDCl_3$) δ ppm: 9.59-9.56 (m, 1H), 4.67-4.57 (m, 2H), 4.45-4.42 (m, 1H), 3.25-3.13 (m, 2H), 1.51-1.46 (m, 9H). $^{13}C$ NMR (126 MHz, $CDCl_3$) δ ppm: 199.5 (maj), 199.4 (min), 153.9 (min), 153.3 (maj), 82.1 (maj), 81.8 (min), 67.3 (min), 67.2 (maj), 49.8 (maj), 48.9 (min), 32.3 (maj), 30.5 (min), 28.4 (min, 3C), 28.4 (maj).

tert-Butyl 4-ethynylthiazolidine-3-carboxylate (98)

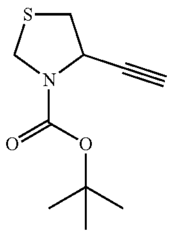

Compound 97 (610 mg, 2.1 mmol) and potassium carbonate (776 mg, 5.6 mmol, 2.0) were mixed in anhydrous methanol (8 mL) before an addition of Ohira-Bestmann reagent (809 μL, 3.4 mmol). The resulting mixture was stirred overnight at room temperature. The mixture was then diluted with $CH_2Cl_2$ and washed with 5% aq. $NaHCO_3$. The organic layer was concentrated under reduced pressure and the residue was purified through flash chromatography on silica gel column (cHex to cHex/EtOAc: 7/3) affording compound 98 as brown oil (445 mg, 74%). LC tr=4.42 min, MS (ESI+): m/z=158 $[M+H-tBu]^+$, 114 $[M+H-Boc]^+$. $^1H$ NMR (500 MHz, $CDCl_3$) δ ppm: 5.10-5.00 (m, 1H), 4.64 (d, J=9.4 Hz, 1H), 4.40 (d, J=9.4 Hz, 1H), 3.30-3.23 (m, 1H), 3.09-3.06 (m, 1H), 2.33 (d, J=2.1 Hz, 1H), 1.49 (s, 9H). $^{13}C$ NMR (126 MHz, $CDCl_3$) δ ppm: 153.0, 81.5, 77.4. 71.1, 55.9, 50.9, 47.8, 36.9, 28.4 (3C).

(4-Ethynylthiazolidin-3-yl)-(4-fluorophenyl)methanone (99)

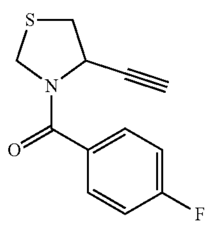 [SMILES: C#CC1CSCN1C(=O)c1ccc(F)cc1]

Compound 98 (335 mg, 1.6 mmol) was dissolved in methanol and dichloromethane (12.0 mL, 6:6 v/v), and the mixture was cooled down to 0° C. with an ice-bath before an addition of 4N HCl in dioxane (6 mL). The mixture was stirred at room temperature 1 h. The mixture was then cooled down to 0° C., and triethylamine (1290 μL, 9.4 mmol) and 4-fluorobenzoyl chloride (208 μL, 1.7 mmol) were carefully added. The mixture was stirred at room temperature overnight. It was then diluted in $CH_2Cl_2$ and washed with brine. Combined organic layers were concentrated under reduced pressure and the residue was purified through flash chromatography on silica gel column (cHex to cHex/EtOAc: 7/3) affording compound 99 as a brown solid (256 mg, 69%). LC tr=3.76 min, MS (ESI+): m/z=236 $[M+H]^+$. $^1H$ NMR (500 MHz, $CDCl_3$) δ ppm: 7.64-7.62 (m, 2H), 7.14-7.11 (m, 2H), 5.32 (br s, 2H), 4.60 (br s, 1H), 3.26-3.14 (m, 2H), 2.43 (s, 1H). $^{13}C$ NMR (126 MHz, $CDCl_3$) δ ppm: 168.5, 164.3 (d, J=251.8 Hz), 131.3 (d, J=11.0 Hz), 130.2 (d, J=7.6 Hz, 2C), 115.8 (d, J=21.8 Hz, 2C), 81.1, 77.4, 72.5, 50.3, 37.0.

tert-butyl N-[4-(prop-2-ynylsulfamoyl)phenyl]carbamate (193)

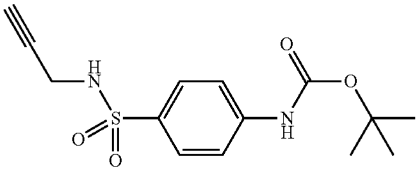 [SMILES: C#CCNS(=O)(=O)c1ccc(NC(=O)OC(C)(C)C)cc1]

Compound 193 was synthesized according to the general procedure C, using propargylamine (72.4 μL, 1.13 mmol), tert-butyl N-(4-chlorosulfonylphenyl)carbamate (300 mg, 1.03 mmol) and N,N-diisopropylethylamine (359 μL, 2.06 mmol) in $CH_2Cl_2$ (5 mL) overnight. The crude product was purified by flash chromatography on silica gel ($CH_2Cl_2$ to $CH_2Cl_2$/MeOH: 98/2) affording compound 193 as a brown solid (237 mg, 74%). MS (ESI+): m/z=311 $[M+H]^+$. $^1H$ NMR (500 MHz, DMSO-$d_6$) δ ppm: 9.81 (s, 1H), 7.94 (t, J=5.4 Hz, 1H), 7.69-7.67 (m, 2H), 7.62-7.61 (m, 2H), 3.64-3.63 (m, 2H), 3.06 (t, J=2.4 Hz, 1H), 1.48 (s, 9H). $^{13}C$ NMR (126 MHz, DMSO-$d_6$) δ ppm: 152.5, 143.3, 133.0, 127.9 (2C), 117.4 (2C), 79.8, 79.5, 74.6, 31.9, 28.0 (3C).

4-acetyl-N-prop-2-ynyl-benzenesulfonamide (194)

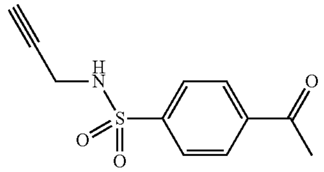 [SMILES: C#CCNS(=O)(=O)c1ccc(C(C)=O)cc1]

Compound 194 was synthesized according to the general procedure C, using propargylamine (72.4 μL, 1.13 mmol), 4-acetylbenzenesulfonyl chloride (300 mg, 1.03 mmol) and N,N-diisopropylethylamine (359 μL, 2.06 mmol) in $CH_2Cl_2$ (5 mL) overnight. The crude product was purified by flash chromatography on silica gel ($CH_2Cl_2$ to $CH_2Cl_2$/MeOH: 98/2) affording compound 194 as a brown solid (237 mg, 74%). $^1H$ NMR (500 MHz, DMSO-$d_6$) δ ppm: 8.34 (br s, 1H), 8.13-7.94 (m, 4H), 3.75 (br s, 2H), 3.04 (br s, 1H), 2.64 (s, 3H). $^{13}C$ NMR (126 MHz, DMSO-$d_6$) δ ppm: 197.4, 144.3, 139.5, 128.9 (2C), 127.1 (2C), 79.1, 74.9, 31.9, 27.1.

4-(2-methoxyethoxy)-N-prop-2-ynyl-benzenesulfonamide (195)

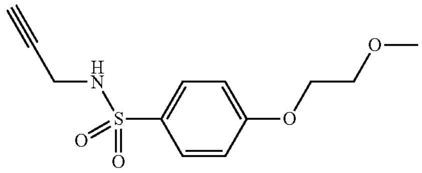 [SMILES: C#CCNS(=O)(=O)c1ccc(OCCOC)cc1]

Compound 195 was synthesized according to the general procedure C, using propargylamine (42.2 μL, 0.7 mmol), 4-(2-methoxyethoxy)benzenesulfonyl chloride (150 mg, 0.6 mmol) and N,N-diisopropylethylamine (209 μL, 1.2 mmol) in $CH_2Cl_2$ (5 mL) overnight. The crude product was purified by flash chromatography on silica gel ($CH_2Cl_2$ to $CH_2Cl_2$/MeOH: 95/5) affording compound 195 as a colorless oil (97 mg, 60%). MS (ESI+): m/z=270 $[M+H]^+$. $^1H$ NMR (500 MHz, DMSO-$d_6$) δ ppm: 7.95 (s, 1H), 7.72-7.71 (m, 2H), 7.11-7.10 (m, 2H), 4.18-4.16 (m, 2H), 3.68-3.66 (m, 2H), 3.64 (d, J=2.5 Hz, 2H), 3.31 (s, 3H), 3.04 (t, J=2.5 Hz, 1H). $^{13}C$ NMR (126 MHz, DMSO-$d_6$) δ ppm: 161.5, 132.1, 128.9 (2C), 114.6 (2C), 79.4, 74.6, 70.1, 67.4, 58.2, 31.9.

methyl 4-(prop-2-ynylsulfamoyl)benzoate (196)

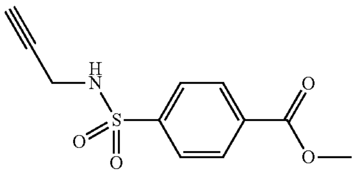 [SMILES: C#CCNS(=O)(=O)c1ccc(C(=O)OC)cc1]

Compound 196 was synthesized according to the general procedure C, using propargylamine (150 μL, 2.34 mmol), methyl 4-chlorosulfonylbenzoate (500 mg, 2.13 mmol) and N,N-diisopropylethylamine (742 μL, 4.26 mmol) in $CH_2Cl_2$ (10 mL) overnight. The crude product was purified by flash chromatography on silica gel (cHex to cHex/EtOAc: 5/5) affording compound 196 as a white solid (391 mg, 72%). MS (ESI+): m/z=254 $[M+H]^+$. $^1$H NMR (500 MHz, DMSO-$d_6$) δ ppm: 8.36 (t, J=5.8 Hz, 1H), 8.14-8.13 (m, 2H), 7.95-7.94 (m, 2H), 4.18-4.16 (m, 2H), 3.89 (s, 3H), 3.76-3.75 (m, 2H), 3.01 (br s, 1H). $^{13}$C NMR (126 MHz, DMSO-$d_6$) δ ppm: 165.2, 144.7, 132.9, 129.9 (2C), 127.2 (2C), 79.0, 74.9, 52.6, 31.9.

4-isopropoxy-N-prop-2-ynyl-benzenesulfonamide (197)

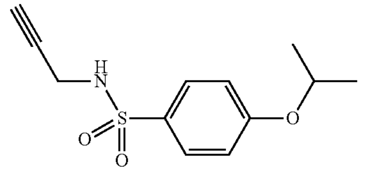 [SMILES: C#CCNS(=O)(=O)c1ccc(OC(C)C)cc1]

Compound 197 was synthesized according to the general procedure C, using propargylamine (90 μL, 1.41 mmol), 4-isopropoxybenzenesulfonyl chloride (300 mg, 1.28 mmol) and N,N-diisopropylethylamine (446 μL, 2.56 mmol) in $CH_2Cl_2$ (5 mL) overnight. The crude product was purified by flash chromatography on silica gel (cHex to cHex/EtOAc: 6/4) affording compound 197 as a pale yellow powder (152 mg, 47%). MS (ESI+): m/z=254 $[M+H]^+$. $^1$H NMR (500 MHz, DMSO-$d_6$) δ ppm: 7.93 (t, J=5.8 Hz, 1H), 7.72-7.67 (m, 2H), 7.09-7.04 (m, 2H), 4.72 (sept, J=6.0 Hz, 1H), 3.66-3.61 (m, 2H), 3.06-3.03 (t, J=2.3 Hz, 1H), 1.28 (d, J=6.0 Hz, 6H). $^{13}$C NMR (126 MHz, DMSO-$d_6$) δ ppm: 160.6, 131.5, 128.9 (2C), 115.4 (2C), 79.5, 74.6, 69.8, 31.9, 21.6 (2C).

4-isopropyl-N-prop-2-ynyl-benzenesulfonamide (198)

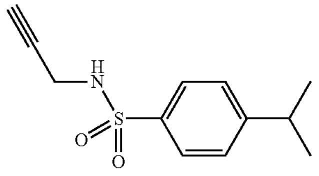 [SMILES: C#CCNS(=O)(=O)c1ccc(C(C)C)cc1]

Compound 198 was synthesized according to the general procedure C, using propargylamine (195 μL, 3.02 mmol), 4-isopropylbenzenesulfonyl chloride (600 mg, 2.74 mmol) and N,N-diisopropylethylamine (955 μL, 5.48 mmol) in $CH_2Cl_2$ (10 mL) overnight. The crude product was purified by flash chromatography on silica gel (cHex to cHex/EtOAc: 6/4) affording compound 198 as a pale yellow powder (112 mg, 17%). MS (ESI+): m/z=238 $[M+H]^+$. $^1$H NMR (500 MHz, DMSO-$d_6$) δ ppm: 7.95 (br s, 1H), 7.74-7.70 (m, 2H), 7.47-7.43 (m, 2H), 3.68-3.64 (m, 2H), 3.05-3.01 (m, 1H), 3.01-2.94 (m, 1H), 1.22 (d, J=6.9 Hz, 6H). $^{13}$C NMR (126 MHz, DMSO-$d_6$) δ ppm: 153.8, 138.3, 127.4 (2C), 127.3 (2C), 79.9, 75.0, 33.9, 32.4, 24.0 (2C).

ethyl 2-[[4-[[4-[[[4-(2-methoxyethoxy)phenyl]sulfonylamino]methyl]triazol-1-yl]methyl]phenyl]carbamoyl]-4-methyl-pentanoate (199)

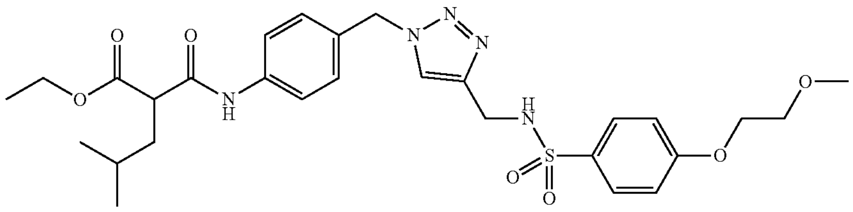 [SMILES: CCOC(=O)C(CC(C)C)C(=O)Nc1ccc(Cn2cc(CNS(=O)(=O)c3ccc(OCCOC)cc3)nn2)cc1]

Compound 199 was synthesized according to the general procedure E, using azide 83 (100 mg, 0.31 mmol), alkyne 195 (83.5 mg, 0.31 mmol), copper (II) sulfate pentahydrate (15.7 mg, 0.06 mmol) and sodium ascorbate (31.1 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 95/5) affording compound 199 as a white solid (152 mg, 83%). MS (ESI+): m/z=588 $[M+H]^+$. $^1$H NMR (500 MHz, DMSO-$d_6$) δ ppm: 10.29 (s, 1H), 7.92 (t, J=5.8 Hz, 1H), 7.85 (s, 1H), 7.70-7.69 (m, 2H), 7.58-7.56 (m, 2H), 7.25-7.24 (m, 2H), 7.07-7.05 (m, 2H), 5.46 (s, 2H), 4.18-4.16 (m, 2H), 4.13-4.05 (m, 2H), 3.98 (d, J=5.9 Hz, 2H), 3.68-3.66 (m, 2H), 3.31 (s, 3H), 3.56 (dd, J=8.9 and 6.5 Hz, 1H), 1.77-1.72 (m, 1H), 1.68-1.62 (m, 1H), 1.48 (sep, J=6.7 Hz, 1H), 1.15 (t, J=7.1 Hz, 3H), 0.89 (d, J=6.7 Hz, 3H), 0.87 (d, J=6.7 Hz, 3H). $^{13}$C NMR (126 MHz, DMSO-$d_6$) δ ppm: 169.7, 167.1, 162.1, 143.7, 138.7, 131.9, 131.0, 128.7 (4C), 123.2, 119.4 (2C), 114.3 (2C), 74.6, 70.1, 60.7, 55.6, 52.4, 51.0, 38.1, 37.4, 25.7, 22.7, 21.9, 14.0.

ethyl 2-[[4-[[4-[[(4-isopropoxyphenyl)sulfonylamino]methyl]triazol-1-yl]methyl]phenyl]carbamoyl]-4-methyl-pentanoate (200)

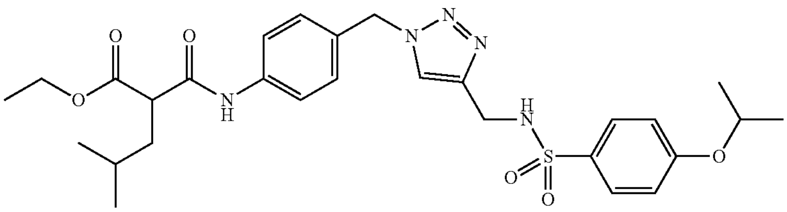 [SMILES: CCOC(=O)C(CC(C)C)C(=O)Nc1ccc(Cn2cc(CNS(=O)(=O)c3ccc(OC(C)C)cc3)nn2)cc1]

Compound 200 was synthesized according to the general procedure E, using azide 83 (75 mg, 0.24 mmol), alkyne 197 (60 mg, 0.24 mmol), copper (II) sulfate pentahydrate (12 mg, 0.05 mmol) and sodium ascorbate (24 mg, 0.12 mmol) in DMF (5 mL) and $H_2O$ (4 mL) overnight. The crude product was purified by flash chromatography on silica gel ($CH_2Cl_2$ to $CH_2Cl_2$/MeOH: 95/5) affording compound 200 as a pale yellow powder (89 mg, 66%). MS (ESI+): m/z=572 $[M+H]^+$. $^1H$ NMR (500 MHz, DMSO-$d_6$) δ ppm: 10.29 (s, 1H), 7.90 (t, J=6.0 Hz, 1H), 7.86 (s, 1H), 7.69-7.65 (m, 2H), 7.59-7.55 (m, 2H), 7.27-7.23 (m, 2H), 7.05-7.00 (m, 2H), 5.46 (s, 2H), 4.71 (sept, J=6.1 Hz, 1H), 4.15-4.03 (m, 2H), 3.98 (d, J=6.1 Hz, 2H), 3.59-3.52 (m, 1H), 1.78-1.61 (m, 2H), 1.53-1.44 (m, 1H), 1.29 (d, J=6.0 Hz, 6H), 1.15 (t, J=7.0 Hz, 3H), 0.92-0.84 (m, 6H). $^{13}C$ NMR (126 MHz, DMSO-$d_6$) δ ppm: 169.7, 167.1, 160.5, 143.7, 138.7, 131.4, 131.0, 128.8 (2C), 128.7 (2C), 123.2, 119.4 (2H), 115.4 (2H), 69.8, 60.6, 52.3, 50.9, 38.1, 37.4, 25.6, 22.6, 22.0, 21.6 (2C), 14.0.

ethyl 2-[[4-[[4-[[(4-isopropylphenyl)sulfonylamino]methyl]triazol-1-yl]methyl]phenyl]carbamoyl]-4-methyl-pentanoate (201)

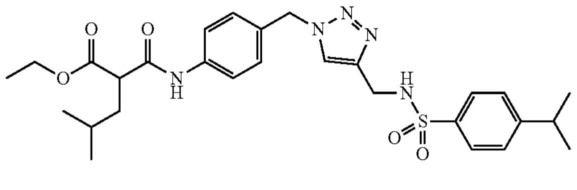 [SMILES: CCOC(=O)C(CC(C)C)C(=O)Nc1ccc(Cn2cc(CNS(=O)(=O)c3ccc(C(C)C)cc3)nn2)cc1]

Compound 201 was synthesized according to the general procedure E, using azide 83 (75 mg, 0.24 mmol), alkyne 198 (56 mg, 0.24 mmol), copper (II) sulfate pentahydrate (12 mg, 0.05 mmol) and sodium ascorbate (24 mg, 0.12 mmol) in DMF (5 mL) and $H_2O$ (4 mL) overnight. The crude product was purified by flash chromatography on silica gel ($CH_2Cl_2$ to $CH_2Cl_2$/MeOH: 95/5) affording compound 201 as a yellow powder (134 mg, quant. yield). MS (ESI+): m/z=556 $[M+H]^+$. $^1H$ NMR (500 MHz, DMSO-$d_6$) δ ppm: 10.29 (s, 1H), 8.01 (t, J=5.3 Hz, 1H), 7.95 (s, 1H), 7.87 (s, 1H), 7.71-7.66 (m, 2H), 7.59-7.55 (m, 2H), 7.43-7.39 (m, 2H), 7.27-7.24 (m, 2H), 5.46 (s, 2H), 4.15-4.03 (m, 2H), 4.03-3.98 (m, 2H), 3.58-3.53 (m, 1H), 2.96 (sept, J=6.9 Hz, 1H), 1.78-1.61 (m, 2H), 1.49 (sept, J=6.9 Hz, 1H), 1.21 (d, J=6.9 Hz, 6H), 1.15 (t, J=7.2 Hz, 3H), 0.91-0.85 (m, 6H). $^{13}C$ NMR (126 MHz, DMSO-$d_6$) δ ppm: 169.7, 167.1, 153.2, 143.7, 138.7, 137.8, 131.0, 128.7 (2C), 127.0 (2C), 126.7 (2C), 123.7, 119.4 (2C), 60.6, 52.3, 50.9, 38.1, 37.4, 33.3, 25.6, 23.5 (2C), 22.6, 21.9, 14.0.

ethyl 2-[[4-[[4-[[[4-(tert-butoxycarbonylamino)phenyl]sulfonylamino]methyl]triazol-1-yl]methyl]phenyl]carbamoyl]-4-methyl-pentanoate (202)

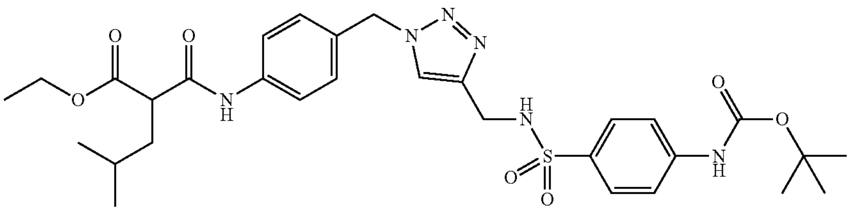 [SMILES: CCOC(=O)C(CC(C)C)C(=O)Nc1ccc(Cn2cc(CNS(=O)(=O)c3ccc(NC(=O)OC(C)(C)C)cc3)nn2)cc1]

Compound 202 was synthesized according to the general procedure E, using azide 83 (100 mg, 0.31 mmol), alkyne 193 (97.5 mg, 0.31 mmol), copper (II) sulfate pentahydrate (15.7 mg, 0.06 mmol) and sodium ascorbate (31.1 mg, 0.16 mmol) in DMF (5.5 mL) and $H_2O$ (4.5 mL) overnight. The crude product was purified by flash chromatography on silica gel ($CH_2Cl_2$ to $CH_2Cl_2$/MeOH: 98/2) affording compound 202 as a yellow powder (160 mg, 80%). MS (ESI+): m/z=629 $[M+H]^+$, 573 $[M+H-tBu]^+$, 529 $[M+H-Boc]^+$. $^1H$ NMR (500 MHz, DMSO-$d_6$) δ ppm: 10.28 (s, 1H), 9.81 (s, 1H), 7.89 (t, J=5.9 Hz, 1H), 7.84 (s, 1H), 7.67-7.65 (m, 2H), 7.62-7.60 (m, 2H), 7.58-7.56 (m, 2H), 7.27-7.25 (m, 2H), 5.45 (s, 2H), 4.13-4.05 (m, 2H), 3.96 (d, J=5.8 Hz, 2H), 3.55 (dd, J=6.2 and 8.7 Hz, 1H), 1.77-1.61 (m, 2H), 1.52-1.46 (m, 10H), 1.15 (t, J=7.1 Hz, 3H), 0.89 (d, J=6.8 Hz, 3H), 0.87 (d, J=6.6 Hz, 3H). $^{13}C$ NMR (126 MHz, DMSO-$d_6$) δ ppm: 169.7, 167.1, 152.6, 143.7, 143.3, 138.7, 132.9, 130.9, 128.8 (2C), 127.8 (2C), 123.2, 119.4 (2C), 117.6 (2C), 79.8, 60.7, 52.4, 50.9, 38.1, 37.3, 28.0, 25.6 (3C), 22.6, 21.9, 14.0.

N-[4-[[4-[[(4-acetylphenyl)sulfonylamino]methyl] triazol-1-yl]methyl]phenyl]-2-(hydroxycarbamoyl)-4-methyl-pentanamide (203)

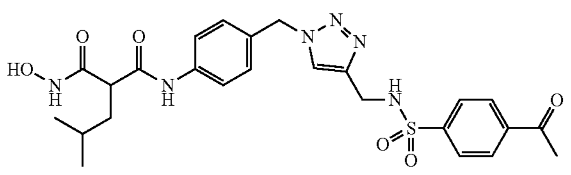 [SMILES: CC(=O)c1ccc(S(=O)(=O)NCc2cn(Cc3ccc(NC(=O)C(CC(C)C)C(=O)NO)cc3)nn2)cc1]

Compound 203 was synthesized according to the general procedure E, using azide Z9 (mg, mmol), alkyne 194 (mg, mmol), copper (II) sulfate pentahydrate (mg, mmol) and sodium ascorbate (mg, mmol) in DMF (5.5 mL) and $H_2O$ (4.5 mL) overnight. The crude product was purified by flash chromatography on silica gel ($CH_2Cl_2$ to $CH_2Cl_2$/MeOH: 98/2) affording compound 202 as a yellow powder (160 mg, 80%). Purity: 100%. MS (ESI+): m/z=543 $[M+H]^+$. $^1$H NMR (500 MHz, DMSO-$d_6$) δ ppm: 10.51 (br s, 1H), 9.80 (s, 1H), 8.97 (s, 1H), 8.31 (br s, 1H), 8.09-8.07 (m, 2H), 7.89 (s, 1H), 7.88-7.87 (m, 2H), 7.56-7.55 (m, 2H), 7.23-7.21 (m, 2H), 5.44 (s, 2H), 4.06 (s, 2H), 3.20 (t, J=7.6 Hz, 1H), 2.63 (s, 3H), 1.70-1.66 (m, 2H), 1.47 (sept, J=6.7 Hz, 1H), 0.87 (d, J=6.7 Hz, 3H), 0.86 (d, J=6.7 Hz, 3H). $^{13}$C NMR (126 MHz, DMSO-$d_6$) δ ppm: 197.4, 167.8, 166.3, 144.1, 143.4, 139.4, 138.7, 130.7, 128.9 (2C), 128.6 (2C), 126.9 (2C), 123.2, 119.5 (2C), 52.3, 49.9, 38.0, 38.0, 27.0, 25.7, 22.4, 22.2.

methyl 4-[[1-[[4-[[2-(hydroxycarbamoyl)-4-methyl-pentanoyl]amino]phenyl]methyl]triazol-4-yl]methyl-sulfamoyl]benzoate (204)

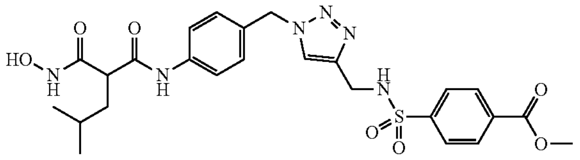 [SMILES: COC(=O)c1ccc(S(=O)(=O)NCc2cn(Cc3ccc(NC(=O)C(CC(C)C)C(=O)NO)cc3)nn2)cc1]

Compound 204 was synthesized according to the general procedure E, using azide Z9 (88 mg, 0.29 mmol), alkyne 194 (73 mg, 0.29 mmol), copper (II) sulfate pentahydrate (14.5 mg, 0.06 mmol) and sodium ascorbate (28.5 mg, 0.14 mmol) in DMF (5 mL) and $H_2O$ (4 mL) overnight. The crude product was purified by flash chromatography on silica gel ($CH_2Cl_2$ to $CH_2Cl_2$/MeOH: 95/5) affording compound 204 as a white powder (47 mg, 28%). Purity: 100%. MS (ESI+): m/z=559 $[M+H]^+$. $^1$H NMR (500 MHz, DMSO-$d_6$) δ ppm: 10.53 (br s, 1H), 9.81 (s, 1H), 8.97 (br s, 1H), 8.34 (br s, 1H), 8.11-8.06 (m, 2H), 7.91-7.86 (m, 2H), 7.85 (s, 1H), 7.58-7.53 (m, 2H), 7.24-7.18 (m, 2H), 5.43 (s, 2H), 4.08 (s, 2H), 3.90 (s, 3H), 3.20 (t, J=7.6 Hz, 1H), 1.68 (t, J=7.5 Hz, 2H), 1.47 (sept, J=6.7 Hz, 1H), 0.90-0.85 (m, 6H). $^{13}$C NMR (126 MHz, DMSO-$d_6$) δ ppm: 167.8, 166.3, 165.2, 144.5, 143.4, 138.7, 132.8, 130.7, 129.9 (2C), 128.6 (2C), 127.0 (2C), 123.2, 119.5 (2C), 52.6, 52.3, 49.9, 38.0 (2C), 25.7, 22.4, 22.2.

2-(hydroxycarbamoyl)-N-[4-[[4-[[[4-(2-methoxy-ethoxy)phenyl]sulfonylamino]methyl]triazol-1-yl] methyl]phenyl]-4-methyl-pentanamide (205)

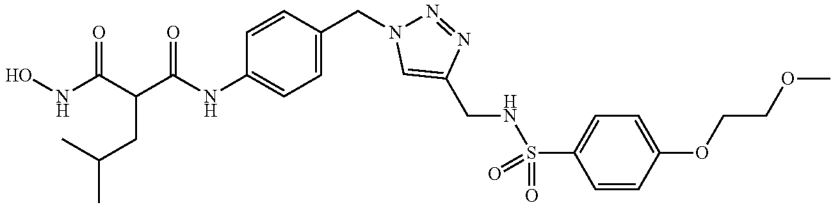 [SMILES: COCCOc1ccc(S(=O)(=O)NCc2cn(Cc3ccc(NC(=O)C(CC(C)C)C(=O)NO)cc3)nn2)cc1]

Compound 205 was synthesized according to the general procedure D, using ester 199 (145 mg, 0.25 mmol), KCN (4.9 mg, 0.08 mmol) and aq. $NH_2OH$ (2.5 mL, 50% w/w in water) in MeOH (2.5 mL) overnight. The crude product was purified by flash chromatography on silica gel ($CH_2Cl_2$ to $CH_2Cl_2$/MeOH: 95/5) affording compound 205 as a white solid after lyophilization (65 mg, 45%). Purity: 100%. MS (ESI+): m/z=575 $[M+H]^+$. $^1$H NMR (500 MHz, DMSO-$d_6$) δ ppm: 10.53 (br s, 1H), 9.83 (s, 1H), 8.97 (br s, 1H), 7.92 (br s, 1H), 7.84 (s, 1H), 7.71-7.69 (m, 2H), 7.57-7.56 (m, 2H), 7.24-7.22 (m, 2H), 7.07-7.05 (m, 2H), 5.45 (s, 2H), 4.18-4.16 (m, 2H), 3.98 (s, 2H), 3.68-3.66 (m, 2H), 3.31 (s, 3H), 3.21 (t, J=7.6 Hz, 1H), 1.68 (t, J=7.2 Hz, 2H), 1.47 (sep, J=6.6 Hz, 1H), 0.88-0.86 (m, 6H). $^{13}$C NMR (126 MHz, DMSO-$d_6$) δ ppm: 167.8, 166.3, 162.1, 143.7, 138.7, 131.9, 130.8, 128.7 (2C), 128.6 (2C), 123.2, 119.5 (2C), 114.3 (2C), 74.6, 70.1, 55.6, 52.4, 49.9, 38.1, 38.0, 25.7, 22.4, 22.3.

2-(hydroxycarbamoyl)-N-[4-[[4-[[(4-isopropoxyphenyl)sulfonylamino]methyl]triazol-1-yl]methyl]phenyl]-4-methyl-pentanamide (206)

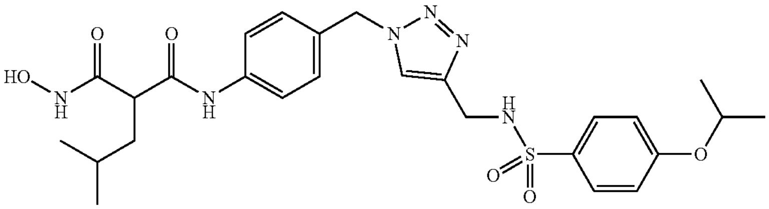 [SMILES: CC(C)CC(C(=O)NO)C(=O)Nc1ccc(Cn2cc(CNS(=O)(=O)c3ccc(OC(C)C)cc3)nn2)cc1]

Compound 206 was synthesized according to the general procedure D, using ester 200 (90 mg, 0.16 mmol), KCN (2 mg, 0.03 mmol) and aq. $NH_2OH$ (2 mL, 50% w/w in water) in MeOH (2 mL) overnight. The crude product was purified by flash chromatography on silica gel ($CH_2Cl_2$ to $CH_2Cl_2$/MeOH: 95/5) affording compound 206 as a white solid after lyophilization (21 mg, 24%). Purity: 100%. MS (ESI+): m/z=559 $[M+H]^+$. $^1H$ NMR (500 MHz, DMSO-$d_6$) δ ppm: 10.53 (br s, 1H), 9.82 (br s, 1H), 8.97 (br s, 1H), 7.90 (br s, 1H), 7.85 (s, 1H), 7.72-7.63 (m, 2H), 7.61-7.53 (m, 2H), 7.28-7.19 (m, 2H), 7.09-6.99 (m, 2H), 5.45 (s, 2H), 4.76-4.66 (m, 1H), 3.98 (s, 2H), 3.26-3.16 (m, 1H), 1.77-1.62 (m, 2H), 1.56-1.41 (m, 1H), 1.35-1.24 (m, 6H), 0.87 (s, 6H). $^{13}C$ NMR (126 MHz, DMSO-$d_6$) δ ppm: 168.3, 166.7, 160.9, 144.2, 139.2, 131.9, 131.2, 129.3 (2C), 129.1 (2C), 123.6, 120.0 (2C), 115.9 (2C), 70.3, 52.8, 50.4, 38.6, 38.5, 26.2, 22.9, 22.7, 22.1 (2C).

2-(hydroxycarbamoyl)-N-[4-[[4-[[(4-isopropylphenyl)sulfonylamino]methyl]triazol-1-yl]methyl]phenyl]-4-methyl-pentanamide (207)

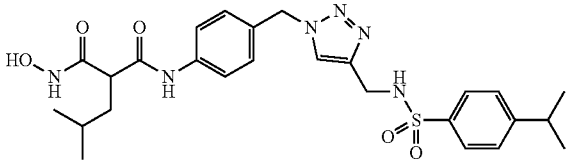 [SMILES: CC(C)CC(C(=O)NO)C(=O)Nc1ccc(Cn2cc(CNS(=O)(=O)c3ccc(C(C)C)cc3)nn2)cc1]

Compound 207 was synthesized according to the general procedure D, using ester 201 (125 mg, 0.22 mmol), KCN (3 mg, 0.05 mmol) and aq. $NH_2OH$ (2.5 mL, 50% w/w in water) in MeOH (2.5 mL) overnight. The crude product was purified by flash chromatography on silica gel ($CH_2Cl_2$ to $CH_2Cl_2$/MeOH: 95/5) affording compound 207 as a white solid after lyophilization (26 mg, 21%). Purity: 97%. MS (ESI+): m/z=543 $[M+H]^+$. $^1H$ NMR (500 MHz, DMSO-$d_6$) δ ppm: 10.43 (br s, 1H), 7.85 (s, 1H), 7.74-7.65 (m, 2H), 7.60-7.52 (m, 2H), 7.45-7.38 (m, 2H), 7.27-7.19 (m, 2H), 5.44 (s, 2H), 4.00 (s, 2H), 3.11-3.03 (m, 1H), 3.01-2.91 (m, 1H), 1.73-1.54 (m, 2H), 1.54-1.44 (m, 1H), 1.29-1.14 (m, 6H), 0.86 (s, 6H). $^{13}C$ NMR (126 MHz, DMSO-$d_6$) δ ppm: 169.2, 165.8, 153.1, 143.7, 138.9, 137.8, 130.4, 128.6 (2C), 127.0 (2C), 126.7 (2C), 123.2, 119.3 (2C), 52.4, 49.8, 38.9, 38.1, 33.4, 25.6, 23.5 (2C), 22.6, 22.1.

tert-butyl N-[4-[[1-[[4-[[2-(hydroxycarbamoyl)-4-methyl-pentanoyl]amino]phenyl]methyl]triazol-4-yl]methylsulfamoyl]phenyl]carbamate (208)

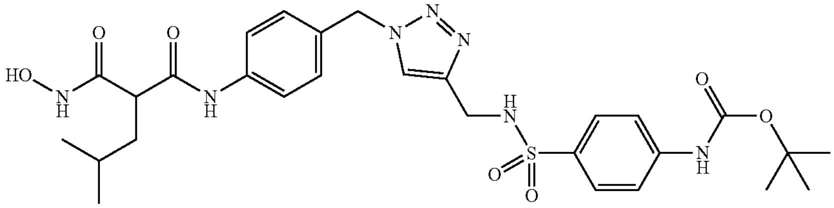 [SMILES: CC(C)CC(C(=O)NO)C(=O)Nc1ccc(Cn2cc(CNS(=O)(=O)c3ccc(NC(=O)OC(C)(C)C)cc3)nn2)cc1]

Compound 208 was synthesized according to the general procedure D, using ester 202 (150 mg, 0.24 mmol), KCN (4.6 mg, 0.07 mmol) and aq. $NH_2OH$ (2 mL, 50% w/w in water) in MeOH (2 mL) overnight. The crude product was purified by flash chromatography on silica gel ($CH_2Cl_2$ to $CH_2Cl_2$/MeOH: 95/5) affording compound 208 as a white solid after lyophilization (72 mg, 49%). Purity: 100%. MS (ESI+): m/z=616 $[M+H]^+$, 560 $[M\text{-tBu}+H]^+$, 516 $[M\text{-Boc}+H]^+$. $^1H$ NMR (500 MHz, DMSO-$d_6$) δ ppm: 10.51 (br s, 1H), 9.81 (s, 1H), 9.80 (s, 1H), 8.97 (s, 1H), 7.89 (t, J=5.5 Hz, 1H), 7.83 (s, 1H), 7.67-7.65 (m, 2H), 7.62-7.60 (m, 2H), 7.57-7.55 (m, 2H), 7.25-7.23 (m, 2H), 5.44 (s, 2H), 3.96 (d, J=5.0 Hz, 2H), 3.20 (t, J=7.6 Hz, 1H), 1.68 (t, J=7.2 Hz, 2H), 1.48 (s, 9H), 1.47-1.44 (m, 1H), 0.87 (d, J=6.6 Hz, 3H), 0.86 (d, J=6.6 Hz, 3H). $^{13}C$ NMR (126 MHz, DMSO-$d_6$) δ ppm: 167.8, 166.3, 152.6, 143.7, 143.3, 138.7, 132.9, 130.7, 128.7 (2C), 127.8 (2C), 123.2, 119.6 (2C), 117.6 (2C), 79.9, 52.4, 49.9, 38.1, 38.0, 28.0 (3C), 25.7, 22.4, 22.2.

2-(hydroxycarbamoyl)-N-[4-[[4-[[(4-isopropylphenyl)sulfonylamino]methyl]triazol-1-yl]methyl]phenyl]-4-methyl-pentanamide (209)

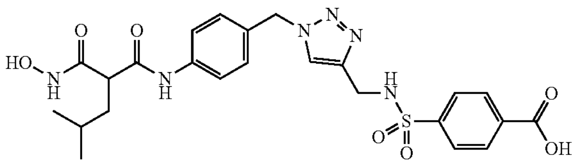 [SMILES: CC(C)CC(C(=O)NO)C(=O)Nc1ccc(Cn2cc(CNS(=O)(=O)c3ccc(C(=O)O)cc3)nn2)cc1]

Compound 204 (35 mg, 0.06 mmol) was dissolved in THE (1 mL). A solution of LiOH (2.8 mg, 0.06 mg, 1 eq.) in $H_2O$ (1 mL) was added dropwise. The mixture was stirred overnight. Solvents were removed under reduced pressure and the residue was dissolved in DMSO and filtered, before purification by preparative HPLC (H2O+0.05% FA/MeCN+0.05% FA: 95:5 to 5:95) to give compound 209 as a white powder after lyophilization (22 mg, 66%). Purity: 100%. MS (ESI+): m/z=545 $[M+H]^+$. $^1H$ NMR (500 MHz, DMSO-$d_6$) δ ppm: 13.43 (br s, 1H), 10.53 (s, 1H), 9.81 (s, 1H), 8.98 (br s, 1H), 8.29 (t, J=5.4 Hz, 1H), 8.12-8.06 (m, 2H), 7.90-7.86 (m, 2H), 7.86 (s, 1H), 7.59-7.54 (m, 2H), 7.25-7.20 (m, 2H), 5.44 (s, 2H), 4.06 (d, J=5.8 Hz, 2H), 3.20 (t, J=7.6 Hz, 1H), 1.68 (t, J=7.3 Hz, 2H), 1.47 (sept, J=6.7 Hz, 1H), 0.91-0.84 (m, 6H). $^{13}C$ NMR (126 MHz, DMSO-$d_6$) δ ppm: 167.8, 166.3, 166.3, 144.0, 143.4, 138.7, 134.2, 130.7, 130.0 (2C), 128.7 (2C), 126.8 (2C), 123.2, 119.6 (2C), 52.3, 49.9, 38.1, 38.0, 25.7, 22.4, 22.2.

N-[4-[[4-[[(4-aminophenyl)sulfonylamino]methyl]triazol-1-yl]methyl]phenyl]-2-(hydroxycarbamoyl)-4-methyl-pentanamide (210)

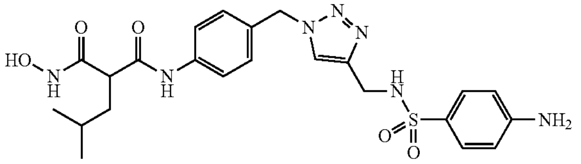 [SMILES: CC(C)CC(C(=O)NO)C(=O)Nc1ccc(Cn2cc(CNS(=O)(=O)c3ccc(N)cc3)nn2)cc1]

Compound 210 was synthesized according to the general procedure G, using the Boc-protected intermediate 208 (65 mg, 0.1 mmol), 4 N HCl in dioxane (2 mL) in a MeOH (2 mL) during 2 hours. The residue was purified through preparative HPLC ($H_2O$+0.05% FA/ACN+0.05% FA: 95:5 to 5:95) to give compound 210 as a white solid after lyophilization (16 mg, 30%). Purity: 100%. MS (ESI−): m/z=514 $[M-H]^-$. $^1H$ NMR (500 MHz, DMSO-$d_6$) δ ppm: 10.53 (s, 1H), 9.81 (s, 1H), 8.97 (s, 1H), 7.81 (s, 1H), 7.57-7.54 (m, 3H), 7.41-7.39 (m, 2H), 7.26-7.24 (m, 2H), 6.60-6.58 (m, 2H), 5.94 (s, 2H), 5.45 (s, 2H), 3.90 (d, J=6.1 Hz, 2H), 3.21 (t, J=7.6 Hz, 1H), 1.69-1.66 (m, 2H), 1.47 (sep, J=6.6 Hz, 1H), 0.87 (d, J=6.6 Hz, 3H), 0.86 (d, J=6.6 Hz, 3H). $^{13}C$ NMR (126 MHz, DMSO-$d_6$) δ ppm: 167.8, 166.3, 152.6, 144.1, 138.7, 130.8, 128.7 (2C), 128.6 (2C), 125.1, 123.1, 119.6 (2C), 112.6 (2C), 52.4, 49.9, 38.2, 38.0, 25.7, 22.4, 22.2.

2-ethoxycarbonyl-5-methyl-hexanoic acid (211-a)

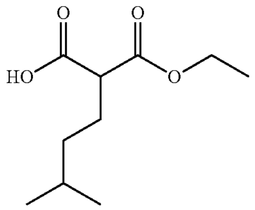

Compound 211-a was synthesized according to the general procedure F, using diethylmalonate (2000 mg, 8.68 mmol) and NaOH (416.6 mg, 10.42 mmol) in EtOH/$H_2O$ (20 mL, 16:4 v/v) overnight. Compound 211-a was obtained as colorless oil (1500 mg, 85%) and was used in the next step without further purification. MS (ESI+): m/z=203 $[M+H]^+$. $^1H$ NMR (DMSO-$d_6$) δ ppm: 12.75 (br s, 1H), 4.10 (q, J=7.1 Hz, 2H), 3.27 (t, J=7.5 Hz, 1H), 1.76-1.67 (m, 2H), 1.51 (sept, J=6.6 Hz, 1H), 1.17 (t, J=7.1 Hz, 3H), 1.15-1.08 (m, 2H), 0.84 (d, J=6.6 Hz, 6H). $^{13}C$ NMR (DMSO-$d_6$) δ ppm: 170.5, 169.5, 60.6, 51.5, 35.8, 27.3, 26.3, 22.3, 22.3, 14.0.

3-methoxy-2-methyl-3-oxo-propanoic acid (212-a)

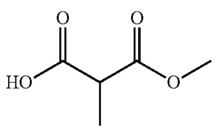

Compound 212-a was synthesized according to the general procedure F, using dimethylmalonate (1300 mg, 8.9 mmol) and NaOH (427 mg, 10.7 mmol) in MeOH/$H_2O$ (20 mL, 16:4 v/v) overnight. Compound 212-a was obtained as colorless oil (1020 mg, 85%) and was used in the next step without further purification. MS (ESI+): no ionization. $^1H$ NMR (500 MHz, DMSO-$d_6$) δ ppm: 12.83 (s, 1H), 3.64 (s, 3H), 3.45 (q, J=10.8 Hz, 1H), 1.24 (d, J=7.2 Hz, 3H). $^{13}C$ NMR (126 MHz, DMSO-$d_6$) δ ppm: 171.2, 170.7, 52.1, 45.4, 13.6.

ethyl 2-[[4-(azidomethyl)phenyl]carbamoyl]-5-methyl-hexanoate (211)

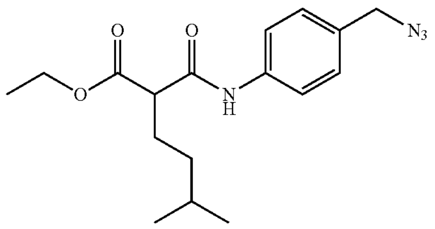 [SMILES: CCOC(=O)C(CCC(C)C)C(=O)Nc1ccc(CN=[N+]=[N-])cc1]

Compound 211 was synthesized according to the general procedure B, using carboxylic acid 211-a (300 mg, 0.67 mmol), aniline 171 (148.4 mg, 0.8 mmol), HBTU (379.2 mg, 1.0 mmol) and trimethylamine (460 μL, 3.35 mmol) in DMF (3 mL) overnight. The crude product was purified by flash chromatography on silica gel (cHex to cHex/EtOAc: 8/2) affording compound 211 as a yellow oil (93 mg, 42%). MS (ESI+): m/z=333 $[M+H]^+$.

methyl 3-[4-(azidomethyl)anilino]-2-methyl-3-oxo-propanoate (212)

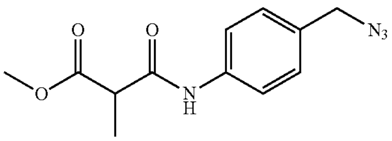 [SMILES: COC(=O)C(C)C(=O)Nc1ccc(CN=[N+]=[N-])cc1]

Compound 212 was synthesized according to the general procedure B, using carboxylic acid 212-a (250 mg, 1.89 mmol), aniline 171 (419 mg, 2.27 mmol), HBTU (1080 mg, 2.84 mmol) and trimethylamine (1290 μL, 9.46 mmol) in DMF (5 mL) overnight. The crude product was purified by flash chromatography on silica gel (cHex to cHex/EtOAc: 5/5) affording compound 212 as a pale yellow solid (82 mg, 16%). MS (ESI+): m/z=263 $[M+H]^+$. $^1H$ NMR (500 MHz, DMSO-$d_6$) δ ppm: 10.28 (s, 1H), 7.62-7.60 (m, 2H), 7.33-7.31 (m, 2H), 4.38 (s, 2H), 3.64 (s, 3H), 3.63-3.60 (m, 1H), 1.31 (d, J=7.1 Hz, 3H). $^{13}C$ NMR (126 MHz, DMSO-$d_6$) δ ppm: 170.8, 168.1, 138.8, 130.5, 129.2 (2C), 119.3 (2C), 53.2, 52.1, 46.7, 13.9.

N-[4-(azidomethyl)phenyl]-2-(hydroxycarbamoyl)-5-methyl-hexanamide (214)

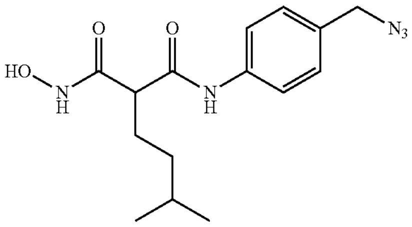 [SMILES: CC(C)CCC(C(=O)NO)C(=O)Nc1ccc(CN=[N+]=[N-])cc1]

Compound 214 was synthesized according to the general procedure D, using ester 83 (85 mg, 0.26 mmol), KCN (3.4 mg, 0.05 mmol) and aq. $NH_2OH$ (2 mL, 50% w/w in water)

in MeOH (2 mL) 48 hours. The crude product was purified by flash chromatography on silica gel ($CH_2Cl_2$ to $CH_2Cl_2$/MeOH: 9/1) affording compound 214 as a beige powder (45 mg, 53%). MS (ESI+): m/z=320 $[M+H]^+$. $^1H$ NMR (500 MHz, DMSO-$d_6$) δ ppm: 10.56 (s, 1H), 9.90 (s, 1H), 8.99 (s, 1H), 7.62-7.60 (m, 2H), 7.32-7.30 (m, 2H), 4.37 (s, 2H), 3.08 (t, J=7.2 Hz, 1H), 1.80-1.75 (m, 2H), 1.54-1.49 (m, 1H), 1.13-1.08 (m, 2H), 0.85 (d, J=6.3 Hz, 6H). $^{13}C$ NMR (126 MHz, DMSO-$d_6$) δ ppm: 167.9, 166.2, 138.8, 130.3, 129.2 (2C), 119.4 (2C), 53.3, 51.8, 36.2, 27.5, 27.1, 22.5 (2C).

2-(hydroxycarbamoyl)-N-[4-[[4-[[(4-iodophenyl)sulfonylamino]methyl]triazol-1-yl]methyl]phenyl]-5-methyl-hexanamide (215)

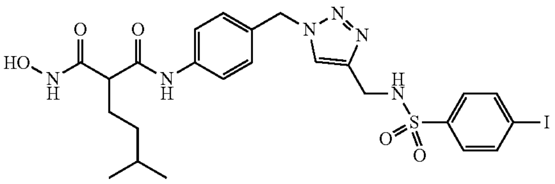 [SMILES: CC(C)CCC(C(=O)NO)C(=O)Nc1ccc(Cn2cc(CNS(=O)(=O)c3ccc(I)cc3)nn2)cc1]

Compound 215 was synthesized according to the general procedure E, using azide 214 (40 mg, 0.13 mmol), alkyne 117 (41.7 mg, 0.13 mmol), copper (II) sulfate pentahydrate (6.5 mg, 0.03 mmol) and sodium ascorbate (12.9 mg, 0.07 mmol) in DMF (3 mL) and $H_2O$ (2 mL) overnight. The crude product was purified by flash chromatography on silica gel ($CH_2Cl_2$ to $CH_2Cl_2$/MeOH: 9/1) affording compound 214 as a white solid after lyophilization (23 mg, 30%). Purity: 100%. MS (ESI+): m/z=641 $[M+H]^+$. $^1H$ NMR (500 MHz, DMSO-$d_6$) δ ppm: 10.51 (br s, 1H), 9.83 (s, 1H), 8.96 (s, 1H), 8.18 (br s, 1H), 7.93-7.91 (m, 2H), 7.84 (s, 1H), 7.58-7.57 (m, 2H), 7.51-7.50 (m, 2H), 7.25-7.23 (m, 2H), 5.45 (s, 2H), 4.03 (s, 2H), 3.05 (t, J=7.3 Hz, 1H), 1.80-1.74 (m, 2H), 1.54-1.49 (m, 1H), 1.15-1.08 (m, 2H), 0.85 (d, J=6.4 Hz, 6H). $^{13}C$ NMR (126 MHz, DMSO-$d_6$) δ ppm: 167.8, 166.2, 143.4, 140.0, 138.7, 138.0 (2C), 130.7, 128.7 (2C), 128.3 (2C), 123.2, 119.5 (2C), 100.4, 52.4, 51.8, 38.0, 36.1, 27.4, 27.2, 22.4 (2C).

methyl 3-[4-[[4-[[(4-iodophenyl)sulfonylamino]methyl]triazol-1-yl]methyl]anilino]-2-methyl-3-oxo-propanoate (216)

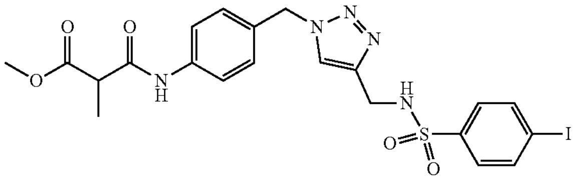 [SMILES: COC(=O)C(C)C(=O)Nc1ccc(Cn2cc(CNS(=O)(=O)c3ccc(I)cc3)nn2)cc1]

Compound 216 was synthesized according to the general procedure E, using azide 212 (70 mg, 0.27 mmol), alkyne 117 (85.6 mg, 0.27 mmol), copper (II) sulfate pentahydrate (6.5 mg, 0.03 mmol) and sodium ascorbate (24.6 mg, 0.13 mmol) in DMF (5.5 mL) and $H_2O$ (4.5 mL) overnight. The crude product was purified by flash chromatography on silica gel ($CH_2Cl_2$ to $CH_2Cl_2$/MeOH: 98/2) affording compound 216 as a white solid (146 mg, 92%). MS (ESI+):

m/z=584 $[M+H]^+$. $^1H$ NMR (500 MHz, DMSO-$d_6$) δ ppm: 10.27 (s, 1H), 8.19 (t, J=5.8 Hz, 1H), 7.93-7.92 (m, 2H), 7.84 (s, 1H), 7.59-7.57 (m, 2H), 7.51-7.50 (m, 2H), 7.26-7.24 (m, 2H), 5.45 (s, 2H), 4.03 (d, J=5.8 Hz, 2H), 3.63 (s, 3H), 3.61-3.58 (m, 1H), 1.30 (d, J=7.1 Hz, 3H). $^{13}C$ NMR (126 MHz, DMSO-$d_6$) δ ppm: 170.7, 168.1, 143.4, 140.0, 138.8, 138 (2C), 130.8, 128.8 (2C), 128.3 (2C), 123.2, 119.4 (2C), 100.4, 52.4, 52.1, 46.7, 38.0, 13.9.

3-(hydroxyamino)-N-[4-[[4-[[(4-iodophenyl)sulfonylamino]methyl]triazol-1-yl]methyl]phenyl]-2-methyl-3-oxo-propanamide (217)

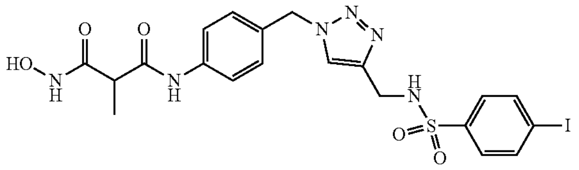 [SMILES: CC(C(=O)NO)C(=O)Nc1ccc(Cn2cc(CNS(=O)(=O)c3ccc(I)cc3)nn2)cc1]

Compound 217 was synthesized according to the general procedure D, using ester 216 (139 mg, 0.24 mmol), KCN (3.1 mg, 0.05 mmol) and aq. $NH_2OH$ (2 mL, 50% w/w in water) in MeOH (2 mL) overnight. The crude product was purified by flash chromatography on silica gel ($CH_2Cl_2$ to $CH_2Cl_2$/MeOH: 9/1) affording compound 217 as a beige powder (72 mg, 52%). Purity: 96%. MS (ESI+): m/z=585 $[M+H]^+$. $^1H$ NMR (500 MHz, DMSO-$d_6$) δ ppm: 9.99 (s, 1H), 9.31 (br s, 2H), 8.26 (s, 1H), 7.93-7.91 (m, 2H), 7.83 (s, 1H), 7.59-7.57 (m, 2H), 7.51-7.49 (m, 2H), 7.24-7.23 (m, 2H), 5.44 (s, 2H), 4.03 (m, 2H), 3.29-3.25 (m, 1H), 1.26 (d, J=7.1 Hz, 3H). $^{13}C$ NMR (126 MHz, DMSO-$d_6$) δ ppm: 168.6, 166.9, 143.4, 140.1, 139.0, 138.0 (2C), 130.5, 128.7 (2C), 128.3 (2C), 123.2, 119.4 (2C), 100.4, 52.4, 45.2, 38.0, 14.3.

II. Biology

In Vitro LasB Activity Assay:

The LasB activity assay was performed as described previously (Nishino N, Powers J C. *Pseudomonas aeruginosa* elastase. Development of a new substrate, inhibitors, and an affinity ligand. J Biol Chem. 1980 Apr. 25; 255(8): 3482-6) using the fluorogenic substrate 2-Aminobenzoyl-L-Alanyl-Glycyl-L-Leucyl-L-Alanyl-para-Nitro-Benzyl-Amide, purchased from Peptides International (Louisville, KY, USA) and vivitide, LLC (Gardner, MA, USA).

Fluorescence intensity was measured for 60 min at 37° C. in black 384-well microtiter plates (Greiner BioOne, Kremsmünster, Austria) using a CLARIOstar microplate reader (BMG Labtech, Ortenberg, Germany) with an excitation wavelength of 340±nm and an emission wavelength of 415±20 nm. The assay was performed in a final volume of 50 µL of assay buffer (50 mM Tris, pH 7.2, 2.5 mM $CaCl_2$), 0.075% Pluronic F-127, 5% DMSO) containing LasB at a final concentration of or 0.3 nM and the substrate at 150 µM. Before substrate addition, compounds were preincubated with the enzyme at 37° C. for 15 min. Experiments were performed in duplicates and repeated for at least two times. Blank controls without enzyme were performed. After blank subtraction, the slope of samples containing inhibitors (v) was divided by the slope of a simultaneously started uninhibited enzymatic reaction (v0). $IC_{50}$ values were determined with nonlinear regression using GraphPad Prism 5 (Graph Pad Software, San Diego, CA, USA) and are given as mean values ±standard deviation (SD). The slope factor was constrained to 1.

TABLE 1

Activity against LasB

| Compound | $IC_{50}$ LasB (nM) |
|---|---|
| Z9 | 16.9 ± 0.6 |
| Hit L3 | 13.9 ± 0.3 |
| Hit L5 | 13.8 ± 0.3 |
| Hit L4 | 6.6 ± 0.2 |
| Hit L2 | 5.3 ± 0.1 |
| Hit L1 | 2.4 ± 0.1 |
| 131 | 2.3 ± 0.1 |
| 139 | 19.3 ± 0.6 |
| 132 | 22.8 ± 0.1 |
| 133 | 9.8 ± 0.4 |
| 140 | 55.9 ± 2.3 |
| 134 | 8.4 ± 0.5 |
| 135 | 9.8 ± 0.3 |
| 136 | 1.4 ± 0.1 |
| 137 | 16.9 ± 1.3 |
| 138 | 37.8 ± 2.9 |
| 160 | 3.8 ± 0.1 |
| 161 | 1.7 ± 0.1 |
| 162 | 1.9 ± 0.1 |
| 163 | 4.3 ± 0.1 |
| 164 | 2.4 ± 0.1 |
| 165 | 1.6 ± 0.1 |
| 166 | 5.2 ± 0.3 |
| 167 | 5.5 ± 0.3 |
| 168 | 2.7 ± 0.2 |
| 169 | 5.2 ± 0.2 |
| 182 | 1.9 ± 0.1 |
| 183 | 9.9 ± 0.3 |
| 179 | 1.0 ± 0.6 |
| 185 | 6.5 ± 0.2 |
| 190 | 7.8 ± 0.1 |
| 191 | 7.9 ± 0.1 |
| 192 | 6.8 ± 0.1 |
| 203 | 7.9 ± 0.2 |
| 204 | 13.0 ± 0.4 |
| 205 | 29.5 ± 0.7 |
| 206 | 7.8 ± 0.3 |
| 207 | 3.1 ± 0.1 |
| 208 | 4.2 ± 0.2 |
| 209 | 44.6 ± 1.1 |
| 210 | 7.7 ± 0.2 |
| 215 | 48.5 ± 1.4 |
| 217 | 278.3 ± 9.7 |

MIC Determination Assay:

Assays regarding the determination of the minimum inhibitory concentration (MIC) were performed as described previously (Elgaher W A M, Fruth M, Groh M, Haupenthal J, Hartmann R W. Expanding the scaffold for bacterial RNA polymerase inhibitors: design, synthesis and structure-activity relationships of ureido-heterocyclic-carboxylic acids. RSC Adv. 2013 Dec. 3; 4(5):2177-94). The experiments were based on the *P. aeruginosa* strain PA14. For the case that no MIC value could be determined due to activity reasons, percentage (%) inhibition at 100 µM (or lower, depending on the solubility of the compounds) was calculated. The $OD_{600}$ was measured 0 and 16 h after inhibitor addition in a CLARIOstar Platereader (BMG Labtech, Ortenberg, Germany).

Kinetic Turbidimetric Solubility Assay:

The desired compounds were sequentially diluted in DMSO in a 96-well plate. 1.5 µL of each well were transferred into another 96-well plate and mixed with 148.5 µL of PBS. Plates were shaken for 5 min at 600 rpm at room temperature, and the absorbance at 620 nm was measured. Absorbance values were normalized by blank subtraction and plotted using GraphPad Prism 8.4.2 (GraphPad Software, San Diego, CA, USA). Solubility (S) was determined based on the First X value of AUC function using a threshold of 0.005.

Metabolic Stability in Mouse Liver S9 Fraction Assay:

For the evaluation of combined phase I and phase II metabolic stability, the compound (1 μM) was incubated with 1 mg/mL pooled liver S9 fraction (Xenotech), 2 mM NADPH, 1 mM UDPGA, 10 mM MgCl2, 5 mM GSH and 0.1 mM PAPS at 37° C. for 0, 5, 15, 30 and 60 min. The metabolic stability of Testosterone (1 μM), verapamil (1 μM) and ketoconazol (1 μM) were determined in parallel to confirm the enzymatic activity of the S9 fraction. The incubation was stopped by precipitation of S9 enzymes with 2 volumes of cold acetonitrile containing internal standard (150 nM Diphenhydramine). Samples were stored on ice for 10 min and precipitated protein was removed by centrifugation (15 min, 4° C., 4,000 rpm). The remaining test compound at different time points was analyzed by LC-MS/MS (TSQ Quantum Access MAX, Thermo Fisher, Dreieich, Germany) and used to determine half-life (t½).

TABLE 2

Comparison study between Hit L1, 131 and 136 according to their activity, solubility and metabolic stability in mouse

| Compound | Structure | $IC_{50}$ LasB (nM) | Solubility (μM) | Met Stab in mouse liver S9 $t_{1/2}$ [min] |
|---|---|---|---|---|
| Hit L1 | 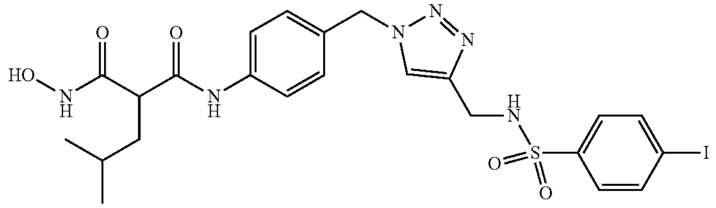 [SMILES: CC(C)CC(C(=O)NO)C(=O)Nc1ccc(Cn2cc(CNS(=O)(=O)c3ccc(I)cc3)nn2)cc1] | 2.4 ± 0.1 | 106 ± 19 | 30.1 ± 1.5 |
| 131 | 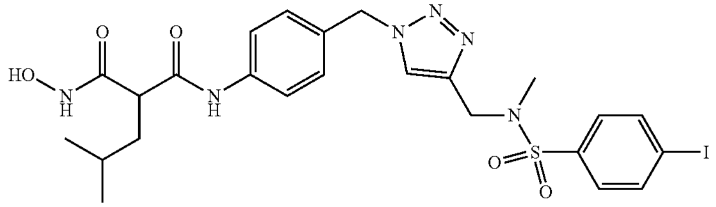 [SMILES: CC(C)CC(C(=O)NO)C(=O)Nc1ccc(Cn2cc(CN(C)S(=O)(=O)c3ccc(I)cc3)nn2)cc1] | 2.3 ± 0.1 | <200 | 37.5 ± 2.5 |
| 136 | 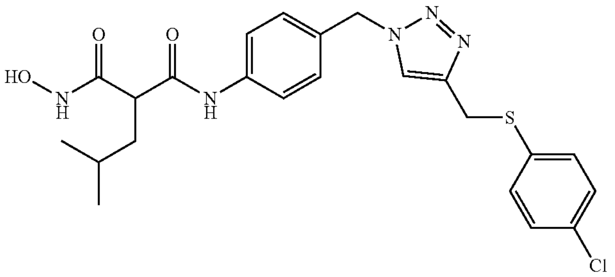 [SMILES: CC(C)CC(C(=O)NO)C(=O)Nc1ccc(Cn2cc(CSc3ccc(Cl)cc3)nn2)cc1] | 1.4 ± 0.1 | <200 | 3.3 ± 0.2 |

TABLE 3

Comparative study between Hit L1, 160, 161, 165 and 169 according to their activity, solubility, clogP and metabolic stability in mouse.

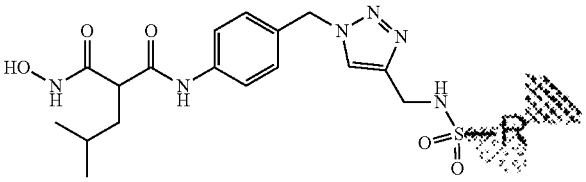

| Compound | R | $IC_{50}$ LasB (nM) | cLogP* | Solubility [μM] | Met Stab in mouse liver S9 $t_{1/2}$ [min] |
|---|---|---|---|---|---|
| Hit L1 | 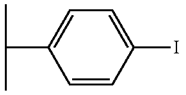 | 2.4 ± 0.1 | 1.5 | 142 | 30.1 ± 1.5 |

TABLE 3-continued

Comparative study between Hit L1, 160, 161, 165 and 169 according to their activity, solubility, clogP and metabolic stability in mouse.

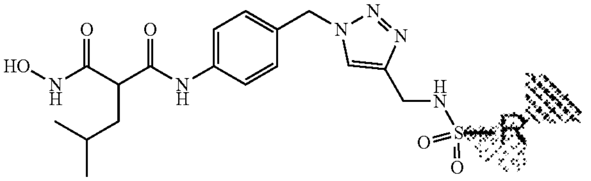

| Compound | R | $IC_{50}$ LasB (nM) | cLogP* | Solubility [μM] | Met Stab in mouse liver S9 $t_{1/2}$ [min] |
|---|---|---|---|---|---|
| 161 | 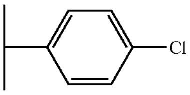 | 1.7 ± 0.1 | 1.6 | >200 | 33.9 ± 1.0 |
| 165 | 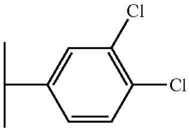 | 1.6 ± 0.1 | 2.2 | 117 | 10.7 ± 0.6 |
| 160 | 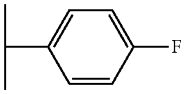 | 3.8 ± 0.1 | 1.1 | >200 | 65.5 ± 0.7 |
| 169 | 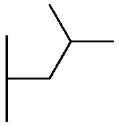 | 5.2 ± 0.2 | 0.9 | >200 | >120 |

*cLogP values were calculated using Datawarrior.

Selectivity Assay:

Inhibition of MMPs

MMPs-1, -2, -3, -7, -8 and -14 along with the SensoLyte 520 Generic MMP Activity Kit*Fluorimetric* were purchased from AnaSpec (Fremont, CA, USA). The assay was performed as described previously (Schönauer E, Kany A M, Haupenthal J, Hüsecken K, Hoppe I J, Voos K, et al. Discovery of a Potent Inhibitor Class with High Selectivity toward Clostridial Collagenases. J Am Chem Soc. 2017 Sep. 13; 139(36):12696-703) using batimastat as a positive control according to the guidelines of the manufacturer.

HDAC Inhibition

HDAC3 and HDAC8 Inhibitor Screening Assay kits were purchased from Sigma-Aldrich. The assay was performed according to the guidelines of the manufacturer using trichostatin as a positive control. Fluorescence signals were measured in a CLARIOstar plate reader (BMG Labtech).

TACE

The ADAM-17 (TACE) Inhibitor Screening Assay Kit was purchased from Sigma-Aldrich. The assay was performed according to the guidelines of the manufacturer using ilomastat as a positive control. Fluorescence signals were measured in a CLARIOstar plate reader (BMG Labtech).

COX-1

COX-1 Inhibitor Screening Assay Kit was purchased from Abcam. The assay was performed according to the guidelines of the manufacturer. Fluorescence signals were measured in a CLARIOstar plate reader (BMG Labtech).

Cytotoxicity Assay:

HepG2, HEK293 or A549 cells ($2\times10^5$ cells per well) were seeded in 24-well, flat-bottomed plates. Culturing of cells, incubations, and OD measurements were performed as described previously (Int. J. Cancer 2007, 121, 206-210). Twenty-four hours after seeding the cells, the incubation was started by the addition of test compound in a final DMSO concentration of 1%. The living cell mass was determined after 48 h. At least two independent measurements were performed for each compound.

TABLE 4

Selectivity and cytotoxicity profiles of Hit L1, 160, 169 and Z9 with their antibacterial activities against *P. aeruginosa* PA-14.

| | | Hit L1 | 160 | 169 | Z9 |
|---|---|---|---|---|---|
| Selectivity $IC_{50}$ (μM) | MMP1 | >100 | >100 | >100 | >100 |
| | MMP2 | >100 | >100 | >100 | >100 |
| | MMP3 | >100 | >100 | >100 | >100 |
| | HDAC3 | >100 | >100 | >100 | >100 |
| | HDAC8 | >100 | >100 | >100 | >100 |
| | TACE | >100 | >100 | >100 | 1.6 ± 0.2 |
| | COX-1 | >100 | >100 | >100 | >100 |
| Cytotoxicity $IC_{50}$ (μM) | HepG2 | >100 | >100 | >100 | >100 |
| | HEK293 | >100 | >100 | >100 | >100 |
| | A549 | >100 | >100 | >100 | >100 |
| Antibacterial activity $IC_{50}$ (μM) | PA-14 | >100 | >100 | >100 | >100 |

Transepithelial Electric Resistance (TEER) Experiments

With Calu-3 cell line. Human lung cancer cell line (Calu-3) (HTB-55™; ATCC) passaged 19 to 25 were seeded at a density of $3\times10^4$ cells/mL onto a hanging cell culture insert at 37° C. for 10 days with 5% $CO_2$. Every 2 days, the medium (minimum essential medium containing 1% non-essential amino acids (NEAA, 40035), 1 mM sodium pyruvate (11360070), 100 U/ml penicillin/streptomycin, 10% fetal calf serum (FCS)) was changed.

A concentration of 20% (v/v) of PAO1 culture supernatant was added together with 3 μM of compounds 169, Hit L1 or 160 into the inner compartment. The TEER of the cells was measured with Millicell ERS-2 (Electrical Resistance System) over time. Three readings were recorded for each well, Ohmic resistance values were corrected for the area of the insert (0.3 cm2) as well as the related value of a blank and reported relative to the control (no inhibitor, no supernatant treatments).

With hAELVi cell line. Human alveolar epithelial lentivirus immortalized hAELVi (Arlo) were seeded according to the reported procedure (Anna Kuehn, S. K.-W.-D.-M. (2016). Human alveolar epithelial cells expressing tight junctions to model the air-blood barrier. ALTEX.). The treatment with the PAO1 supernatant and compounds was performed as mentioned before.

LasB inhibitors can rescue the TEER value of Calu3 cells. The hydroxamic acid-based compounds inhibited the activity of LasB and maintained the TEER of the challenged cells with PAO1 supernatant as shown in FIGS. 1 and 2.

In Vitro Evaluation of Compound 169 Through an A549 Cell-Based Assay

The human lung adenocarcinoma cell line (A549) was cultured in Dulbecco's Modified Eagle Medium (DMEM), containing 10% Fetal Bovine Serum (FBS) and 1% penicillin-streptomycin mixture. Cells were maintained according to standard cell culture procedures.

To conduct the assay, 2.5-3.5*$10^3$ cells/well were seeded into a flat bottom 96-well plate (Corning™ Costar™) and incubated at 37° C.+5% $CO_2$ for 24 hours. On the following day, several concentrations of the compound 169 were tested against 10% (v/v) *Pseudomonas aeruginosa* PAO1 (DSM 22644, ATCC 15692) culture supernatant diluted in DMEM starting from 1.25 μM. The compound was initially dissolved in 99.9% Dimethyl sulfoxide (DMSO) and a final assay concentration of 0.5% (v/v) was applied to minimize the proteolytic effect of DMSO on the bacterial culture supernatant. In addition, cells were challenged with 10% (v/v) of ΔlasB PAO1 to confirm the toxic effect derived from LasB, and DMEM was included as a control without any treatment. Plates were incubated at 37° C.+5% $CO_2$ for 24 hours prior to the MTT assay.

Figure 1:
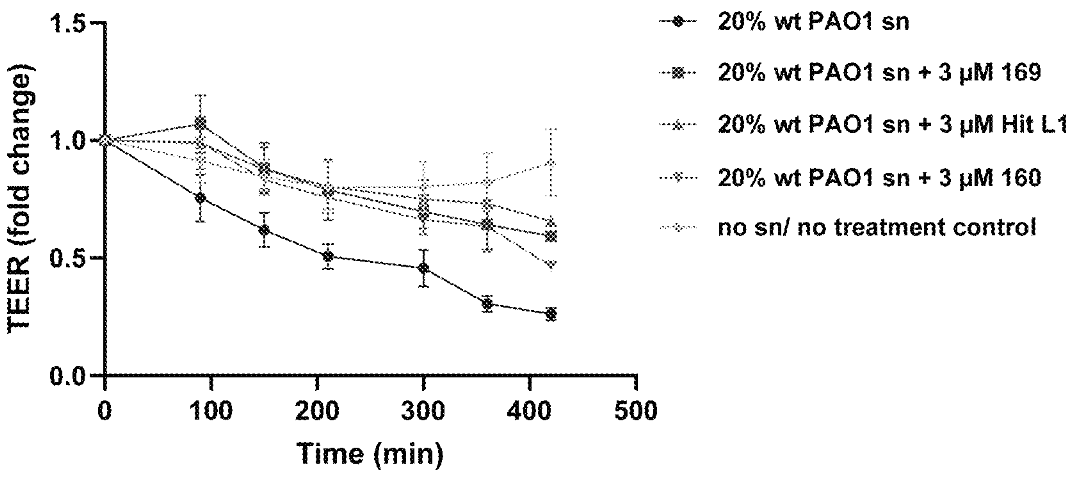
FIG. 1 shows the change in the transepithelial electrical resistance (TEER) of human lung cancer cell line (Calu3) cells challenged with 20% (v/v) PAO1 culture supernatant and treated with or without hydroxamic acid LasB inhibitors. Each curve represents the average ±standard deviation of at least three independent experiments.
Figure 2:
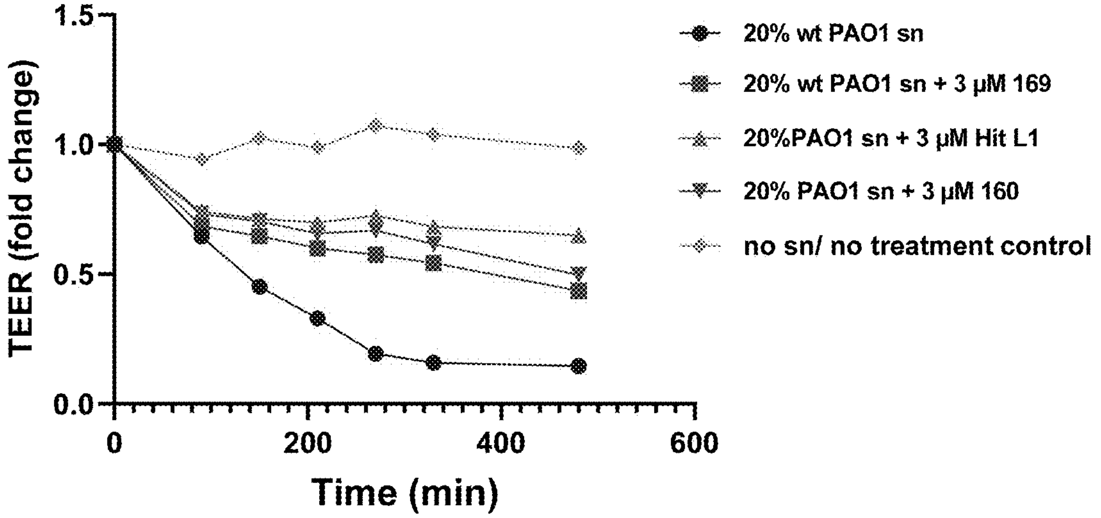
FIG. 2 shows the change in the transepithelial electrical resistance (TEER) of human alveolar epithelial lentivirus immortalized (hALVi) cells challenged with 20% (v/v) PAO1 culture supernatant and treated with or without hydroxamic acid LasB inhibitors. Each curve represents the average ±standard deviation of data derived from one experiment.
Figure 3:
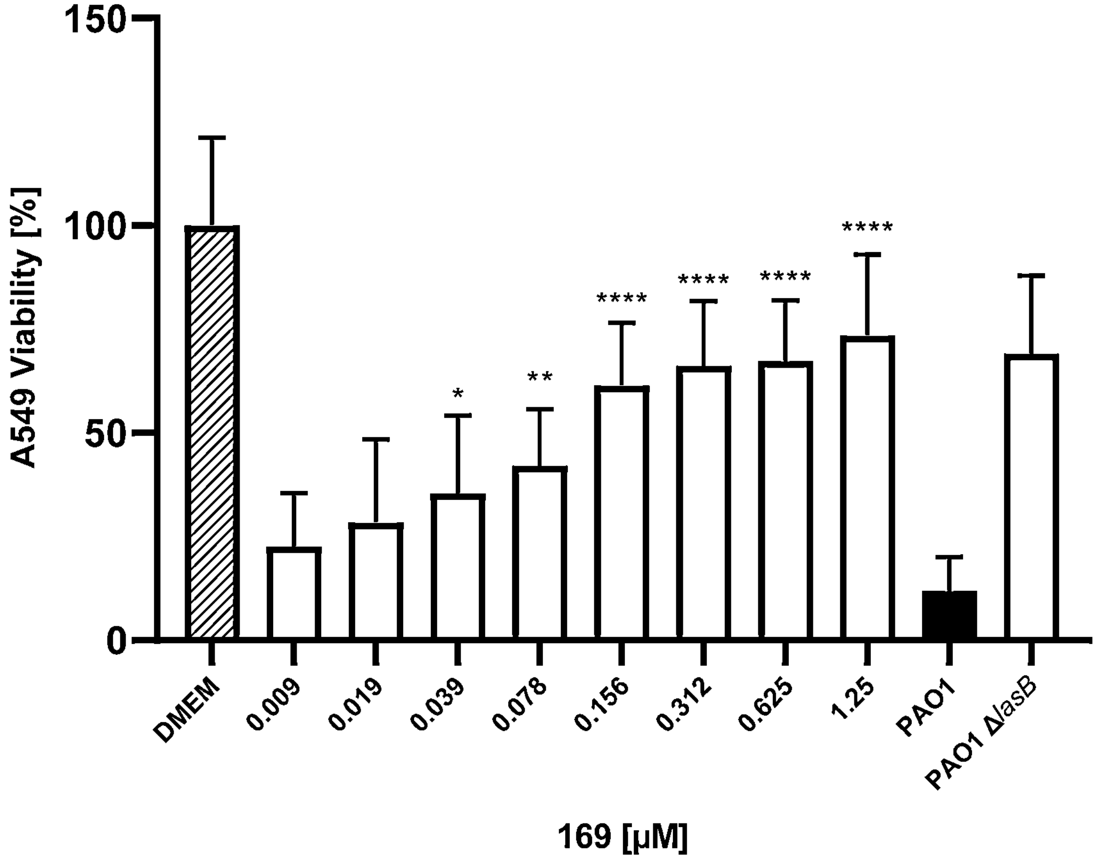

The ability of the hydroxamic acid 169 to reduce the LasB-related cytotoxicity in the A549 cell line was evaluated. This compound demonstrated excellent potency in PAO1 csn-treated cells (FIG. 3). An average cell viability of 12% and 69% was observed when cells were challenged with PAO1 and ΔlasB PAO1 csn, respectively. As expected, improvements in cell viability were achieved within this range, proving the selectivity of the compound towards LasB. Dose-dependent inhibition of LasB in a low micromolar to nanomolar range can be observed in the application of 169.

FIG. 3 shows the dose-response inhibitory effect of 169 against 10% (v/v) *P. aeruginosa* PAO1 csn, targeting LasB. The graph represents three independent experiments ±SD. One-way ANOVA statistical analysis was performed following Dunnett's multiple comparisons test, comparing the mean value of each concentration to the mean value of PAO1 without any treatment with compounds (** $p\leq0.0001$,  $p\leq0.01$, * $p\leq0.05$).

Toxicity Studies of PAO1 (DSM 22644) in *G. mellonella*

Bacteria were grown overnight, diluted to $OD_{600}$ of 0.025 in 10 ml medium, and grown for approx. 2 hours at 37° C. inside a shaker incubator until the $OD_{600}$ of 1.8-2 is reached. The culture was then serially diluted in sterile PBS (pH=7.2). Bacterial densities of 3000, 300, 30, and 3 CFU/Larva were selected for injection into groups of 15 larvae. A total volume of 5 μl was injected into each larva via the hindmost left proleg by using a syringe pump and Sterican® needles (0.30×12 mm, 30G×½). In addition, control group without injection for the quality of the larvae and a PBS control to monitor the effect of the injection were included in the experiment. All test groups and control groups were incubated at 37° C. in the dark and monitored every 2 hours from 17 hours post-infection. Larvae were considered dead when no movement was observed in response to touch or when melanization of the cuticle occurred.

Figure 4:
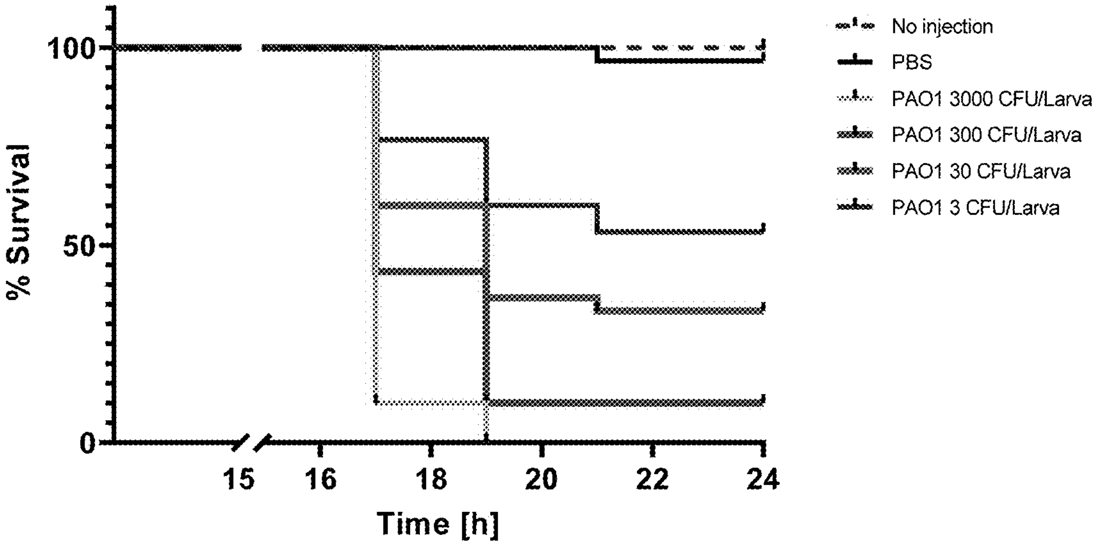

As shown in FIG. 4, *P. aeruginosa* PAO1 (strain DSM22644) caused a lethal effect in a dose-response manner, proving this model to be suitable for further studies on inhibitors. The final percentage of survival of the groups infected with 3000, 300, 30, and 3 CFU/Larva was 0%, 10%, 33%, and 53%, respectively. Simultaneously, a 97-100% survival was observed in the no-injection and PBS control groups, demonstrating the significance of the survival drop caused by bacterial infection. 3 CFU/Larva was selected for further survival studies.

FIG. 4 shows the Kaplan-Meier survival analysis of larvae infected with various CFUs of *P. aeruginosa* PAO1 (strain DSM22644). The graph represents three independent experiments. The experiment was conducted over 24 hours and each group was monitored every 2 hours from 17 hours post-infection ($p<0.0001$).

In vivo evaluation of compounds 162 and 169. Bacteria were cultured and prepared according to the previous section. Final concentrations of 50 μM, 25 μM, and 12.5 μM in combination with 3 CFU/Larva were injected into groups of 15 larvae. In addition to no injection and PBS controls, one group was infected with 3 CFU/Larva and considered the negative control. All test groups and control groups were incubated at 37° C. in the dark and monitored every 2 hours from 17 hours post-infection. Larvae were considered dead when no movement was observed in response to touch or when melanization of the cuticle occurred.

Figure 5A:
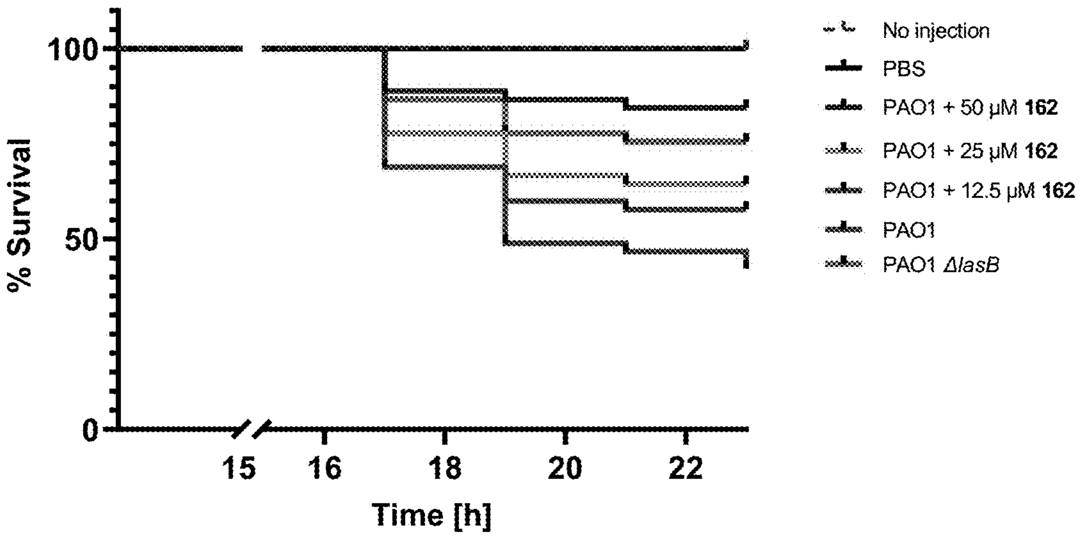
Figure 5B:
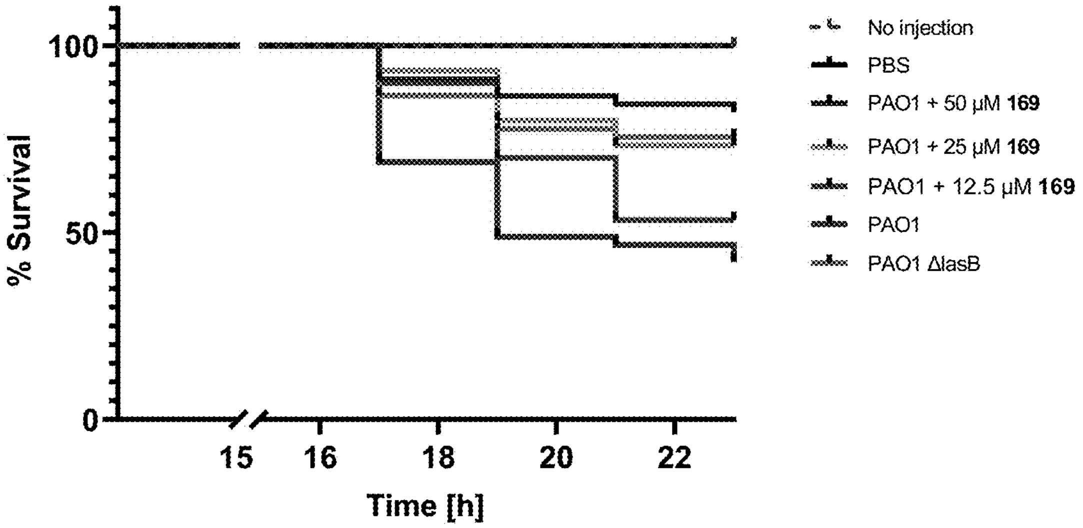

Several concentrations of compounds 162 and 169 were injected into larvae in combination with 3 CFU/Larva and the survival was monitored over the course of 24 hours (FIG. 5A and FIG. 5B). Treatment with 50 μM of 162 and 169 resulted in a final survival percentage of 84% and 82%, respectively. This shows a 40% improvement in the survival of the larvae compared to the negative control (3 CFU/Larva of bacteria without treatment). Treatment with further concentrations of 25 μM and 12.5 μM resulted in 64% and 58% for 162, and 73% and 53% for 169, respectively. In conclusion, significant survival improvement in a dose-response manner was observed in all of the test groups, suggesting both compounds as effective inhibitors against *P. aeruginosa.*

FIG. 5A and FIG. 5B show the Kaplan-Meier survival analysis of larvae infected with 3 CFU/Larva of *P. aeruginosa* PAO1 (strain DSM22644) in combination with several concentrations of 162 and 169. Each graph represents three independent experiments. The experiment was conducted over 24 h and each group was monitored every 2 h from 17 hours post-infection ($p<0.0001$).

Preparation of Lung Homogenate

The lung homogenate was prepared from pig lung, which was stored at −80° C. After thawing the lung tissue was cut into pieces of approximately 1.5 cm diameter and 0.5 to 1 cm thickness. Subsequently the bits were flash frozen in liquid nitrogen and lyophilized for 48 h.

1.2 g dried tissue was then ball milled using an IKA Tube Drive and the respective 50 mL ball milling tubes. 20 steel balls were used with target rpm of 6000, reversing the spinning direction every 30 seconds for a total of 10 min. After 10 min the tube was detached and inverted to loosen the powder. The ball milling was repeated with the same setup twice again.

To the powdery tissue 50 mL of a 10 mM Tris buffer including 2 mM $CaCl_2$ with a pH of 8.0 was added and the IKA Tube Drive used again with the same settings as described before for 10 min to disperse the tissue powder in the aqueous buffer. The yielded lung homogenate was pipetted into 15 mL falcons and stored at −80° C. until further use.

Protocol of Lung Homogenate Assay

To perform the LasB activity/inhibition assay a compound dilution was prepared in DMSO yielding a 100 fold concentration of the final concentration in the assay. LasB was diluted from a higher stock solution to a 6 μM stock in the same buffer as used for the lung homogenate. The assay was performed in Eppis. With a stepper pipette 10 μL of the prepared LasB solution was added to the Eppis to yield a final protein concentration of 300 nM. Then 188 μL of thawed lung homogenate was added with a stepper pipette. Finally, 2 μL of the 100 fold compound dilutions were added and mixed by pipetting up and down. The Eppis were incubated at 37° C. with a shaking speed of 1000 rpm for 4 h.

After 4 h, the Eppis were centrifuged at a speed of 14,000 rpm, 4° C. for 10 min to separate the soluble cleaved Elastin fragments from the non-cleaved insoluble part. 100 μL of the obtained supernatant was transferred to new Eppis, and the same volume of concentrated hydrochloric acid added. For a complete hydrolysis and release of Desmosin the Eppis were again incubated at 100° C. and 1000 rpm overnight.

The next day all Eppis were centrifuged for 1 minute at 14,000 rpm, 25° C. and then opened and incubated at 100° C. until completely dry.

To the dry Eppis 100 μL of a 100 mM ammonium formate buffer with pH 2.7 (50% MeCN in H2O) containing 100 nM Amproliumchloride as internal standard was added. To improve solvation the Eppis were shaken for 20 min at 1500 rpm. Afterwards the solutions were centrifuged again at 14,000 rpm, 4° C. for 10 min. The obtained supernatant was transferred to a 96 well plate to be submitted to LC-MSMS.

For LC-MSMS analysis a Dionex UltiMate 3000 was used consisting of a RS pump, RS autosampler and column compartment. The LC part is coupled to TSQ Quantum Access MAX Triple Quadrupole mass spectrometer. The column used is a Syncronis HILIC 50×2.1 with a particle size of 1.7μ.

The mobile phase consisted of MS grade MeCN as B and 200 mM ammonium formate in water adjusted to pH 2.7 as A. The gradient started with 90% B for 1 min. Followed by a linear gradient from 90% B to 10% B for 6.5 min. This was followed by a plateau of 10% B for 0.5 min. From minute 8 to the end of the run minute 10 a plateau of 90% B was used to equilibrate the column for the next run.

Amprolium eluted at around 0.83 minutes, while Desmosine eluted around 4.44 minutes.

The detection of the molecules was achieved in SRM mode observing the following fragmentation patterns:

Amprolium 243.130→150.1
Desmosine 526.209→351.9
Desmosine 526.209→397.0
Desmosine 526.209→436.0
Desmosine 526.209→481.1

Peak areas and response ratios were calculated using Xcalibur Quan browser with Amprolium set as internal standard. The calculation of the IC50-values was performed within Prism.

Results of Ex Vivo Lung Homogenate Assay with Purified LasB

Figure 6:
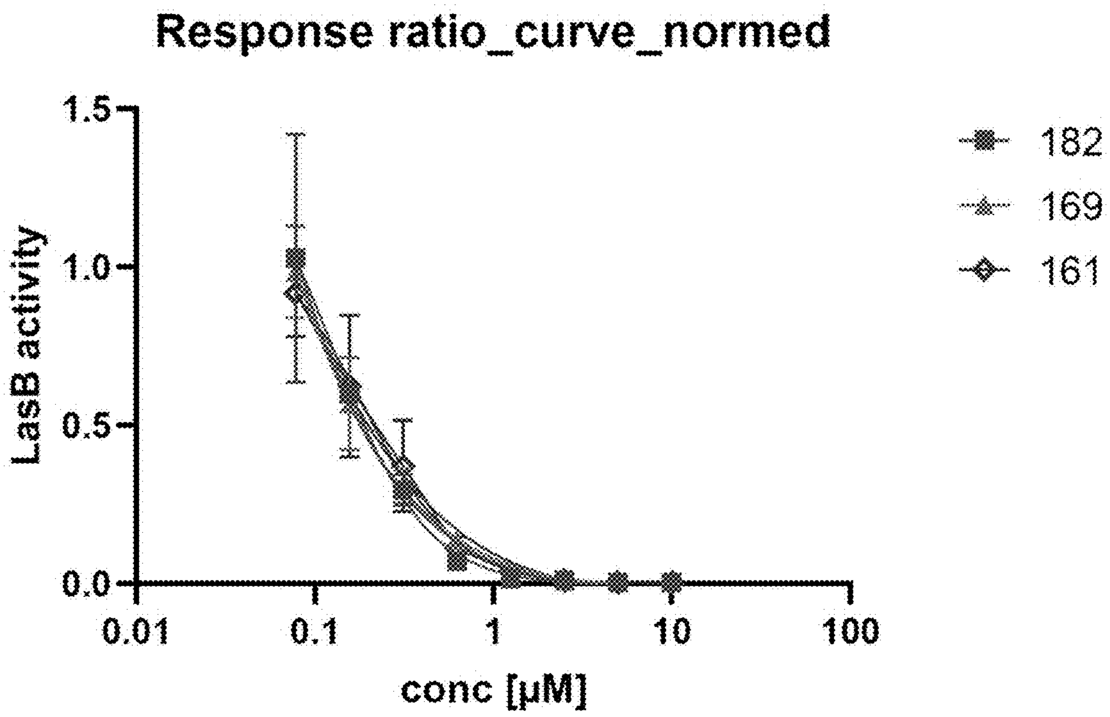

The results of the ex vivo lung homogenate assay with purified LasB are shown in FIG. 6 and Table 5.

TABLE 5

| $IC_{50}$ | | |
|---|---|---|
| Compound | $IC_{50}$ [μM] | SD |
| 182 | 0.127 | 0.088 |
| 169 | 0.077 | 0.080 |
| 161 | 0.186 | 0.058 |

The invention claimed is:

1. A compound of formula (I):

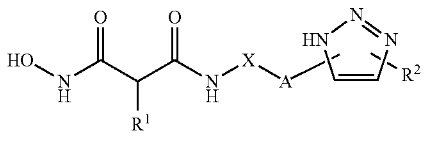

(I)

wherein

A is a bond, $CH_2$ or C═O;

X is an optionally substituted cycloalkylene group, an optionally substituted heterocycloalkylene group, an optionally substituted arylene group or an optionally substituted heteroarylene group;

$R^1$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which may optionally be substituted; and $R^2$ is hydrogen or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which may optionally be substituted;

or a pharmaceutically acceptable salt thereof.

2. A compound of formula (Ia):

(Ia)

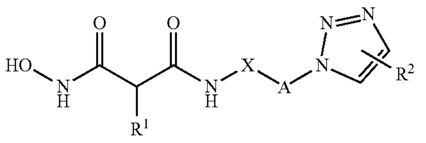

wherein

A is a bond, $CH_2$ or C═O;

X is an optionally substituted cycloalkylene group, an optionally substituted heterocycloalkylene group, an optionally substituted arylene group or an optionally substituted heteroarylene group;

$R^1$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which may optionally be substituted; and $R^2$ is hydrogen or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which may optionally be substituted;

or a pharmaceutically acceptable salt thereof.

3. A compound of formula (II):

(II)

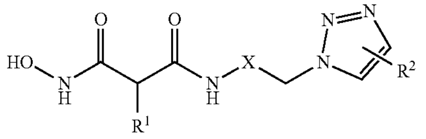

wherein

X is an optionally substituted cycloalkylene group, an optionally substituted heterocycloalkylene group, an optionally substituted arylene group or an optionally substituted heteroarylene group;

$R^1$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which may optionally be substituted; and $R^2$ is hydrogen or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which may optionally be substituted;

or a pharmaceutically acceptable salt thereof.

4. A compound according to claim 1, wherein X is an optionally substituted arylene group or an optionally substituted heteroarylene group.

5. A compound according to claim 1, wherein X is an optionally substituted phenylene group or an optionally substituted heteroarylene group having 5 or 6 ring atoms that are selected from C, N, O and S.

6. A compound according to claim 1, wherein X is a 1,3 phenylene group or a 1,4 phenylene group.

7. A compound according to claim 1, wherein $R^1$ is a $C_{1-6}$ alkyl group; a heteroalkyl group containing from 1 to 6 carbon atoms and 1, 2, 3 or 4 heteroatoms selected from O, S and N; a $C_{3-7}$ cycloalklyl group; a $C_{4-10}$ alkylcycloalkyl group; or a $C_{7-12}$ aralkyl group; all of which may optionally be substituted.

8. A compound according to claim 1, wherein $R^1$ is a $C_{1-6}$ alkyl group; a heteroalkyl group containing from 1 to 6 carbon atoms and 1, 2, 3 or 4 heteroatoms selected from O, S and N; a $C_{3-7}$ cycloalklyl group; or a group of formula —$CH_2$-$R^{11}$, wherein $R^{11}$ is a $C_{3-7}$ cycloalkyl group or an optionally substituted phenyl group.

9. A compound according to claim 1, wherein $R^1$ is a $C_{1-6}$ alkyl group; or a group of formula —$CH_2$—$R^{11}$, wherein $R^{11}$ is a phenyl group or a cyclopropyl group.

10. A compound according to claim 1, wherein $R^1$ is a $C_{1-4}$ alkyl group; or a group of formula —$CH_2$—$R^{11}$, wherein $R^{11}$ is a phenyl group or a cyclopropyl group.

11. A compound according to claim 1, wherein $R^1$ is a group of formula —$CH_2CH(CH_3)_2$ or a group of formula —$CH(CH_3)_2$.

12. A compound according to claim 1, wherein $R^2$ is a group of formula —$CH_2$—NH—$SO_2$—$R^3$ or —$CH_2$—N($CH_3$)—$SO_2$—$R^3$, wherein $R^3$ is an optionally substituted phenyl group, an optionally substituted benzyl group, an optionally substituted $C_{3-10}$ cycloalkyl group, an optionally substituted —$CH_2$—$C_{3-10}$ cycloalkyl group, a $C_{1-6}$ alkyl group or a $C_{1-6}$ heteroalkyl group.

13. A compound according to claim 1, wherein $R^2$ is a group of formula —$CH_2$—Y—$R^4$, wherein Y is selected from a bond, O, NH, S and NHCO; and $R^4$ is hydrogen, a $C_{1-6}$ heteroalkyl group or an optionally substituted phenyl group.

14. A compound according to claim 1, wherein $R^2$ is an optionally substituted phenyl group.

15. A compound according to claim 1, wherein $R^2$ is selected from the following groups:

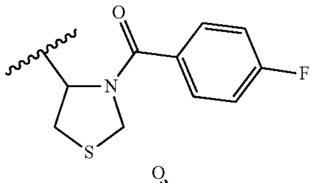

and

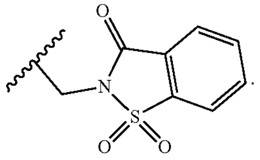

16. A pharmaceutical composition comprising a compound according to claim 1 and optionally one or more carrier substances and/or one or more adjuvants and/or one or more further antibacterial compounds.

17. A method for inhibiting the *P. aeruginosa* virulence factor LasB in a subject which comprises administering to the subject an effective amount of a compound according to claim 1, or a pharmaceutically acceptable salt thereof.

18. A method for treating a bacterial infection, which comprises administering to a subject in need of such treatment a therapeutically effective amount of a compound according to claim 1, or a pharmaceutically acceptable salt thereof.

19. A method for treating a bacterial infection caused by *P. aeruginosa* which comprises administering to a subject in need of such treatment a therapeutically effective amount of a compound according to claim 1, or a pharmaceutically acceptable salt thereof.

* * * * *